United States Patent
Chen et al.

(10) Patent No.: US 10,829,727 B2
(45) Date of Patent: Nov. 10, 2020

(54) ENGINEERED PLATFORM TO GENERATE 3D CARDIAC TISSUES

(71) Applicant: TRUSTEES OF BOSTON UNIVERSITY, Boston, MA (US)

(72) Inventors: Christopher S. Chen, Newton, MA (US); Rebeccah Luu, Cambridge, MA (US); Anant Chopra, Waltham, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 16/381,866

(22) Filed: Apr. 11, 2019

(65) Prior Publication Data

US 2019/0316068 A1    Oct. 17, 2019

Related U.S. Application Data

(60) Provisional application No. 62/656,016, filed on Apr. 11, 2018.

(51) Int. Cl.
| | |
|---|---|
| *C12M 3/00* | (2006.01) |
| *C12N 5/077* | (2010.01) |
| *C12N 5/00* | (2006.01) |
| *C12N 5/074* | (2010.01) |
| *C12M 1/34* | (2006.01) |
| *C12N 5/0735* | (2010.01) |
| *C12M 1/32* | (2006.01) |
| *C12M 1/12* | (2006.01) |

(52) U.S. Cl.
CPC ............ *C12M 21/08* (2013.01); *C12M 41/46* (2013.01); *C12N 5/0062* (2013.01); *C12N 5/0606* (2013.01); *C12N 5/0657* (2013.01); *C12N 5/0696* (2013.01); *C12M 23/12* (2013.01); *C12M 25/14* (2013.01); *C12N 2533/90* (2013.01)

(58) Field of Classification Search
CPC .............................. C12M 23/12; C12M 21/08
See application file for complete search history.

(56) References Cited

U.S. PATENT DOCUMENTS

| | | | |
|---|---|---|---|
| 6,164,850 | A | 12/2000 | Speakman |
| 6,166,184 | A | 12/2000 | Hendriks et al. |
| 6,224,893 | B1 | 5/2001 | Langer et al. |
| 7,291,002 | B2 | 11/2007 | Russell et al. |
| 9,057,734 | B2 | 6/2015 | Cohen et al. |
| 9,238,150 | B2 | 1/2016 | Deisseroth et al. |
| 2005/0138675 | A1 | 6/2005 | Hirakawa et al. |

(Continued)

OTHER PUBLICATIONS

Chang et al., "Genetics of hypertrophic cardiomyopathy" Curr. Opin. Cardiol. 25(3): 205-209 (2010).

(Continued)

*Primary Examiner* — Jonathan M Hurst
(74) *Attorney, Agent, or Firm* — Nixon Peabody LLP; Ronald I. Eisenstein

(57) ABSTRACT

Described herein are a system, device, methods and compositions related to generating 3-dimensional cardiac tissues. Also described herein are a system, device, and methods of maturing 3-dimensional cardiac tissues and maintaining their viability in culture.

14 Claims, 14 Drawing Sheets
(11 of 14 Drawing Sheet(s) Filed in Color)

(56) References Cited

U.S. PATENT DOCUMENTS

| | | | |
|---|---|---|---|
| 2010/0143259 A1* | 6/2010 | Ma | C09K 11/025 424/9.6 |
| 2013/0274838 A1 | 10/2013 | Entcheva et al. | |
| 2014/0220555 A1* | 8/2014 | Chen | C12N 5/0062 435/5 |
| 2016/0089821 A1 | 3/2016 | Atkins et al. | |
| 2019/0025291 A1 | 1/2019 | Eggan et al. | |

OTHER PUBLICATIONS

Crumb et al. "An evaluation of 30 clinical drugs against the comprehensive in vitro proarrhythmia assay (CiPA) proposed ion channel panel" J Pharmacol Toxicol Meth 81:251-262 (2016).

Desroches et al., "Functional scaffold-free 3-D cardiac microtissues: a novel model for the investigation of heart cells" AJP Hear. Circ. Physiol. 302(10): H2031-H2042 (2012).

Geisterfer-Lowrance et al., "A molecular basis for familial hypertrophic cardiomyopathy: A β cardiac myosin heavy chain gene missense mutation" Cell 62(5): 999-1006 (1990).

Geisterfer-Lowrance et al., "A Mouse Model of Familial Hypertrophic Cardiomyopathy", Science 272 (5262): 731-734 (1996).

Germanguz, I. et al. Molecular characterization and functional properties of cardiomyocytes derived from human inducible pluripotent stem cells. J. Cell. Mol. Med. 15, 38-51 (2011).

Hansen et al. "Development of a drug screening platform based on engineered heart tissue" Circ. Res. 107, 35-44 (2010).

Hinson et al. "Titin mutations in iPS cells define sarcomere insufficiency as a cause of dilated cardiomyopathy", Science 349(6251): 982-986 (2015).

Hirt et al. "Increased afterload induces pathological cardiac hypertrophy: A new in vitro model" Basic Res. Cardiol. 107(307): 1-16 (2012).

Karakikes et al., "Human Induced Pluripotent Stem Cell-Derived Cardiomyocytes: Insights into Molecular, Cellular and Functional Phenotypes" Circ. Research 117 (1): 80-88 (2016).

Legant et al. "Microfabricated tissue gauges to measure and manipulate forces from 3D microtissues", Proc. Natl. Acad. Sci. 106(25): 10097-10102 (2009).

Lian et al. "Directed cardiomyocyte differentiation from human pluripotent stem cells by modulating Wnt / b-catenin signaling under fully defined conditions", Nature Protocols 8:162-175 (2013).

Lloyd-Jones et al. "Executive summary: Heart disease and stroke statistics—2010 update: A report from the American heart association" Circulation 121, (2010).

Lundy et al.,Structural and Functional Maturation of Cardiomyocytes Derived from Human Pluripotent Stem Cells. Stem Cells Dev. 22 (14): 1991-2002 (2013).

Marsiglia et al., "Hypertrophic Cardiomyopathy: How do Mutations Lead to Disease?" Arq. Bras. Cardiol. 295-304 (2014) doi:10.5935/abc.20140022.

Nag et al. "Contractility parameters of human-cardiac myosin with the hypertrophic cardiomyopathy mutation R403Q show loss of motor function" Sci. Adv. 1(9) e1500511-e1500511 (2015).

Zimmerman et al. "Tissue engineering of a differentiated cardiac muscle construct", Circ. Res. 90(2): 223-230 (2002).

Otsuji et al., "Progressive maturation in contracting cardiomyocytes derived from human embryonic stem cells: Qualitative effects on electrophysiological responses to drugs", Stem Cell Res. 4(3): 201-213 (2010).

Radisic et al. "Functional assembly of engineered myocardium by electrical stimulation of cardiac myocytes cultured pn scaffolds" Proc. Natl. Acad. Sci. 101(52): 18129-18134 (2004).

Robertson et al. ,"Concise review: Maturation phases of human pluripotent stem cell-derived cardiomyocytes" Stem Cells 31(5): 829-837 (2013).

Roden "Predicting drug-induced QT prolongation and torsades de pointes", Physiol. 594(9):2459-2468 (2016).

Ronaldson et al. "Advanced maturation of human cardiac tissue grown from pluripotent stem cells." Nature 556: 239-243 (2018) doi:10.1038/s41586-018-0016-3.

Terstappen et al. "Screening technologies for ion channel drug discovery" Future Med Chem. 2(5): 715-730 (2010).

Towbin "Inherited cardiomyopathies" Circ J 78, 2347-2356 (2014).

* cited by examiner

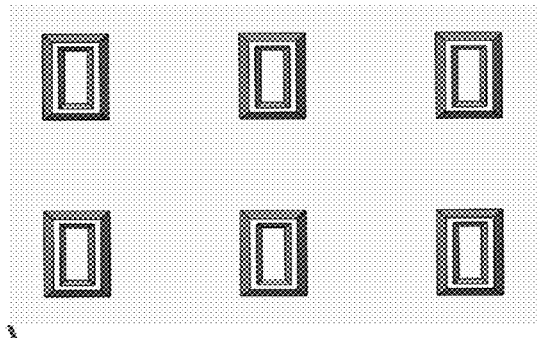
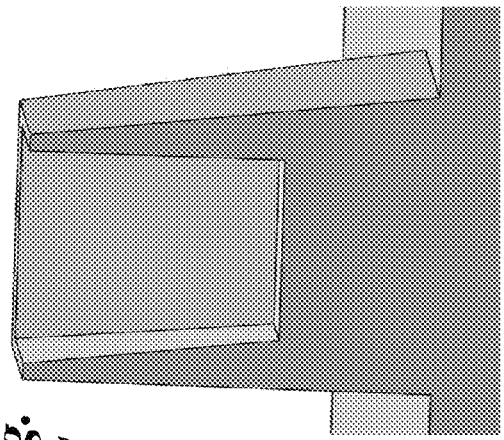
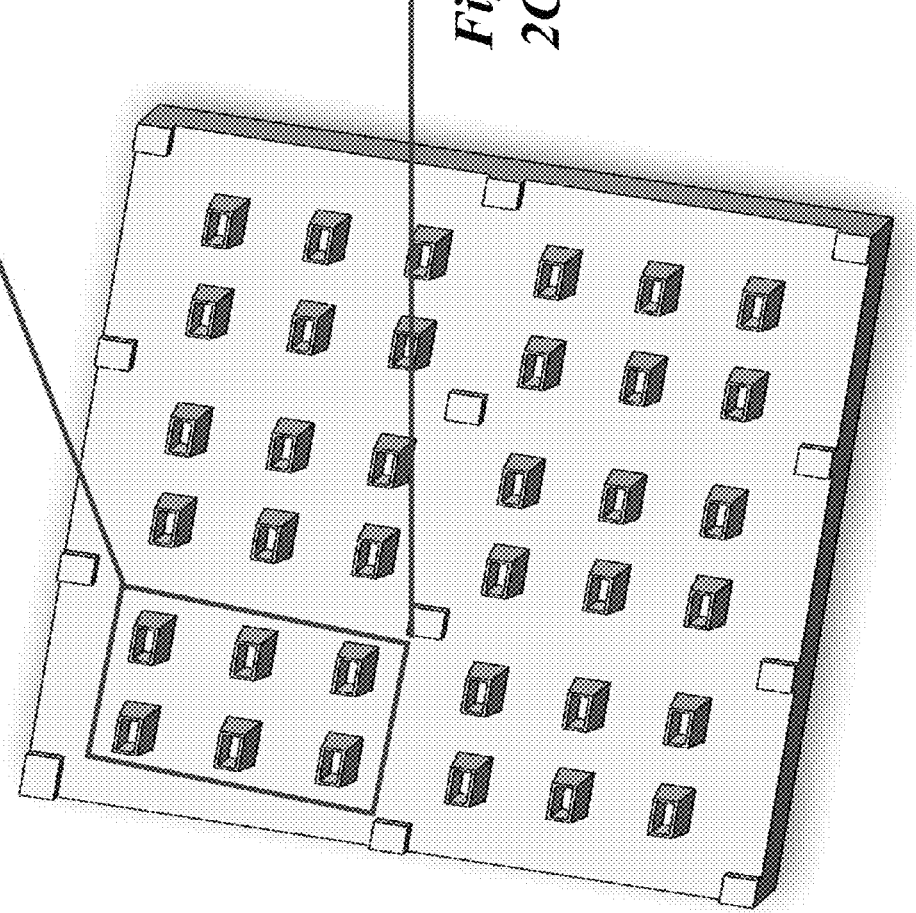
Fig. 2B
Fig. 2C
Fig. 2A

*Fig. 3A*
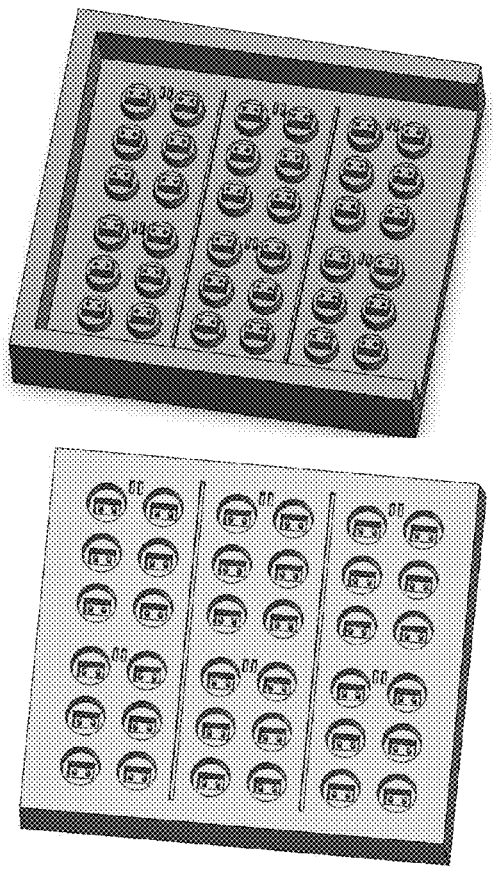
*Fig. 3B*
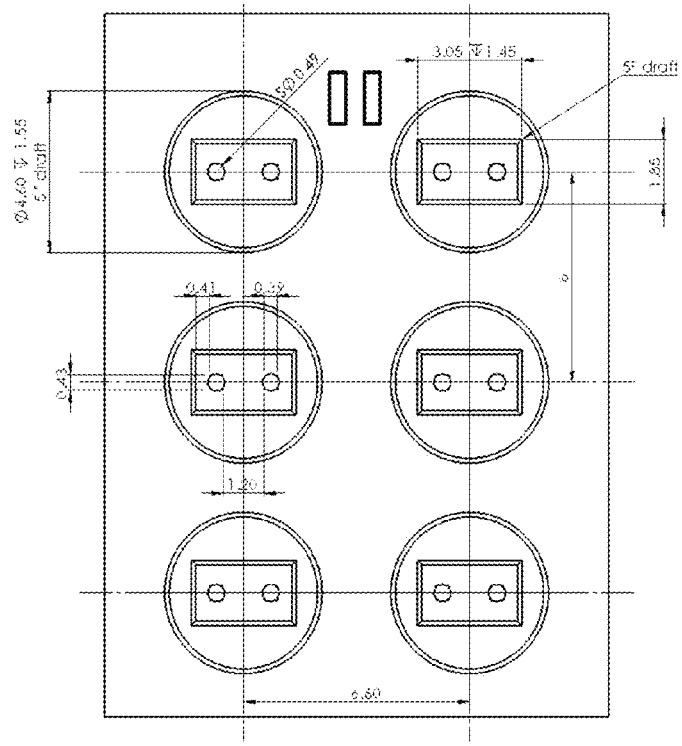
*Fig. 3C*

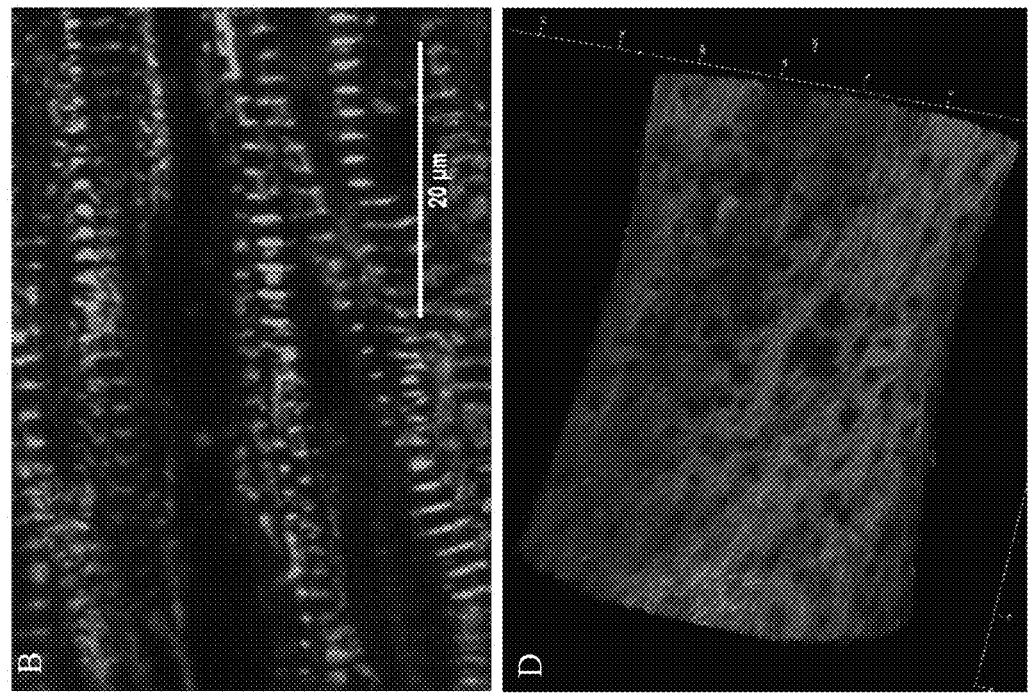
*Fig. 6A* *Fig. 6B*
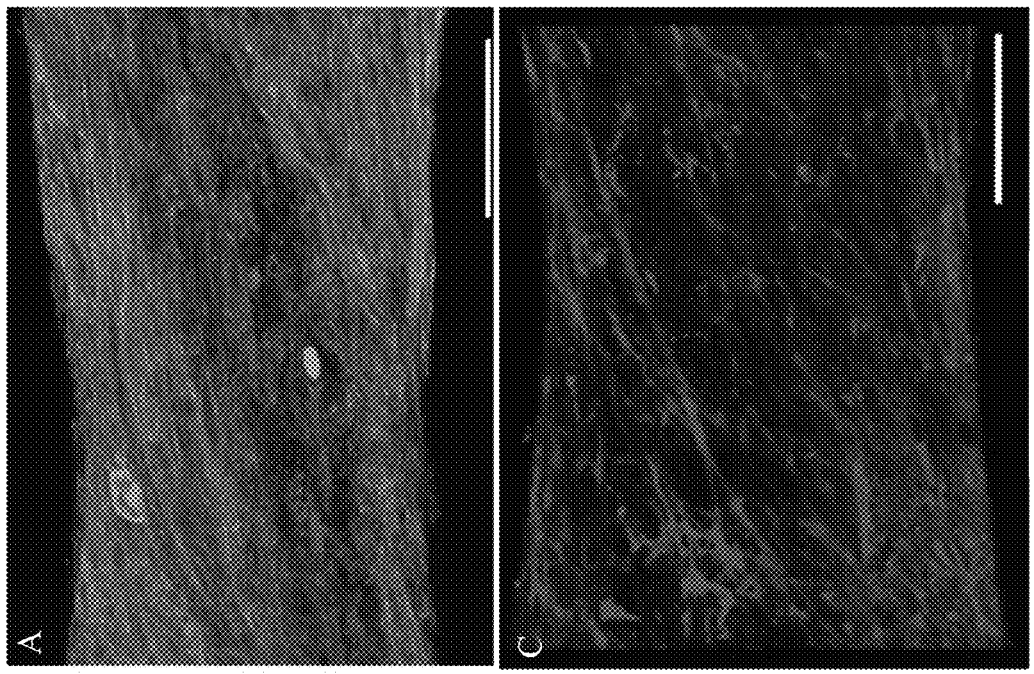
*Fig. 6C* *Fig. 6D*

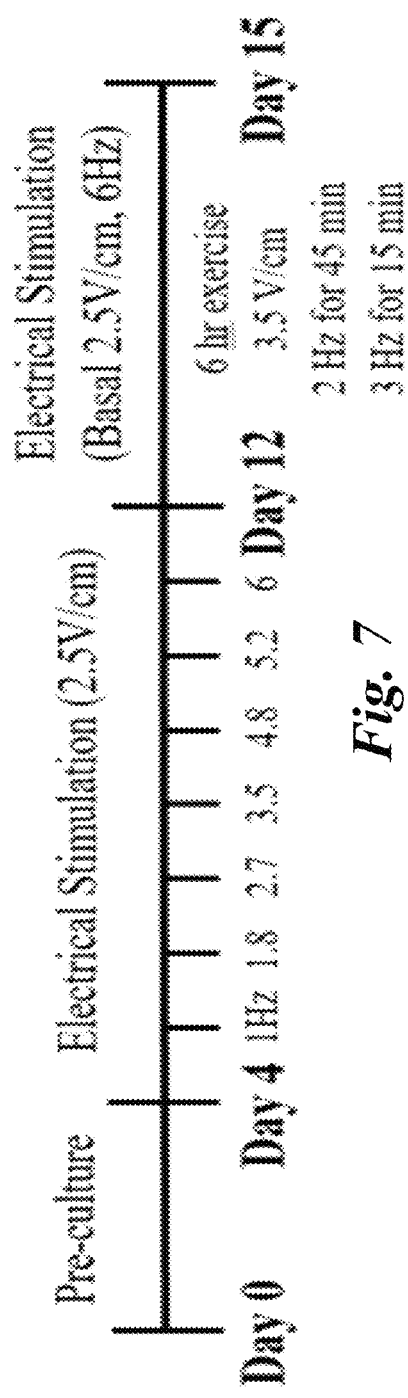
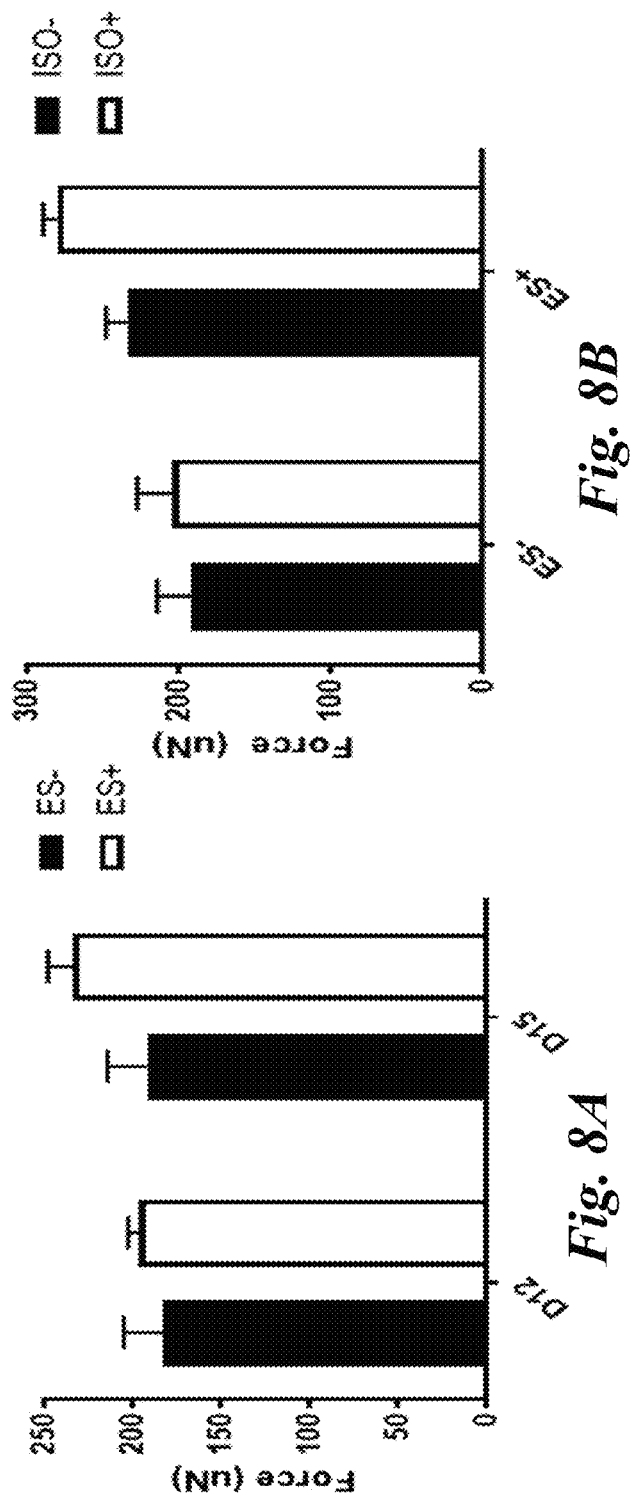
Fig. 7
Fig. 8A
Fig. 8B

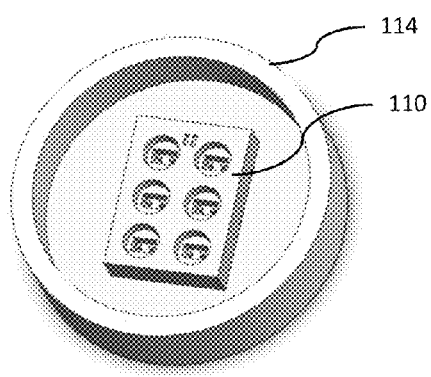
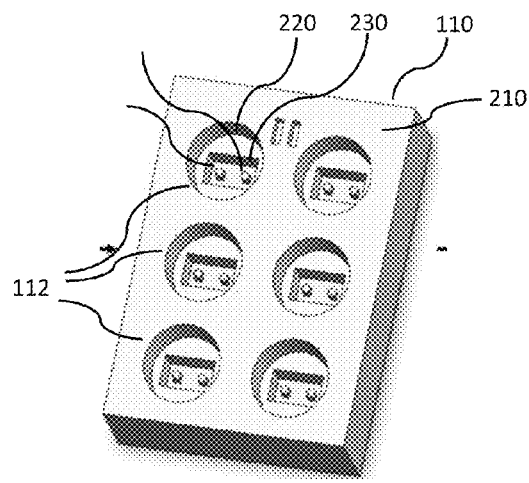
Fig. 13A          Fig. 13B
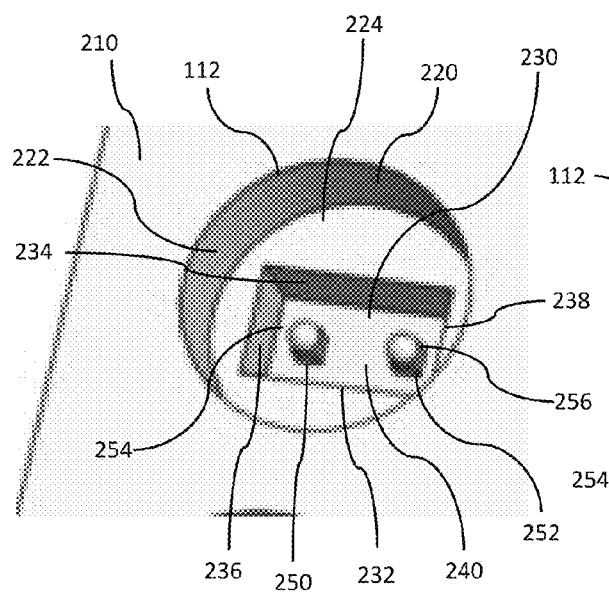
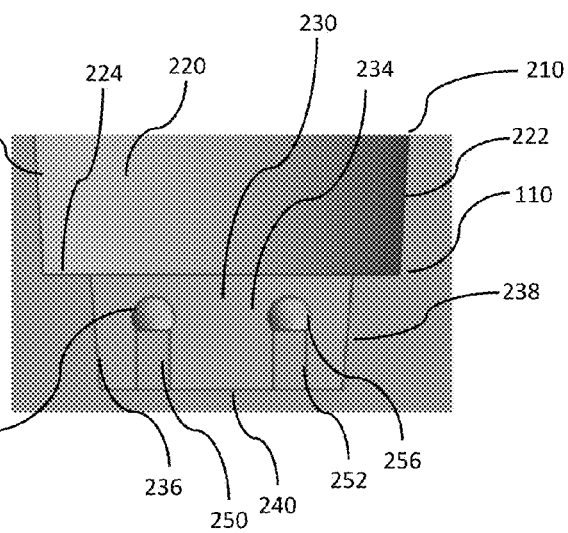
Fig. 13C          Fig. 13D

ENGINEERED PLATFORM TO GENERATE 3D CARDIAC TISSUES

CROSS-REFERENCE TO RELATED APPLICATIONS

This application is a 35 U.S.C. § 111(a) Utility Application which claims benefit under 35 U.S.C. § 119(e) of U.S. Provisional Application No. 62/656,016 filed Apr. 11, 2018, the contents of which are incorporated herein by reference in their entirety.

GOVERNMENT SUPPORT

This invention was made with government support under Contract No. EEC1647837 awarded by the National Science Foundation. The government has certain rights in the invention.

TECHNICAL FIELD

The technology described herein relates to methods of disease modelling, engineering cardiac tissues and uses thereof.

BACKGROUND

Studies to gain mechanistic understanding of heart dysfunction based on animal and traditional cell culture models can be useful but have significant limitations. Animal models are low throughput and have failed to recapitulate many aspects of human cardiac biology, and 2D culture models utilizing human induced pluripotent stem cell derived cardiomyocytes (iPSC-CMs) are higher throughput but have failed to incorporate one or more in vivo parameters, such as 3D architecture, electrical pacing and mechanical constraint. There is a significant need for devices that model the 3D structure of the heart and provide a platform to investigate cardiac diseases, cardiac toxicity, and discover new therapeutics for cardiac disease.

SUMMARY

The devices, systems, and methods provided herein are based, in part, on an improved device that enhances longevity of cardiac tissues and permits maturation of cardiomyocytes. The devices and systems described herein permit the generation of physiologically relevant cardiac tissue models, which can be used in assessing the efficacy of agents in the treatment of cardiovascular disease and/or toxicity of any pharmacological agent on cardiac cells. The cardiac tissues generated using the devices, systems, and methods described herein are formed in a manner that permits the tissue to comprise dimensions that permit proper oxygen and nutrient diffusion, while still retaining sufficient strength to support beating of the tissue as a unit without tearing from the pillars.

Accordingly, provided herein in one aspect is a system for generating 3-dimensional (3D) cardiac tissues, the system comprising: a solid support base, a well in the support base, the well including a lower chamber and an upper chamber; at least two pillars in the lower chamber operable to produce cardiac tissues across the pillars; and a head on top of each pillar, each of the heads protruding into the upper chamber wherein the heads are chemically treated in a sticky coating that is different from that of the pillar.

In one embodiment of this aspect and all other aspects provided herein, the system further comprises muscle cells, cardiomyocytes, or stem cells in the well.

In another embodiment of this aspect and all other aspects provided herein, the pillars are flexible and permit contraction of the cells.

In another embodiment of this aspect and all other aspects provided herein, the pillars are 0.01 to 2.0 millimeters (mm) in height.

In another embodiment of this aspect and all other aspects provided herein, a spring constant of the pillars is 0.05-15 micronewtons/micrometer ($\mu N/\mu m$).

In another embodiment of this aspect and all other aspects provided herein, the head on top of each pillar is spherically shaped.

In another embodiment of this aspect and all other aspects provided herein, the head on top of each pillar includes a portion overhanging the pillar.

In another embodiment of this aspect and all other aspects provided herein, the head on top of each pillar is chemically treated to promote cell adhesion.

In another embodiment of this aspect and all other aspects provided herein, the chemical treatment or sticky coating comprises plasma, poly-lysine, and/or glutaraldehyde.

In another embodiment of this aspect and all other aspects provided herein, the upper chamber is larger than the lower chamber, and wherein the upper chamber includes a tapered wall in contact with the lower chamber.

In another embodiment of this aspect and all other aspects provided herein, the upper chamber is cylindrically shaped and wherein the lower chamber is rectangular shaped.

In another embodiment of this aspect and all other aspects provided herein, the solid support base is rectangular shaped.

In another embodiment of this aspect and all other aspects provided herein, the system further comprises at least one additional well having a lower chamber and an upper chamber in the solid support base comprising: at least two pillars in the lower chamber of the another well operable to produce cardiac tissues between the pillars; and a head on top of each pillar, each of the heads protruding into the upper chamber of the another well.

In another embodiment of this aspect and all other aspects provided herein, the system further comprises an extracellular matrix in the well.

In another embodiment of this aspect and all other aspects provided herein, the extracellular matrix is selected from the group consisting of: collagen, fibronectin, fibrinogen, poly-lysine, vitronectin, laminin, elastin, tenascin, and Matrigel®.

In another embodiment of this aspect and all other aspects provided herein, the solid support base is fabricated from polydimethylsiloxane (PDMS), polyurethane (PU), or poly (ethylene glycol) (PEG). Other polymers having tunable elastic moduli are also contemplated for use in the preparation of a solid support base as described herein.

In another embodiment of this aspect and all other aspects provided herein, the PDMS elastomer to PDMS base ratio is 1:5, 1:10, or 1:20.

In another embodiment of this aspect and all other aspects provided herein, the system further comprises a stimulator having an electrode that generates an electrical stimulus to the well and/or pillars. In one embodiment, stimulation of the tissues is achieved using two carbon electrodes placed on either side of the device, which are then connected to an electrical impulse generator In another embodiment of this aspect and all other aspects provided herein, the system further comprises a measurement device operable for measuring contractile function of the tissue generated in the well.

In another embodiment of this aspect and all other aspects provided herein, the system further comprises a device for measuring the electrical function of the tissue.

In another embodiment of this aspect and all other aspects provided herein, the system further comprises cells adhered to the pillars to form the tissue spanning across the pillars.

In another embodiment of this aspect and all other aspects provided herein, the system further comprises a petri dish, wherein the solid support base is adhered to the petri dish.

Another aspect provided herein relates to a device for generating 3-dimensional (3D) cardiac tissues, the device comprising: a solid support base having a top surface; a plurality of wells accessible through the top surface, each of the wells including a top well and a lower base well; at least two pillars in each of the lower base wells operable to produce cardiac tissues across the pillars; and a head on top of each pillar, each of the heads protruding into the corresponding top wells.

Another aspect provided herein relates to a method of maturing cardiomyocytes in culture, the method comprising, culturing cardiomyocytes in the device or system as described herein and exposing the cardiomyocytes to electrical stimulation, thereby maturing the cardiomyocytes in culture.

In one embodiment of this aspect and all other aspects provided herein, the cardiomyocytes are stem cell-derived cardiomyocytes.

In another embodiment of this aspect and all other aspects provided herein, the stem cell-derived cardiomyocytes are differentiated from an induced pluripotent stem cell (iPS cell) or an embryonic stem cell.

In another embodiment of this aspect and all other aspects provided herein, the stem cell-derived cardiomyocytes are derived from a subject with a muscular disease or disorder (e.g., a cardiac muscle disease or disorder).

In another embodiment of this aspect and all other aspects provided herein, the muscular disease or disorder is genetic cardiomyopathy, hypertrophic cardiomyopathy, dilated cardiomyopathy, cardiac arrhythmia, arrhythmogenic right ventricular dysplasia (ARVD), Duchenne muscular dystrophy, and diabetic cardiomyopathy.

In another embodiment of this aspect and all other aspects provided herein, the method further comprises co-culturing the cardiomyocytes with stromal stem cells.

In another embodiment of this aspect and all other aspects provided herein, the cardiomyocytes are human cardiomyocytes.

In another embodiment of this aspect and all other aspects provided herein, the cardiomyocytes are genetically modified.

In another embodiment of this aspect and all other aspects provided herein, the method further comprises detecting at least one phenotypic characteristic of the cardiomyocytes.

In another embodiment of this aspect and all other aspects provided herein, the electrical stimulation frequency is 0.1 Hz or more, 0.5 Hz or more, 1 Hz or more, 1.8 Hz or more, 2 Hz or more, 2.7 Hz or more, 3 Hz or more, 3.5 Hz or more, 4 Hz or more, 4.8 Hz or more, 5 Hz or more, 5.2 Hz or more, 6 Hz or more, 7 Hz or more, 8 Hz or more, 9 Hz or more, or 10 Hz.

In another embodiment of this aspect and all other aspects provided herein, the electrical stimulation is conducted 4 days after the stem cell-derived cardiomyocytes are cultured in a device or system as described herein.

In another embodiment of this aspect and all other aspects provided herein, the electrical stimulation is conducted for 6 hours per day for three days.

Also provided herein, in another aspect is a method of evaluating cardiotoxicity of an agent, the method comprising: (a) culturing cardiomyocytes in a device or system as described herein, (b) contacting cardiomyocytes with the agent; and (c) detecting modulation of at least one phenotypic characteristic associated with cardiotoxicity in the cardiomyocytes; wherein the modulation of at least one phenotypic characteristic associated with cardiotoxicity compared to a reference level indicates that the agent is cardiotoxic.

In one embodiment of this aspect and all other aspects provided herein, the agent is selected from the group consisting of a small molecule, an antibody, a peptide, a genome editing system, and a nucleic acid.

In another embodiment of this aspect and all other aspects provided herein, the phenotypic characteristic is associated with impaired contractile function, decreased beat rate, impaired electrical function, impaired metabolic function, a decrease in cell viability, or a decrease in expression of a cardiac marker.

In another embodiment of this aspect and all other aspects provided herein, cardiotoxicity of an agent is indicated by the agent's effect on one or more of: cell viability, cell size, sarcomere length, organization of sarcomeres within a tissue, a biopotential or electrical property of a population of cardiomyocytes, mitochondrial function, gene expression, beat rate, beat strength, and contractility.

Another aspect provided herein relates to a disease model comprising a cardiomyocyte prepared as described herein, wherein the cardiomyocyte is derived from a subject with a muscular disease or disorder, or wherein the cardiomyocyte genetically modified such that the cardiomyocyte expresses a disease phenotype.

In one embodiment of this aspect and all other aspects provided herein, the muscular disease or disorder is genetic cardiomyopathy, hypertrophic cardiomyopathy, dilated cardiomyopathy, cardiac arrhythmia, arrhythmogenic right ventricular dysplasia (ARVD), Duchenne muscular dystrophy, and diabetic cardiomyopathy.

In another embodiment of this aspect and all other aspects provided herein, the cardiomyocytes are human cardiomyocytes.

In another embodiment of this aspect and all other aspects provided herein, the cardiomyocytes are stem cell-derived cardiomyocytes.

In another embodiment of this aspect and all other aspects provided herein, the cardiomyocytes are genetically modified.

In another embodiment of this aspect and all other aspects provided herein, the genetic modification is a mutation in the gene or RNA encoding the polypeptide, beta-myosin heavy chain (β-MHC).

In another embodiment of this aspect and all other aspects provided herein, the genetic modification is an arginine substituted for a glutamine at position 403 (R403Q).

Another aspect provided herein relates to a kit comprising a device or system as described herein, and packaging materials therefor.

In one embodiment of this aspect and all other aspects provided herein, the kit further comprises cell culture medium and instructions to permit preparation of mature cardiomyocytes and/or stem cell-derived cardiomyocytes.

In another embodiment of this aspect and all other aspects provided herein, the cardiomyocytes are human.

In another embodiment of this aspect and all other aspects provided herein, the cardiomyocytes are derived from a subject with a muscular disease or disorder.

Another aspect provided herein relates to a method for generating cardiac tissues, comprising: providing a device including at least one well including a plurality of pillars coupled to the bottom surface of each of at least one well, each pillar including a head at a terminal end thereof, wherein each of at least one well is surrounded by a plurality of ridges, wherein the heads are chemically treated in a sticky coating that is different from that of the pillar; immersing the device in a suspension of cardiomyocytes; optionally delivering the suspension of cardiomyocytes into the at least one well; polymerizing the suspension to form a matrix; culturing the cardiomyocytes over time, to spontaneously compact the matrix, wherein the pillars anchor the contracting matrix, constraining the contraction of the matrix to form a band of cardiac tissue that spans across the pillars, thereby allowing the cardiomyocytes to mature; and measuring a contractile function of the band of cardiac tissue, wherein measuring comprises: imaging the device, over time, to acquire image data determining a force exerted on the pillars based on at least the image data and a spring constant corresponding to each pillar; and identifying a contractile function of the band of cardiac tissue based on at least the determined force, wherein the contractile function includes one or more of beat frequency, contraction duration, change in beat frequency over time, change in contraction duration over time, or variance in any of these phenotypic characteristics.

In one embodiment of this aspect and all other aspects provided herein, the method further comprises chemically treating the head at the terminal end of the pillar to promote cell adhesion.

In another embodiment of this aspect and all other aspects provided herein, the chemical treatment or sticky coating is one of plasma, poly-lysine, and/or glutaraldehyde.

In another embodiment of this aspect and all other aspects provided herein, the method further comprises muscle cells, cardiomyocytes, or stem cells in the well.

In another embodiment of this aspect and all other aspects provided herein, the cardiomyocytes are stem cell-derived cardiomyocytes.

In another embodiment of this aspect and all other aspects provided herein, the stem cell-derived cardiomyocytes are differentiated from an induced pluripotent stem cell (iPS cell) or an embryonic stem cell.

In another embodiment of this aspect and all other aspects provided herein, the stem cell-derived cardiomyocytes are derived from a subject with a muscular disease or disorder.

In another embodiment of this aspect and all other aspects provided herein, the cardiomyocytes are human cardiomyocytes.

In another embodiment of this aspect and all other aspects provided herein, the cardiomyocytes are genetically modified.

In another embodiment of this aspect and all other aspects provided herein, the method further comprises stimulating and/or measuring the electrical function of the cardiac tissue.

In another embodiment of this aspect and all other aspects provided herein, the electrical stimulation frequency is 0.1 Hz or more, 0.5 Hz or more, 1 Hz or more, 1.8 Hz or more, 2 Hz or more, 2.7 Hz or more, 3 Hz or more, 3.5 Hz or more, 4 Hz or more, 4.8 Hz or more, 5 Hz or more, 5.2 Hz or more, 6 Hz or more, 7 Hz or more, 8 Hz or more, 9 Hz or more, or 10 Hz.

In another embodiment of this aspect and all other aspects provided herein, the cardiac tissues are viable for up to 7 days or more, 14 days or more, 21 days or more, 28 days or more, or 35 days.

In another embodiment of this aspect and all other aspects provided herein, the method further comprises, prior to providing a device, making the device using a 3D-printed mold and a curable polymer.

In another embodiment of this aspect and all other aspects provided herein, the curable polymer is PDMS, polyurethane (PU), or poly(ethylene glycol) (PEG).

In another embodiment of this aspect and all other aspects provided herein, the PDMS elastomer to PDMS base ratio is 1:5, 1:10, or 1:20.

In another embodiment of this aspect and all other aspects provided herein, the pillars are 0.01 to 2.0 millimeters (mm) in height.

In another embodiment of this aspect and all other aspects provided herein, the pillars are 0.6 mm apart or more, 0.7 mm apart or more, 0.8 mm apart or more, 0.9 mm apart or more, 1.0 mm apart or more, 1.1 mm apart or more, 1.2 mm apart or more, 1.3 mm apart or more, 1.4 mm apart or more, 1.5 mm apart or more, 2.0 mm apart or more, 2.5 mm apart or more, or 3.0 mm.

In another embodiment of this aspect and all other aspects provided herein, a spring constant of the pillars is 0.05-15 $\mu N/\mu m$.

In another embodiment of this aspect and all other aspects provided herein, the head includes a portion overhanging the pillar.

In another embodiment of this aspect and all other aspects provided herein, the suspension of cardiomyocytes comprises stem cell-derived cardiomyocytes at different stages of maturity.

In another embodiment of this aspect and all other aspects provided herein, the suspension of cardiomyocytes further comprises co-culture with stromal cells.

In another embodiment of this aspect and all other aspects provided herein, the stem cell-derived cardiomyocytes have a purity of 50% or more, 60% or more, 70% or more, 80% or more, 90% or more, or are 100% pure (i.e. "substantially pure").

Another aspect provided herein relates to a method of maturing muscle cells in culture, the method comprising, culturing muscle cells in the device or system as described herein, thereby maturing the muscle cells in culture.

In one embodiment of this aspect and all other aspects provided herein, the muscle cells are stem cell-derived muscle cells, smooth muscle cells, or skeletal muscle cells.

BRIEF DESCRIPTION OF THE DRAWINGS

This patent or application file contains at least one drawing executed in color. Copies of this patent or patent application publication with color drawing (s) will be provided by the Office upon request and payment of the necessary fee.

FIG. 1A shows a schematic of the prototype negative mold. FIG. 1B shows a schematic of the resulting positive mold. FIG. 1C shows schematics of the different design conditions tested.

FIGS. 2A-2C show a schematic of chemical cap treatment platform. FIG. 2A shows a schematic of the platform for the chemical cap treatment process. FIG. 2B shows a top view of the wells. FIG. 2C shows a sectioned view of a single well.

FIGS. 3A-3C show a schematic and drawing of final platform. FIG. 3A shows a 3D CAD model of the negative mold of the final platform design. FIG. 3B shows a 3D CAD model of the resulting positive platform mold. FIG. 3C shows a drawing of the top view of a single device (positive). Dimensions are in mm.

FIG. 4A shows a schematic of a typical experimental timeline. FIG. 4B shows a schematic of the device cell seeding process. From left to right: a single device adhered to a 35 mm dish (far left schematic), thrombin solution is added and centrifuged for uniform distribution (second schematic), reconstitution mixture is added (third schematic), after fibrin polymerization media (far right schematic) is added.

FIG. 5A shows a bright field top view image of an iPSC-CM cardiac tissue suspended between two posts with spherical caps. FIG. 5B shows force tracing of an electrically paced cardiac tissue over time. FIG. 5C shows mean contractile force output of iPSC-CM tissues over 15 days. Tissues start to contract as a unit by day 5 (N≥4, p<0.05).

FIGS. 6A-6D show immunofluorescence staining of tissue structure. FIG. 6A shows maximum projection in the z-axis of tissue stained for Z discs (α-actinin A, green). Scale bar 100 µm. FIG. 6B shows an enlarged view of sarcomeric structures. (α-actinin A, green). Scale bar 20 µm. FIG. 6C shows maximum projection in the z-axis of tissue stained for collagen I (red). Scale bar 100 µm. FIG. 6D shows 3D reconstruction of the tissue stained for α-actinin, collagen I (red), and nuclei (blue).

FIG. 7 shows the electrical stimulation regimen. Tissues are pre-cultured for five days and then subjected to a frequency-ramp up regimen from 1 Hz to 6 Hz. Then, tissues are treated with an exercise regimen for three days, concluding at 10 days of electrical stimulation.

FIGS. 8A-8B shows the effect of the electrical stimulation regimen on tissue contractile force. FIG. 8A shows mean contractile force of stimulated tissues (ES+) after the frequency ramp-up regimen (day 12; N>4) and after 3 days of the exercise regimen (day 15, N=4) compared to non-stimulated tissues (ES−). FIG. 8B shows mean contractile force of ES+ and ES− tissues in response to isoproterenol (day 15, N=4).

FIG. 9A shows immunofluorescent images of ES− tissue structure (α-actinin, green; collagen, red; DAPI, blue). FIG. 9B shows immunofluorescent images of ES+ tissue structure (α-actinin, green; collagen, red; DAPI, blue). ES+ tissues present robust alignment of sarcomeres.

FIG. 10A shows mean tissue contractile force under standard culture conditions over time (N≥5, p<0.001). FIG. 10B shows mean contractile force in the presence of ascorbic acid over time (N≥5, p<0.05). FIG. 10C shows mean contractile force of WT and $403^{+/-}$ tissues +/− AA at day 14 (N≥9, p<0.001).

FIG. 11A shows immunofluorescent images of WT tissues stained for collagen I. FIG. 11B shows $403^{+/-}$ tissues stained for collagen I. FIG. 11C shows mean intensity of the collagen images.

FIGS. 13A-13D show perspective views of the exemplary system shown in FIG. 12.

FIG. 14A is a perspective view of a resulting positive mold 300. Other mold fabrication methods can be used. Polydimethylsiloxane (PDMS) is used to cast an exemplary final positive mold 310 as shown in FIG. 14B for forming the support base devices such as the device 110 in FIG. 12 for generating cardiac tissues.

DETAILED DESCRIPTION

Figure 1C:
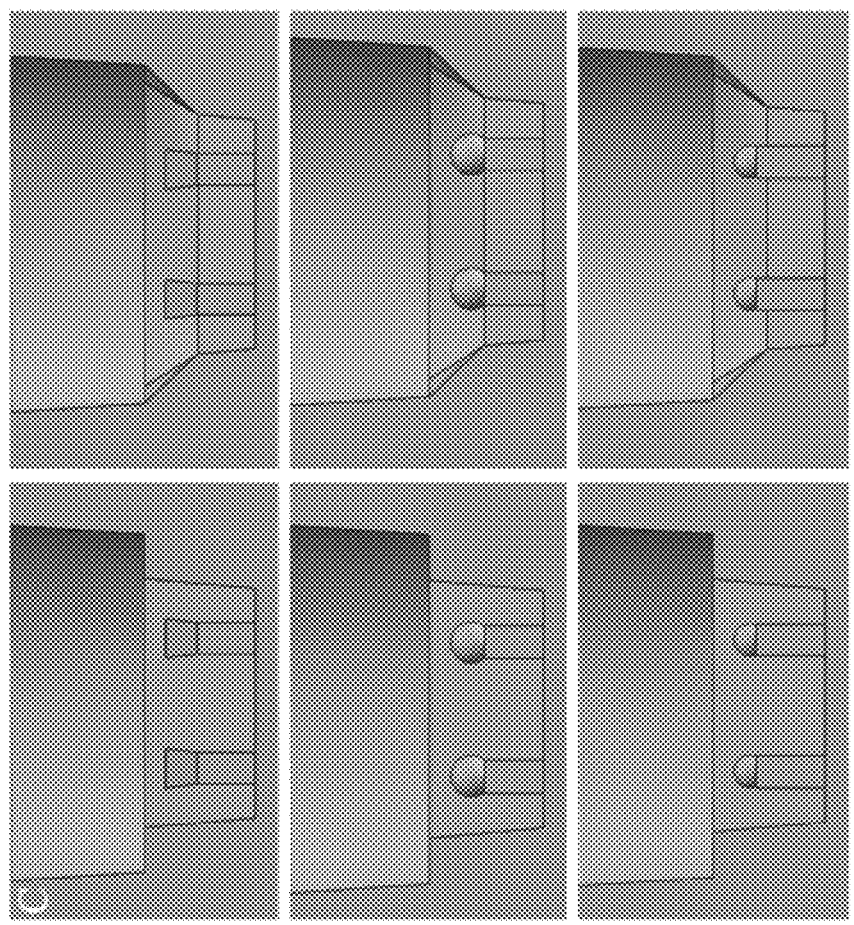
FIGS. 1A-1C show a schematic of platform prototype mold.

Briefly, the methods described herein relate, in part, to the discovery that a high throughput 3D tissue system can better recapitulate the in vivo microenvironment of cardiac tissue and the system can prolong cell viability, mature cardiomyocytes, and allow for the recapitulation of cardiac diseases. The processing steps described herein allow for a facile fabrication of a device (see e.g., FIG. 3) that allows for the culturing, maturation, and monitoring of phenotypic characteristics of cardiac tissues such as contractile function, structure, and electrophysiology.

Definitions:

As used herein, "3-dimensional (3D) cardiac tissue" refers to cardiac tissue that has more than one layer of cardiac cells in any given plane. A 3-dimensional cardiac tissue is not a monolayer or laminar in structure. Rather, 3-dimensional tissues possess a shape with a larger volume compared with monolayer tissues. For the purposes of the application, such 3D cardiac tissues are tissues of a thickness or dimension that permits the tissue to overcome the diffusion limit of the cells but also of a thickness or dimension that provides sufficient strength to the tissues to prevent tearing, thereby permitting increased longevity and maturation of the tissue. In some embodiments, the dimensions of the tissue are in the range of 500 µm to $1\times10^8$ µm (i.e., 1 cm), inclusive. In other embodiments, the dimension of the tissue is in the range of 600 µm to $1\times10^8$ µm, 650 µm to $1\times10^8$ µm, 700 µm to $1\times10^8$ µm, 750 µm to $1\times10^8$ µm, 800 to µm to $1\times10^8$ µm, 850 to µm to $1\times10^8$ µm, 900 µm to $1\times10^8$ µm, 1000 µm to $1\times10^8$ µm, 1500 µm to $1\times10^8$ µm, 2000 µm to $1\times10^8$ µm, 3000 µm to $1\times10^8$ µm, 4000 µm to $1\times10^8$ µm, 5000 µm to $1\times10^8$ µm, 6000 µm to $1\times10^8$ µm, 7000 µm to $1\times10^8$ µm, 8000 µm, to $1\times10^8$ µm, 9000 µm to $1\times10^8$ $1\times10^4$ µm to $1\times10^8$ $1\times10^5$ µm to $1\times10^8$ $1\times10^6$ µm to $1\times10^8$ $1\times10^7$ µm to $1\times10^8$ µm, 500 µm to $1\times10^7$ µm, 500 µm to $1\times10^6$ µm, 500 µm to $1\times10^5$ µm, 500 µm to $1\times10^4$ µm, 500 µm to 9000 µm, 500 µm to 8000 µm, 500 µm to 7000 µm, 500 µm to 6000 µm, 500 µm to 5000 µm, 500 µm to 4000 µm, 500 µm to 3000 µm, 500 µm to 2000 µm, 500 µm to 1000 µm, 500 µm to 900 µm, 500 µm to 800 µm, 500 µm to 750 µm, 500 µm to 700 µm, 500 µm to 600 µm, 600 µm to 4000 µm, 700 µm to 4000 µm, 800 µm to 4000 µm, 900 µm to 4000 µm, 1000 µm to 4000 µm, 2000 µm to 4000 µm, 3000 µm to 4000 µm, 900 µm to 3500 µm, 9000 µm to 3000 µm, 1000 µm to 3000 µm, 1000 µm to 2000 µm, 2000 µm to 3000 µm, or any integer there between.

As used herein, a "support base," refers to a support (also referred to as an insoluble support or solid support base) refers to any solid or semisolid or insoluble support to which a components of the device as described here are attached. The solid support base can be made of any solid material. Such materials include any materials that are used as supports for chemical and biological use and analyses, such as, but are not limited to: cured polydimethylsiloxane (PDMS), polyurethane (PU), or poly(ethylene glycol) (PEG), cured gelatin, acrylic, COC-polymers, polystyrene, polycarbonate, polypropylene, nylon, glass, dextran, chitin, pumice, agarose, metal, polysaccharides, dendrimers, polyacrylamide, silicon, rubber, and other materials.

As used herein, the term "pillar" refers to a vertical structure or support for the cardiac tissue described herein. The pillar can be any shape. The pillar is flexible to permit deflection of the pillar for video imaging and analysis. The pillar acts as the support for the heads that attach directly to the cardiomyocytes as described herein. The distance between two pillars in the device or system described herein can be at least 0.6 millimeters, at least 0.7 millimeters, at least 0.8 millimeters, at least 0.9 millimeters, at least 1.0 millimeters, at least 1.1 millimeters, at least 1.2 millimeters, at least 1.3 millimeters, at least 1.4 millimeters, at least 1.5 millimeters, at least 1.6 millimeters, at least 1.7 millimeters, at least 1.8 millimeters, at least 1.9 millimeters, at least 2.0 millimeters, at least 2.5 millimeters, at least 3.0 millimeters or more. In some embodiments, the distance between the at least two pillars in the device or system described herein is within the range of 0.6-4.0 mm, inclusive; in other embodiments, the distance is within the range of 0.7-4.0 mm, 0.8-4 mm, 0.9-4 mm, 1.0-4.0 mm, 1.2-4.0 mm, 1.4-4.0mm, 1.6-4.0 mm, 1.8-4.0 mm, 2.0-4.0mm, 2.2-4.0 mm, 2.4-4.0 mm, 2.6-4.0mm, 2.8-4.0 mm, 3.0-4.0 mm, 3.2-4.0 mm, 3.4-4.0 mm, 3.6-4.0 mm, 3.8-4.0 mm, 0.6-08 mm, 0.6-1.0 mm, 0.6-1.2 mm, 0.6-1.4 mm, 0.6-1.6 mm, 0.6-1.8 mm, 0.6-2.0 mm, 0.6-2.2 mm, 0.6-2.4 mm, 0.6-2.6 mm, 0.6-2.8 mm, 0.6-3.0 mm, 0.6-3.2 mm, 0.6-3.4 mm, 0.6-3.6 mm, 0.6-3.8 mm, 0.8-3.2 mm, 1.0-3.0 mm, 2.0-3.0 mm, 2.5-3.0 mm, 2.5-3.5 mm, 1.0-1.5 mm, 1.0-2.0 mm, 2.0-2.5 mm, or any range there between.

As used herein, the term "chamber" refers to part of a well that is in open or closed formation on the system or device. In most instances, the chamber is a size smaller than the well or resides inside of the well.

As used herein, the terms "head" or "cap" or "head on top of each pillar" are used interchangeably to refer to the part of the system or device that allows for attachment or contact with the cells, cardiac tissues, or cardiomyocytes. Generally, a head or cap is positioned at the top of each flexible pillar in the device.

As used herein, the term "sticky coating" refers to any coating that is added to the head or cap of the system and device described herein. The sticky coating can comprise a gel or adhesive that permits adhesion of the cells or cardiomyocytes to the head of the system or device. Non-limiting examples of sticky coating include plasma, poly-lysine, glutaraldehyde, gelatin, extracellular matrix proteins and hydrogels (e.g., Matrigel®), or a polarized chemical, metal, ion, etc. As the cellular membrane phospholipids are typically positively charged on the outside and negatively charged on the inside, it is contemplated that the sticky coating can be a negatively charged or a combination of positive and negative charges that allow for cell adhesion.

As used herein, the term "mature phenotype" or "maturing cardiomyocytes" when applied to cardiomyocytes refers to a phenotype similar to adult cardiomyocytes and at a minimum does not comprise at least one feature of a fetal cardiomyocyte. In some embodiments, markers which indicate increased maturity of a cardiomyocyte include, but are not limited to, an increased expression of α-actinin, c-TnT and/or b-MHC, increased anisotropy, increased cellular alignment, anisotropic arrangement of gap junctions & cadherins between cells, increased T-tubule formation and caveolin expression, wherein the increase is relative to that marker in another population of the same cardiomyocytes. In some embodiments, the matured cardiomyocytes have an increased conversion of ssTnI to ctTnI, N2BA to N2B, and appropriate increase or decrease in expression of ion channels as expressed in adult cardiac tissue (voltage gated K+ channels, Na+ channels, voltage dependent $Ca^{2+}$ channels, cyclic nucleotide dependent K+ channels, and other ion channels). In some embodiments, the matured cardiomyocytes have an increased contraction at single cell and multicellular level measured by contraction mapping aided by microscopy, increased strength or force of contraction. In some embodiments, the matured cardiomyocytes have an increased cell-cell electrical conductivity, increased syncytial nature of 3D in vitro culture allowing electrical action potential to propagate from one point to another, increased wave speed and decreased excitation threshold, increased $Ca^{2+}$ transient current.

As used herein, a "stem cell-derived cardiomyocyte" is a cardiomyocyte differentiated from a stem cell in culture, i.e., in vitro. Thus, while cardiomyocytes in vivo are ultimately derived from a stem cell, i.e., during development of a tissue or organism, a stem cell-derived cardiomyocyte as described herein has been created by in vitro differentiation from a stem cell. As used herein, a cell differentiated in vitro from a stem cell, e.g., an induced pluripotent stem (iPS) cell or embryonic stem cell ("ES cell" or "ESC"), is a "stem-cell derived cardiomyocyte" if it has, at a minimum, spontaneous beating or contraction, and expression of cardiac troponin T (cTnT). Methods for differentiating stem cells in vitro to cardiomyocytes are known in the art and described elsewhere herein.

The terms "stem cell" or "undifferentiated cell" as used herein, refer to a cell in an undifferentiated or partially differentiated state that has the property of self-renewal and has the developmental potential to differentiate into multiple cell types, without a specific implied meaning regarding developmental potential (i.e., totipotent, pluripotent, multipotent, etc.). A stem cell is capable of proliferation and giving rise to more such stem cells while maintaining its developmental potential. In theory, self-renewal can occur by either of two major mechanisms. Stem cells can divide asymmetrically, which is known as obligatory asymmetrical differentiation, with one daughter cell retaining the developmental potential of the parent stem cell and the other daughter cell expressing some distinct other specific function, phenotype and/or developmental potential from the parent cell. The daughter cells themselves can be induced to proliferate and produce progeny that subsequently differentiate into one or more mature cell types, while also potentially retaining one or more cells with parental developmental potential. A differentiated cell can derive from a multipotent cell, which itself is derived from a multipotent cell, and so on. While each of these multipotent cells can be considered stem cells, the range of cell types each such stem cell can give rise to, i.e., their developmental potential, can vary considerably. Alternatively, some of the stem cells in a population can divide symmetrically into two stem cells, known as stochastic differentiation, thus maintaining some stem cells in the population as a whole, while other cells in the population give rise to differentiated progeny only. Accordingly, the term "stem cell" refers to any subset of cells that have the developmental potential, under particular circumstances, to differentiate to a more specialized or differentiated phenotype, and which retain the capacity, under certain circumstances, to proliferate without substantially differentiating. In some embodiments, the term stem cell refers generally to a naturally occurring parent cell whose descendants (progeny cells) specialize, often in different directions, by differentiation, e.g., by acquiring completely individual characters, as occurs in progressive diversification of embryonic cells and tissues. Some differentiated cells also have the capacity to give rise to cells of greater developmental potential. Such capacity can be natural or can be induced artificially upon treatment with various factors. Cells that begin as stem cells might proceed toward a differentiated phenotype, but then can be induced to "reverse" and re-express the stem cell phenotype, a term often referred to as "dedifferentiation" or "reprogramming" or "retrodifferentiation" by persons of ordinary skill in the art, and as used herein.

In the context of cell ontogeny, the term "differentiate", or "differentiating" is a relative term that indicates a "differentiated cell" is a cell that has progressed further down a developmental pathway than its precursor cell. Thus in some embodiments, a stem cell as the term is defined herein, can differentiate to lineage-restricted precursor cells (such as a human cardiac progenitor cell or mid-primitive streak cardiogenic mesoderm progenitor cell), which in turn can differentiate into other types of precursor cells further down the pathway (such as a tissue specific precursor, such as a cardiomyocyte precursor), and then to an end-stage differentiated cell, which plays a characteristic role in a certain tissue type, and can or can not retain the capacity to proliferate further. Methods for in vitro differentiation of stem cells to cardiomyocytes are known in the art and/or described herein below. The differentiation status of a cell is generally determined by one or more of characteristic gene or marker expression pattern, metabolic activit(ies), and morphology.

The term "pluripotent" as used herein refers to a cell with the capacity, under different conditions, to differentiate to cell types characteristic of all three germ cell layers (endoderm, mesoderm and ectoderm). Pluripotent cells are characterized primarily by their ability to differentiate to all three germ layers, using, for example, a nude mouse and teratoma formation assay. Pluripotency is also evidenced by the expression of embryonic stem (ES) cell markers, although the preferred test for pluripotency is the demonstration of the capacity to differentiate into cells of each of the three germ layers.

The term "reprogramming" as used herein refers to a process that alters or reverses the differentiation state of a differentiated cell (e.g. a somatic cell). Stated another way, reprogramming refers to a process of driving the differentiation of a cell backwards to a more undifferentiated or more primitive type of cell. The cell to be reprogrammed can be either partially or terminally differentiated prior to reprogramming. In some embodiments, reprogramming encompasses complete reversion of the differentiation state of a differentiated cell (e.g., a somatic cell) to a pluripotent state. In some embodiments, reprogramming also encompasses partial reversion of the differentiation state of a differentiated cell (e.g., a somatic cell) to a multipotent state. In some embodiments, reprogramming encompasses complete or partial reversion of the differentiation state of a differentiated cell (e.g., a somatic cell) to an undifferentiated cell. Reprogramming also encompasses partial reversion of the differentiation state of a somatic cell to a state that renders the cell more susceptible to complete reprogramming to a pluripotent state when subjected to additional manipulations.

Reprogramming involves alteration, e.g., reversal, of at least some of the heritable patterns of nucleic acid modification (e.g., methylation), chromatin condensation, epigenetic changes, genomic imprinting, etc., that occur during cellular differentiation as a zygote develops into an adult.

As used herein, the terms "induced pluripotent stem cell (iPSC), "hPSC cell" and "human pluripotent stem cell" are used interchangeably herein and refer to a pluripotent cell artificially derived from a differentiated somatic cell. iPSC cells are capable of self-renewal and differentiation into cell fate-committed stem cells, including cells of the cardiac lineages, as well as various types of mature cells.

The term "derived from," used in reference to a stem cell means the stem cell was generated by reprogramming of a differentiated cell to a stem cell phenotype. The term "derived from," used in reference to a differentiated cell means the cell is the result of differentiation, e.g., in vitro differentiation, of a stem cell. As used herein, "iPSC-CMs" or "induced pluripotent stem cell-derived cardiomyocytes" are used interchangeably to refer to cardiomyocytes derived from an induced pluripotent stem cell.

The term "agent," as used herein, means any compound or substance including, but not limited to, a small molecule, nucleic acid, polypeptide, peptide, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogue, protein, antibody, peptide, aptamer, oligomer of nucleotides, amino acids, or carbohydrates including without limitation proteins, oligonucleotides, ribozymes, DNAzymes, glycoproteins, siRNAs, lipoproteins and modifications and combinations thereof. In certain embodiments, agents are small molecules comprising or consisting of chemical moieties including unsubstituted or substituted alkyl, aromatic, or heterocyclyl moieties including macrolides, leptomycins and related natural products or analogues thereof. Agents can be known to have a desired activity and/or property, or can be selected from a library of diverse compounds. Typically, an agent will have or is expected to have biological activity in a cell or subject.

As used herein, the term "small molecule" refers to a chemical agent which can include an organic or inorganic compound (including heterorganic and organometallic compounds) having a molecular weight less than about 5,000 grams per mole, an organic or inorganic compound having a molecular weight less than about 1,000 grams per mole, an organic or inorganic compound having a molecular weight less than about 500 grams per mole, and salts, esters, and other pharmaceutically acceptable forms of such compounds.

The term "cardiotoxicity" refers to the property of a drug or agent that inhibits or impairs one or more of: cardiomyocyte viability, structure or function, including but not limited to contraction, biopotential or electrophysiological properties or rhythm thereof, or gene expression necessary for proper cardiac function. Cardiotoxicity can be assessed by measuring phenotypic characteristics such as a biopotential, contractility, cardiomyocyte markers, cell viability, bioenergetics or metabolism, and mechanical properties of the cardiomyocytes or cardiac tissues. Methods of measuring and identifying cardiotoxicity are known in the art. For example, see US20130230881A1; US20050138675A1; Roden D M. *J. Physiol.* (2016); Crumb et al. *J. Pharmacol Toxicol Meth* (2016); Terstappen et al. *Future Med Chem.* (2010); Blinova et al. *Cell Reports* (2018); which are incorporated herein by reference in their entirety.

As described herein, a "genetically modified cell" is a cell which either carries a heterologous genetic material or construct, or which comprises a genome that has been manipulated, e.g., by mutation, including but not limited to site-directed mutation. The introduction of a heterologous genetic material generally results in a change in gene or protein expression relative to an un-modified cell. Introduction of RNA can transiently promote expression of a foreign or heterologous product, as can the introduction of a vector that does not integrate or replicate within the cell. Introduction of a construct that integrates into a cell's genome or replicates with the cell's nucleic acid will be more stable through successive cell divisions. In one embodiment, genetic modification is in addition to or separate from the introduction of a construct or constructs that reprogram a somatic cell to a stem cell phenotype, such as an iPS cell phenotype. Genetic modifications are known to those of skill in the art and can include, but are not limited to, the introduction of genetic material via viral vector or modification using CRISPR/Cas or similar system for site specific recombination.

As used herein, the term "contacting" when used in reference to a cell, encompasses both introducing an agent, surface, hormone, etc. to the cell in a manner that permits physical contact of the cell with the agent, surface, hormone etc., and introducing an element, such as a genetic construct or vector, that permits the expression of an agent, such as a miRNA, polypeptide, or other expression product in the cell. It should be understood that a cell genetically modified to express an agent, is "contacted" with the agent, as are the cell's progeny that express the agent.

As used herein, the term "delivering" when used in reference to a cell suspension, encompasses contacting the system or device, preferably the well or pillars, with the desired cells and/or appropriate culture medium to generate the cardiac tissues. The delivering can be accomplished for example, with a pipette, a syringe, or a capillary tube.

The term "functional assay" as used herein refers to a test which assesses the properties of a cell, such as a cell's gene expression, metabolism, developmental state or maturity, among others, by measurement of a cellular activity. Functional assays include, for example, measurement of cell viability (e.g., by dye exclusion, nutrient uptake and/or conversion, metabolite production, etc.), measurement of electrical potential or other electrophysiological property, measurement of contraction strength, rate or rhythm, measurement of mitochondrial function, etc.

The term "disease model" as used herein refers to an animal or cell culture system that recapitulates one or more aspects of a human disease. Cell culture models of human disease can include cells from a human subject with the disease, or human or other cells modified to express or interfere with expression of one or more disease-related genes. As but one example, iPSCs derived from a human with hypertrophic cardiomyopathy or from a cell comprising a R403Q mutation associated with hypertrophic cardiomyopathy, when differentiated to cardiomyocytes and treated as described herein to promote maturity can provide a cell culture model of hypertrophic cardiomyopathy.

As used herein, the term "electrical stimulation" refers to an electrical stimulus that is applied to the tissue described herein in vitro (during cultivation and formation of the tissue). The electrical stimulation applied to the cardiac tissue is such that it resembles the electrical stimulation received by a specific native tissue in vivo or is a particular regimen of stimulation frequencies that permit viability and/or maturation of the cardiomyocytes. For example, cardiac tissue can be cultured in the presence of an electrical stimulation that mimics the electrical stimulation received by a cardiac muscle tissue in vivo or be a specific frequency that mimics disease states, exercise, stress, or is a frequency for a desired phenotype of the cardiac tissue. Without any limitation, the user of the system or device described herein can determine the appropriate settings for electrical stimulation.

As used herein, a "cardiac disease or disorder" is one that adversely affects normal muscle or electrical function as either a primary effect of the disease or disorder or as a result of the disease or disorder's effect on other systems that impact cardiac muscle or electrical function. Cardiac diseases or disorders necessarily impact the proper function of the heart muscle, and include, but are not limited to cardiac arrhythmias, cardiomyopathies (e.g., hypertrophic and dilated), long QT syndromes, arrhythmogenic right ventricular dysplasia (ARVD), catecholaminergic polymorphic ventricular tachycardia (CPVT), or Barth syndrome. Duchenne muscular dystrophy affects cardiac muscle function in late stages.

The term "contractility" as used herein and refers to the behavior of muscle cells, including cardiomyocytes, whereby they contract, either alone or, more often, in groups (e.g., synchronized contraction). Contractility can be measured in terms of the rate of contraction or relaxation and, for example, the force of contraction. The contractility of a plurality of cells is measured by biophysical and biomechanical properties of the force transmission. Contractility is measured using phase-contrast microscopy of monolayers or multiple-layers of said cardiac cells and computational analysis, which is calibrated with direct force measurement using force transducers.

As used herein, the term "co-culturing" or "co-culture" refers to the maintenance and/or growth of more than one cell type in the system or device as described herein. For example, the cardiac tissue can contain other cell types in the mixture or suspension upon delivering the cell suspension. Alternatively, the cardiac tissue can be co-cultured with any other cell type added separately or mixed into the suspension. For example, co-culturing cells can be used to evaluate the effect on at least one phenotypic characteristic of the cardiac tissue in response to the presence of another cell type, improve cardiac tissue viability, improve cardiac tissue function, or create a disease model. Non-limiting examples of cells that can be co-cultured with cardiomyocytes or stem cells can include stromal cells, mesenchymal stem cells, vascular endothelial cells, fibroblasts, neurons, and the like. Stromal cells generally can differentiate into a variety of cells types and serve as connective tissue cells that form the supportive structure in which the functional cells of the tissue reside.

The term "statistically significant" or "significantly" refers to statistical significance and generally means a change of two standard deviations (2SD) relative to a reference. The term refers to statistical evidence that there is a difference. It is defined as the probability of making a decision to reject the null hypothesis when the null hypothesis is actually true.

The terms "decrease", "reduced", "reduction", or "inhibit" are all used herein to mean a decrease or lessening of a property, level, or other parameter by a statistically significant amount. In some embodiments, "reduce," "reduction" or "decrease" or "inhibit" typically means a decrease by at least 10% as compared to a reference level and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99% , or more. As used herein, "reduction" or "inhibition" does not encompass a complete inhibition or reduction as compared to a reference level. "Complete inhibition" is a 100% inhibition as compared to a reference level.

The terms "increased" ,"increase" or "enhance" or "activate" are all used herein to generally mean an increase of a property, level, or other parameter by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

As used herein, "around", "about", "substantially" or "approximately" shall generally mean within 20 percent, preferably within 10 percent, and more preferably within 5 percent of a given value or range. Numerical quantities given herein are approximate, meaning that the terms "around", "about", "substantially" or "approximately" can be inferred if not expressly stated.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Devices and Systems for Generating 3-dimensional (3D) Cardiac Tissues

Figure 12:
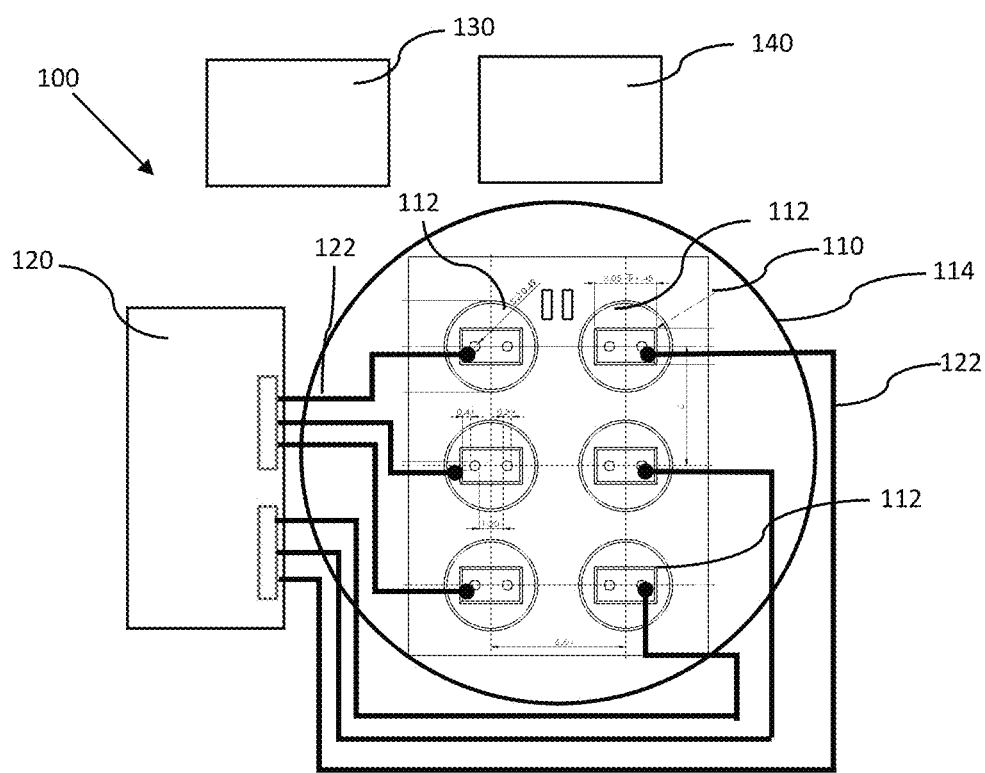
FIG. 12 shows a system 100 for generating 3-dimensional (3D) cardiac tissues from pluripotent stem cell derived cardiomyocytes (iPSC-CMs) based on the processes described below.

FIG. 12 shows an exemplary system 100, which includes a rectangular solid support base 110. The base 110 includes several wells 112 for generating the tissue from inserted cells. As shown in FIG. 12 and described in the working Examples, each of the wells 112 includes a lower chamber and an upper chamber. The lower chamber includes at least two pillars. Cells are inserted in the lower chamber and the cardiac tissue is generated across the pillars in each of the wells 112. The base 110 is adhered to a petri dish 114. In this example, the petri dish is 35 mm in diameter the combined petri dish 114 and support base 110 form the final device for cardiac tissue generation. In this example, the support base 110 and features of the wells 112 are formed from polydimethylsiloxane (PDMS).

The system 100 also includes a culture stimulator 120, an optical tracking instrument 130, and an amplifier instrument 140 (see e.g., FIG. 12). The culture stimulator 120 is used for electrical stimulation of cell cultures. In this example, the culture stimulator 120 is an IonOptix C-Pace EP Culture Pacer, but other similar stimulators can be used. The stimulator 120 includes a set of electrodes 122 that are inserted in the wells 112 to provide electrical signals to stimulate tissue generation. The optical tracking instrument 130 measures contractile function of the tissues generated in the wells 112. The amplifier instrument 140 measures the electrical function of the tissues generated in the wells 112.

Prolonged electrical stimulation increases the maturation of iPSC-CMs in the wells 112. Electrical stimulation increases cell alignment and structural organization, enhances $Ca^{2+}$ handling, and improves the electrophysiological properties of cardiomyocytes in the wells 112. A frequency ramp-up regimen of iPSC-CM tissues over the course of 7 days exhibits increased electrophysiological properties, such as lower excitation threshold and increased conduction velocity, as well as improving sarcomeric organization, producing constructs that present a more adult-like phenotype.

FIGS. 13A shows a perspective view of a system depicted in FIG. 12 having a combined solid support base 110 and petri dish 114. FIG. 13B is a perspective view of the solid support base 110 and wells 112. FIG. 13C is a close-up perspective view of one of the wells 112. FIG. 13D is a cross section view of one of the wells 112. The solid support base 110 is roughly rectangular in shape and includes a top surface 210. The wells 112 are formed in the top surface 210. Any number of wells can be formed in the top surface 210. For example, the number of wells can be between 1 and 96 wells. In some embodiments, the number of wells can be configured to correspond to standard cell culture dishes, such as e.g., 6 well, 12 wells, 24 wells, or 96 wells.

The well 112 includes a cylindrical upper chamber 220, that has a circular outer wall 222, and a bottom surface 224. In this example, the circular outer wall 222 is at a slight incline. The circular outer wall 222 therefore defines the upper chamber 220 extending from the top surface 210 to the bottom surface 224. A lower chamber 230 is cut out in the bottom surface 224 of the upper chamber 220. The lower chamber 230 is a rectangular shape in this example. The lower chamber 230 includes two opposite longer walls 232 and 234, and two opposite shorter walls 236 and 238. The walls 232, 234, 236, and 238 are inclined and extend from the bottom surface 224 of the upper chamber 220 to a bottom surface 240 of the lower chamber 230. Thus, the walls 232, 234, 236, 238 define the volume of the lower chamber 230. It is to be understood that the upper and lower chambers 220 and 230 can have different shapes other than a rectangle or a cylinder.

Two pillars 250 and 252 with roughly square lateral cross sections extend from the bottom surface 234. The pillars 250 and 252 have one end attached to the bottom surface 240 and opposite ends that are roughly level with the bottom surface 224 of the upper chamber 220. Thus, each of the pillars 250 and 252 extend to the height of the lower chamber 230. As will be explained below, the cardiac tissue is generated between the pillars 250 and 252 from the cells inserted in the upper and lower chambers 220 and 230. Although two pillars are shown in FIGS. 13A-13D, it is to be understood that more pillars can be used (e.g., at least 3, at least 4, at least 5, at least 6, at least 7, at least 8, at least 9, at least 10, or more).

The pillars 250 and 252 are flexible and permit contraction of the cells that are inserted in the chambers 220 and 230. In this example, the pillars 250 and 252 are 0.01 to 2.0 millimeters (mm) in height. The spring constant of the pillars 250 and 252 is within the range of 0.05-15 micronewtons/micrometer ($\mu$N/$\mu$m). The spring constant of the pillars 250 and 252 can be changed by changing the height of the pillars 250 and 252. The pillars simulate static mechanical loading on the tissue, so pillars that are too stiff for the tissue to displace adequately predispose the system to induce increased afterload. For example, when the pillars are fabricated by a 1:10 PDMS ratio, a pillar of 1.1 mm height has a spring constant of 8.86 $\mu$N/$\mu$m, a pillar of 1.2 mm height has a spring constant of 6.74 $\mu$N/$\mu$m, and a pillar of 1.5 mm height has a spring constant of 3.35 $\mu$N/$\mu$m. When the pillars are fabricated by a 1:20 PDMS ratio, a pillar of 1.1 mm height has a spring constant of 3.21 $\mu$N/$\mu$m, a pillar of 1.2 mm height has a spring constant of 2.68 $\mu$N/$\mu$m, and a pillar of 1.5 mm height has a spring constant of 1.99 $\mu$N/$\mu$m.

Each of the pillars 250 and 252 have a respective head or cap 254 and 256 that each protrude into the upper chamber 220. In this example, the heads 254 and 256 are spherically shaped and overhang the lateral area of the pillars 250 and 252. In this example, the pillars 250 and 252 have a width of 400 $\mu$m and the caps 250 and 252 overhang the pillars 250 and 252 by 50 $\mu$m. Alternatively, the heads 254 and 256 can have different shapes and dimensions as will be explained below. The spherical geometry of the heads 254 and 256 permits even distribution of stress on the tissue, thus decreasing concentrations of stress at specific points of the tissue which could compromise the tissue's structural integrity.

Figure 14A:
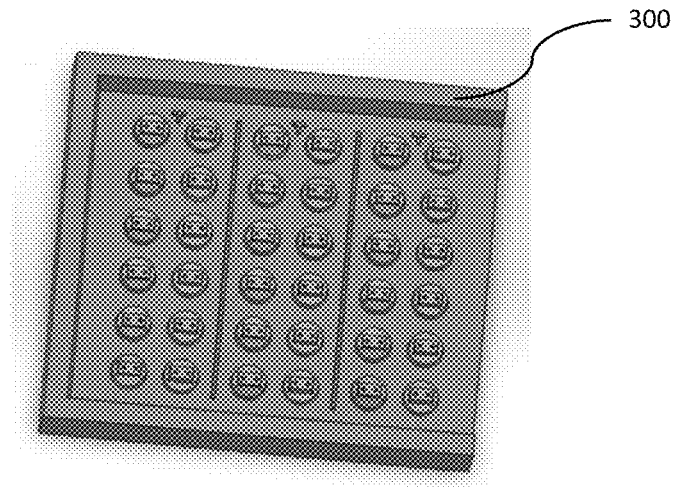
FIGS. 14A-14B depicts the production of a support base 110 by a molding process. An exemplary positive mold is 3D printed using stereolithography.

The support base 110 can be produced by a molding process. A positive mold is 3D printed using stereolithography. FIG. 14A is a perspective view of a resulting positive mold 300. Other mold fabrication methods can be used. Polydimethylsiloxane (PDMS) or any curable polymer with tunable elastic moduli can be used to cast a final positive mold 310 as shown in FIG. 14B for forming the support base devices such as the device 110 in FIG. 12 for generating cardiac tissues.

Figure 14B:
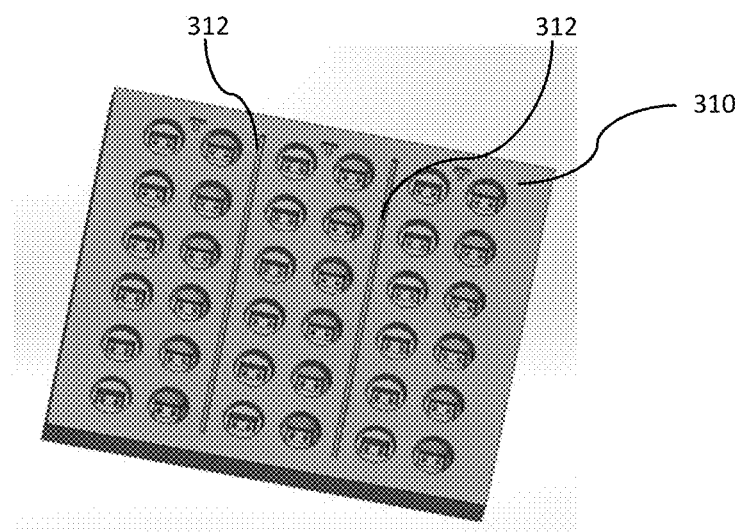

The PDMS is prepared at a 1:10 ratio and poured onto the negative 3D printed mold 300 in FIG. 14. The PDMS can be made at other ratios such as 1:5 or 1:20. The PDMS is cured at 60° C. for 24 hours. The PDMS positive mold 310 is then removed from the negative mold 300 and cut into three strips along the indicated lines 312 and 314 in FIG. 14B, creating six base devices similar to the base 110 in FIG. 12. Generally, each device is attached to a 35 mm or 60 mm petri dish using PDMS and cured at 60° C. for 24 hours. The devices are UV sterilized for 15 minutes prior to seeding.

As explained above, different shapes can be used for the upper and lower chambers in the wells. Further different head geometries can be used for the heads 254 and 256 in FIGS. 13A-13D.

FIGS. 15A-15E show cross-sections of alternate head geometries for the head 254 and 256 on the pillars 250 and 252, and upper and lower chamber shapes for the upper and lower chambers 220 and 230.

Figure 15A:
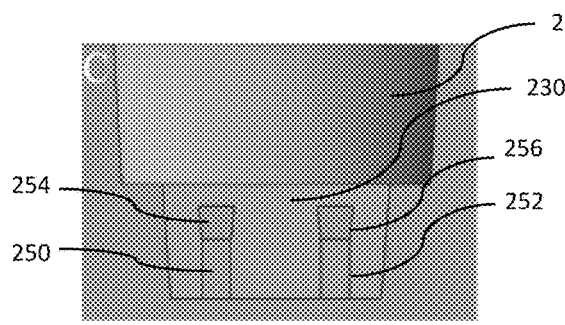
FIGS. 15A-15E show cross-sections of alternate cap geometries for the caps 254 and 256 on the pillars 250 and 252, and upper and lower chamber shapes for the upper and lower chambers 220 and 230.
Figure 15B:
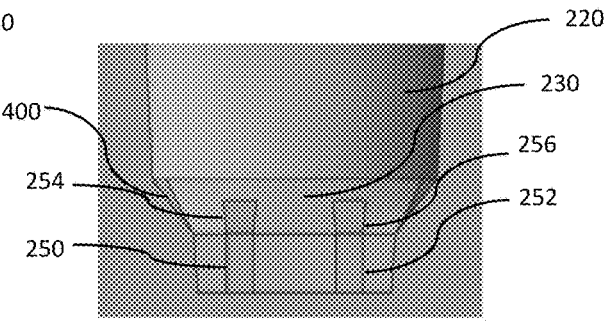
Figure 15C:
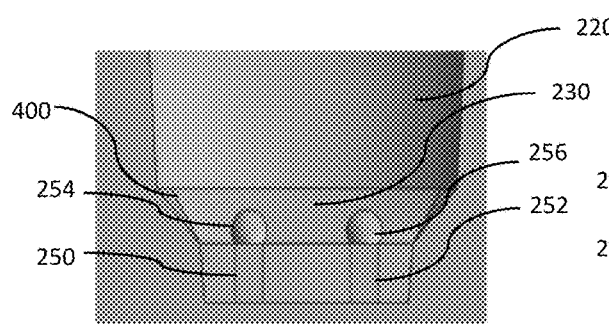
Figure 15D:
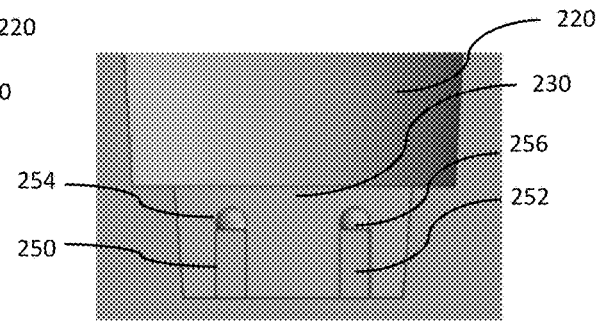
Figure 15E:
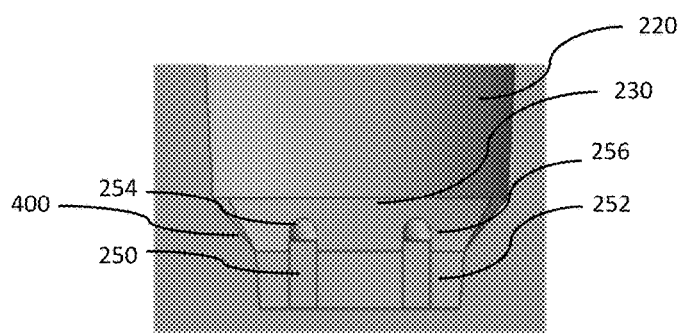

FIG. 15A shows an alternative head geometry for the heads 254 and 256. In this example, the heads 254 and 256 have a rectangular shape. FIG. 15B shows the rectangular shape of the heads 254 and 256 in combination with a different transition between the upper chamber 120 and the lower chamber 130. In this example, a tapered wall 400 extends on the bottom part of the upper chamber 120. FIG. 15C shows the heads 254 and 256 having a spherical shape that overhang the pillars 250 and 252 in conjunction with the different upper chamber 120 with the tapered wall 400. FIG. 15D shows the heads 254 and 256 with a spherical shape that does not overhang the pillars 250 and 252 with the upper chamber 120 and lower chamber 130 shaped similarly to that shown in FIGS. 13A-13B. FIG. 15E shows the heads 254 and 256 with a spherical shape that does not overhang the pillars 250 and 252 with the upper chamber 120 and lower chamber 130 having the transition taped wall 400.

Fabrication of Devices and Systems

In one aspect, described herein is a method of making a device or system for engineering 3D cardiac tissues.

The devices and systems described herein can be fabricated using a 3D printed negative mold. The mold can be designed using computer software (e.g., SolidWorks, AutoCAD) to the desired dimensions or as described herein. The well, head, and pillar geometries and heights can be designed as desired by one of skill in the art. The mold can be generated by direct-ink writing or stereolithography using a 3D printer (e.g., Protolabs). The mold can be 3D printed to the given geometries that match what is desired for the solid support base. Methods of 3D printing are well known in the art. See, for example, U.S. Pat. Nos. 7,291,002B2; 6,164,850A; US20160089821A1; which are incorporated herein by reference in their entireties.

The advantage of the present methods of device fabrication is that 3D printing a mold can reduce processing time and cost compared to traditional soft photolithography methods. Soft photolithography methods require the use of harsh chemicals, clean room facilities, are costly, time consuming, and require silicon wafers or masks to create the desired product. The 3D printed mold allows for a dramatic reduction in processing time while maintaining a high degree of resolution. Depending on the 3D printer, the resolution of features in the mold can be 0.2 millimeters, 0.3 millimeters or less, 0.4 millimeters or less, 0.5 millimeters or less, 0.6 millimeters or less, 0.7 millimeters or less, 0.8 millimeters or less, 0.9 millimeters or less, 1 millimeter or less.

Following printing of the final negative mold, a curable polymer (e.g., Polydimethylsiloxane (PDMS)) or elastomer can be cast over the mold for generating the 3D cardiac tissues. Any suitable biogenic and/or non-biogenic polymer can be used to fabricate the system or device described herein. Exemplary polymers for use in the devices, constructs, and methods described herein can be biocompatible or non-biocompatible, synthetic or natural and those such as those that are synthetically designed to have shear induced unfolding. Non-limiting examples of polymers and elastomers than can be used include polydimethylsiloxane (PDMS), polyurethanes (PU), silicone-urethane copolymers, carbonate-urethane copolymers, polyisoprene, polybutadiene, copolymer of polystyrene and polybutadiene, chloroprene rubber, polyacrylic rubber (ACM, ABR), fluorosilicone rubber (FVMQ), fluoroelastomers, perfluoroelastomers, tetrafluoro ethylene/propylene rubbers (FEPM) and ethylene vinyl acetate (EVA), hydrogels such as gelatin, alginate, agarose, polyethylene glycol (PEG), polyacrylamide gels, poly(N-isopropylacrylamide), pHEMA, collagen, fibrin, and dextran, and porous and nanostructured scaffolds based on natural and synthetic polymers, such as, collagens, elastins, polysaccharides, and other extracellular matrix proteins, elastin-like peptides, polyhydroxyalkanoates, poly (glycerol-sebecate), polylactic acid, polyglycolic acid, and poly lactic glycolic acid copolymers.

In some embodiments of any of the aspects, the polymer is PDMS, polyurethane (PU), or poly(ethylene glycol) (PEG), or any curable polymer with a tunable elastic moduli. PDMS can be made using various ratios of elastomer to polymer base that can modulate the physical properties of the cured material (e.g., stiffness, rigidity, roughness, shear, clarity, etc.). In some embodiments of any of the aspects, the PDMS elastomer to PDMS base ratio is 1:5, 1:10, or 1:20. While any ratio of PDMS elastomer to PDMS base can be used as desired, it is specifically contemplated that the 1:20 ratio permits stability of the cured polymer and provides a stiffness that is amenable to engineering 3D cardiac tissues but also flexible enough to permit contraction of the cardiac tissues. PDMS is cast over a mold and cured in an oven or at room temperature for a period of time.

Once the PDMS is cured, the PDMS can then be removed from the negative mold and cut into three strips along the indicated lines (see e.g., FIG. 1B), thereby generating the final device.

For cell culture purposes, the systems and devices described herein are sterilized to prevent bacterial infection of cell cultures. Methods of sterilization are known in the art and are not described herein in detail. In certain embodiments the device is sterilized for at least 5 minutes in ultraviolet (UV) light, UV ozone, or plasma. In other embodiments, the devices described herein are UV sterilized for at least 10 min, at least 15 minutes, at least 20 min or more prior to seeding cardiomyocytes.

The heads described herein can be further chemically treated to increase cell adhesion. For example, the devices described herein can be treated with a sticky coating (e.g., plasma) for at least 30 seconds. As but one example, the wells are filled with poly-lysine and the heads are treated with the poly-lysine for 1-2 hours and then washed with PBS. The heads can then be treated with glutaraldehyde for 5, 10 or 15 minutes. Then, the devices are washed thoroughly in PBS and incubated in PBS in the fridge overnight.

In addition to the chemical treatment described above, an additional extracellular matrix protein can be added to promote further cellular adhesion or induce a desired cell signaling pathway (e.g., via integrin signaling). Examples of extracellular matrix proteins include but are not limited to collagen, fibronectin, fibrinogen, poly-lysine, vitronectin, laminin, elastin, tenascin, and Matrigel®. Other extracellular matrix formulations and proteins are known in the art. The extracellular matrix can be place in the device or system as described herein. For example, the heads can be chemically treated and coated with an extracellular matrix of choice. The extracellular matrix can also be cross-linked to the heads or pillars to promote cellular adhesion. Methods of cross-linking extracellular matrix proteins can be found, for example, in U.S. Pat. Nos. 6,224,893B1, 6,166,184A; Merrett et al. *Biomaterials.* (2009); and Shepherd et al. APL Materials (2015); which are incorporated herein by reference in their entirety.

Cell Suspensions:

As used herein the terms "cell suspension" or "suspension of cells" or "suspension of cardiomyocytes," refers to any mixture of cells delivered to the device or system as described herein used to generate the cardiac tissues. The cell suspension can also comprise co-cultured cells, mixtures of cell types known or unknown, as well as relevant growth factors, serum, culture medium, and nutrients necessary for maintaining and/or growing viable cells.

The system or device described herein can be immersed in a suspension of cells or cardiomyocytes, and the suspension can be delivered to the well (e.g., by a pipette). The cells in the suspension can be driven toward a top surface of the suspension in necessary. The suspension can then be polymerized to form a matrix, and the cells can be cultured over time to spontaneously compact the matrix. The pillar can anchor the contracting matrix, and can constrain the contraction of the matrix to form a band of tissue that spans across the pillars.

In certain embodiments, the suspension of cells can include a reconstitution mixture or prepolymer, such as collagen and fibrinogen. The cells can include any adherent cells, including neonatal rat heart cells, human cells, or human iPSC-derived cardiomyocytes or muscle cells. While the devices and systems described herein are useful for generating cardiac tissues comprising mature cardiomyocytes, the devices and systems can also be seeded with non-cardiac cells. For example, the cells can include one or more of heart cells, muscle cells, liver cells, neural cells, mesodermal, ectodermal, or endodermal lineage, embryonic or adult stem cells, fibroblasts, endothelial cells, smooth muscle cells of any origin, skeletal muscle cells, cardiac myocytes, myofibroblasts, epithelial cells, neuronal cells, glial cells, astrocytes, hepatocytes, kidney epithelial cells, intestinal cells, lymphocytes, or leukocytes. Additionally, or alternatively, the cells can include one or more of cells of human origin or cells of non-human origin including mouse cells, rat cells, rabbit cells, pig cells, bovine cells, primate cells, non-mammalian cells, fish cells, insect cells, mold cells, dictostelium cells, worm cells, or drosophila cells. Moreover, the cells can include one or more of cancer cells, immortalized cell lines, non-eukaryotic cells, bacteria, or viruses.

The cell suspension can also comprise of a population of iPSCs differentiated toward a cardiomyocyte lineage at different stages of maturity and/or a population of iPSC-CMs with purity of 70%, 80%, 85%, 90%, 95%, or 99% cardiomyocytes, can include additional cell types such as a stromal population including fibroblasts (e.g., cardiac fibroblasts), mesenchymal stem cells, endothelial cells, smooth muscle cells, and the like. The cell suspension can include other cells found resident or transiently in cardiac muscle, such as lymphocytes, monocytes, neutrophils, macrophages, etc. One of skill in the art would be able to determine the purity of the iPSC-CMs based on a cardiac-specific or stem cell-specific marker.

As used herein, the term "purity" or "pure" is used in reference to characteristics of a population of cells comprising cardiomyocytes and the number or percentage of those cells that are definitive cardiomyocytes, for example, cells that express at least one marker of a mature cardiomyocyte. For example, a population of cells where half of the cells are determined to be a mature cardiac myocyte, the purity of the population with respect to the cardiomyocytes (e.g., stem cell derived cardiomyocytes) is about 50%. The purity of the cardiomyocytes can be determined by measuring the presence of or expression level of a given cardiac marker that is known to be a marker of a mature cardiomyocyte or an adult cardiomyocyte (e.g., a genetic marker, structural marker, functional marker, or a phenotypic characteristic). Generally, prior to delivering cells to the device or system described herein, the purity of the cells in the suspension can be assessed by methods known in the art (e.g., flow cytometry). For example, troponin T expression can be used to determine cardiomyocyte purity. Therefore, the level of troponin T in the cell suspension can be used to determine the percentage (%) of cells in the total population expressing troponin T. The higher the percentage of cells expressing troponin T, the higher the purity of the cells. The purity can be 50% or more, 60% or more, 70% or more, 80% or more, 90% or more, or 100%. A purity of greater than 50% indicates that the majority of cells in the population express a cardiac marker and will likely exhibit a contractile response. A purity of about 100% indicates that all of the cells in the population express the cardiac marker and is referred to herein as a "substantially pure" population of cardiomyocytes.

Disease Modeling using Mature Cardiomyocytes In Vitro

The devices and systems described herein can be used in the generation and maturation of cardiomyocytes in culture, such that the cardiomyocytes can be used as a physiologically relevant model of cardiac muscle in both healthy and diseased conditions. Exemplary cardiac diseases and disorders that can be studied using cardiomyocytes generated and matured using the devices and systems described herein are briefly discussed below.

In some embodiments, cardiac electrophysiology and contractile function can be studied using a cell model comprising mature cardiomyocytes produced using the devices and systems described herein. For example, the matured cardiomyocyte tissues generated using the methods and devices described herein can be used to study hypertrophic cardiomyopathy or to test treatments for the same. Typically, cardiac electrophysiological and contractile function is a tightly controlled process, however when ion channel regulation or contractile function is disrupted in a cardiac cell or tissue, the resultant cardiac arrhythmias can sometimes be lethal. A number of diseases affect both the electrophysiology and contractile function of cardiac muscle, including but not limited to cardiac arrhythmias, cardiomyopathies (e.g., hypertrophic and dilated), long QT syndromes, arrhythmogenic right ventricular dysplasia (ARVD), catecholaminergic polymorphic ventricular tachycardia (CPVT), or Barth syndrome.

Although stem cell-derived cardiomyocytes have been used to model these diseases and disease phenotypes (Itzhaki et al., *Nature*. 2011; Moretti et al., *NEJM* 2010; Ma et al., *European Heart Journal*. 2012; Kim et al. *Nature*. 2013; Wang and McCain et al. *Nature Medicine*. 2014; Jung et al. *EMBO Molecular Medicine*. 2012; Hinson et al. *Science*. 2015), the functional maturity of iPSC-CMs in existing models is generally inconsistent across normal and diseased iPSC-CMs. Reliable methods of iPSC-CM maturation are neccessary, for example, to ensure that the disease phenotype represents, where appropriate, adult-onset of cardiac disease and disorders in order to identify therapeutics to treat these diseases and disorders effectively. The devices and systems described herein can reliably produce mature cardiomyocyte cells that can be used to study cardiac function in both health and disease. In addition, the devices and systems described herein can be used to accurately determine the cardiotoxicity of candidate drugs or agents. Prior studies have used cardiomyocyte cell cultures having a more fetal or immature phenotype, and as such, these cultures do not accurately reflect, cardiotoxic effects of drugs on cardiac tissues in vivo.

The devices and systems provided herein allow for the generation of disease phenotypes such as hypertrophic cardiomyopathy (e.g., cardiomyopathy associated with the R403Q mutation) and can be applied to essentially any cardiac disease and disorder of the muscle tissue that comprises an adult-onset of the phenotype. The methods and compositions described herein produce iPSC-CMs that are functionally mature, with a more adult phenotype based on a number of functional assays described herein.

Exemplary cardiac diseases that can be modeled using mature cardiomyocytes prepared and matured as described herein include those discussed, for example, in Smith et al., *Biotechnol. Adv.* 35: 77-94 (2017). More specifically, such diseases include ion channelopathies, such as Long QT Syndrome, for which a model using cardiomyocytes derived from iPS cells is described by Moretti et al., *New Engl. J. Med.* 363: 1397-1409 (2010). Other models include a model for the LQT1 subtype described by Egashira et al., *Cardiovasc. Res.* 95: 419-429 (2012), models for the LQT2 subtype described by Itzhaki et al., *Nature* 471: 225-229 (2011), Lahti et al., *Dis. Model Mech.* 5: 220-230 (2012), and Matsa et al., *Eur. Heart J.* 32: 952-962 (2011), and models for the LQT3 subtype described by Ma et al., *Int. J Cardiol.* 168: 5277-5286 (2013) and Terrenoire et al., *J. Gen. Physiol.* 141: 61-72 (2013). A model giving rise to both LQT3 and Brugada Syndrome subtypes is described by Davis et al., *Circulation* 125: 3079-3091 (2012), and a model for LTQ8 from Timothy Syndrome patients is described by Yazawa et al., *J. Cardiovasc. Transl. Res.* 6: 1-9 (2013).

Further cardiac diseases that can be modeled using cardiac cells differentiated from patients with such disease include the channelopathy catecholaminergic polymorphic ventricular tachycardia (CPVT). Models for this disease based on iPS cells differentiated to cardiomyocytes include those described by Itzhaki et al., *J. Am. Coll. Cardiol.* 60: 990-1000 (2012), Fatima et al., *Cell Physiol. Biochem.* 28: 579-592 (2011), Jung et al., *EMBO Mol. Med.* 4: 180-191 (2012) DiPasquale et al., *Cell Death Dis.* 4: e843 (2013), and Paavola et al., *Europace: European pacing, arrhythmias, and cardiac electrophysiology: journal of the working groups on cardiac pacing, arrhythmias, and cardiac cellular electrophysiology of the European Society of Cardiology* (2015) for CPVT1, and Novak et al., *Rambam Maimonides Med.* 1 3: e0015 (2012) for CPVT2.

Other disorders that can be modeled using iPS cell differentiation from subjects with diseases include hypertrophic cardiomyopathy (HCM) (Carvajal-Vergara et al., *Nature* 2010 465: 808-812 (2010) and Lan et al., *Cell Stem Cell* 12: 101-113 (2013)), and familial dilated cardiomyopathy (DCM) (Sun et al., *Sci Transl. Med.* 4: 130ra47 (2012), Siu et al., *Aging* 4: 803-822 (2012), Tse et al., *Hum. Mol. Genet.* 22: 1395-1403 (2013), Pompe disease (Huang et al., *Hum. Mol. Genet.* 20: 4851-4864 (2011), Friedrich's ataxia (FRDA) (Hick et al., *Dis. Model. Mech.* 6: 608-621 (2013), Barth Syndrome (Wang et al. *Nat. Med.* 20: 616-623 (2014)), arrhythmogenic right ventricular dysplasia/cardiomyopathy (ARVD/C) Calkins, Circulation Journal: official Journal of the Japanese Circulation Society 79: 901-913 (2015), Caspi et al., Circulation Cardiovascular Genetics 6: 557-568 (2013), Kim et al., *Nature* 494: 105-110 (2013), Malik and Rao, *Meth. Mol. Biol.* 997: 23-33 (2013).

Any or all of the disease models described above that use cardiac cells differentiated from iPS cells derived from subjects with the various diseases can benefit from the methods described herein for preparing and maturing cardiomyocytes (e.g., stem cell-derived cardiomyocytes).

Preparation of Stem Cell-Derived Cardiomyocytes

While it is specifically contemplated herein that primary cardiomyocytes can be seeded and matured using the devices and systems described herein, in certain embodiments cardiomyocytes to be matured as described herein can be differentiated in vitro from stem cells (e.g., induced pluripotent stem cells, embryonic stem cells, cardiac progenitor cells etc).

In some embodiments, stem cell-derived cardiomyocytes are differentiated from somatic cells derived from a subject, patient or donor. The somatic cells can be reprogrammed to induced pluripotent stem cells (iPS cells, iPSCs), which are then differentiated to cardiomyocytes. Thus, described herein are methods of reprogramming somatic cells to iPS cells, and also described herein are methods of differentiating iPS cells to stem cell-derived cardiomyocytes (e.g., human pluripotent stem cell-derived cardiomyocytes, hPSC-CMs, or iPSC-CMs). Methods for differentiating embryonic stem cells to cardiomyocytes are known in the art and largely analogous to those for differentiating iPS cells to cardiomyocytes.

Sources of Somatic Cells for Reprogramming into iPS Cells:

Stem cell derived-cardiomyocytes can be produced from a donor cell, which is induced to a pluripotent stem cell phenotype and can then be differentiated along the cardiomyocyte lineage. In one embodiment, the iPS cell is produced from a human subject or subjects thereof. Such iPS cells can be produced from healthy subjects, for example, for testing cardiotoxicity of drugs or agents on cardiac tissue. Alternatively, iPS cells can be produced from subjects having a disease or disorder associated with impaired cardiac muscle or electrical function, for example, to study agents for the treatment of such diseases or for research into the differences in phenotype of healthy cells vs. cells of a subject afflicted with a cardiac contractile or electrical disease or disorder.

It is also contemplated herein that iPS cells can be produced from any animal in addition to humans. In some embodiments, the cell donor is a mammal. In some embodiments, the animal is a vertebrate such as a primate, rodent, domestic animal or game animal. Primates include chimpanzees, cynomolgus monkeys, spider monkeys, and macaques, e.g., Rhesus. Exemplary rodents include e.g., mice, rats, woodchucks, ferrets, rabbits, guinea pigs, chinchilla and hamsters. Domestic and game animals can include e.g., cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. The cell donor, patient, or subject can include any of the subset of the foregoing as appropriate for a given use. In certain embodiments of the aspects described herein, the subject is a mammal, e.g., a primate, e.g., a human.

iPS cells can also be produced from essentially any stem cell(s). Exemplary stem cells include adult stem cells, neural stem cells, liver stem cells, muscle stem cells, endothelial progenitor cells, bone marrow stem cells, chondrogenic stem cells, lymphoid stem cells, mesenchymal stem cells, hematopoietic stem cells, central nervous system stem cells, peripheral nervous system stem cells, and the like. One of skill in the art can select a stem cell or other somatic cell for the purpose of generating stem-cell derived cardiomyocytes based on, for example, the ease of obtaining a sample from a subject. Stem cells that can be easily and relatively non-invasively obtained from a subject include hematopoietic stem cells, bone marrow stem cells, skin stem cells, and skeletal muscle stem cells. Descriptions of stem cells, including method for isolating and culturing them, can be found in, among other places, *Embryonic Stem Cells, Methods and Protocols,* Turksen, ed., Humana Press, 2002; Weisman et al., *Annu. Rev. Cell. Dev. Biol.* 17:387 403; Pittinger et al., *Science,* 284:143 47, 1999; Animal Cell Culture, Masters, ed., Oxford University Press, 2000; Jackson et al., *PNAS* 96(25):14482 86, 1999; Zuk et al., *Tissue Engineering,* 7:211 228, 2001 ("Zuk et al."); Atala et al., particularly Chapters 33-41; and U.S. Pat. Nos. 5,559,022, 5,672,346 and 5,827,735.

More often, iPS cells will be generated from differentiated donor cells including nucleated somatic cells including, but not limited to fibroblasts, stromal cells, muscle cells or cells of any of a wide number of tissues in the adult organism. Somatic cells that can be obtained from the subject using minimal invasiveness, for example, by a skin biopsy, urine sample, or by drawing blood, among other methods can be preferred over other somatic cells types.

In some embodiments, the iPS cells can be reprogrammed from cardiac cells, e.g., cardiac fibroblasts or from ventricular cardiomyocytes obtained from a subject, e.g., a mammalian subject including a human subject. A mixture of cells from a suitable source of cardiac tissue can be harvested from a mammalian donor or during open heart surgery by methods known in the art. The heart tissue is dissociated and cells plated in culture. Cardiac fibroblasts will adhere to the surface of the culture dish, permit collecting of the cardiac fibroblasts to reprogram to iPS cells.

While any tissue can provide source cells for generating iPS cells to differentiate into cardiomyocytes, it is contemplated that cells derived from cardiac tissue can have benefits, for example, epigenetic memory, that permit enhanced generation of mature cardiomyocytes when used in the methods described herein to generate iPS cell-derived cardiomyocytes.

Reprogramming of Somatic Cells to iPS Cells:

Methods of reprogramming differentiated cells to iPS cells are well known in the art and generally involve forced expression of Oct 3/4, Sox2, Klf4, and c-Myc in the cells, although numerous variations are known in the art. iPSCs can cultured, expanded and passaged according to the methods described herein or other conditions favorable to cell viability and maintenance of the undifferentiated, pluripotent phenotype. iPSCs are maintained, for example in hypoxic conditions (e.g., 37° C., 5% $CO_2$, 5% $O_2$).

iPS cells can also be generated using methods known to those of skill in the art, including, but not limited to non-viral methods, use of polycistronic vectors, mRNA species, miRNAs, and proteins, including methods described in, for example, International Patent Applications WO2010/019569, WO2009/149233, WO2009/093022, WO2010/022194, WO2009/101084, WO2008/038148, WO2010/059806, WO2010/057614, WO2010/056831, WO2010/050626, WO2010/033906, WO2009/126250, WO2009/143421, WO2009/140655, WO2009/133971, WO2009/101407, WO2009/091659, WO2009/086425, WO2009/079007, WO2009/058413, WO2009/032456, WO2009/032194, WO2008/103462, JP4411362, EP2128245, and U.S. Patent Applications US2004/0072343, US2009/0253203, US2010/0112693, US2010/07542, US2009/0246875, US2009/0203141, US2010/00625343, US2009/0269763, and US2010/059806, each of which are incorporated herein in their entirety by reference.

Differentiating Stem Cells to Stem Cell-Derived Cardiomyocytes:

Generation of cardiomyocytes from stem cells can be performed using any method known to those of skill in the art. Accordingly such methods are not described in detail herein. Briefly, iPSCs can be dissociated into single cells using a cell dissociation reagent (e.g., trypsin or ethylenediaminetetraacetic acid) and plated on matrix-coated (e.g., Matrigel® coated) plates in stem cell culture medium (See

*Current Protocols in Stem Cell Biology.* 2:1C.2.1-1C2.16, 2007) in preparation for differentiation to cardiomyocytes. Other extracellular matrix protein surface treatments can be used for standard monolayer culture of the iPS cells. Non-limiting examples of surface treatments of culture dishes include proteins or mixtures thereof such as gelatin, collagen, fibronectin, etc.

To prepare iPS cells for differentiation to cardiomyocytes, the iPS cells are seeded at high density (250,000 cells/mm$^2$ or more). Once a monolayer has formed, cells can be differentiated to cardiomyocytes, for example, as described by Karakikes et al. *Insights into Molecular, Cellular and Functional Phenotypes.* 117, 80-88 (2016); and Lundy et al. *Stem Cells Dev.* 22, 1991-2002 (2013) which are incorporated herein by reference in their entireties. Other approaches known in the art for differentiating pluripotent stem cells (iPS or ES cells) to cardiomyocytes can also be used.

In some embodiments, the iPS cells are genetically modified after or during the pluripotent state. For example, disease model cell lines, (e.g., R403Q human iPS cells) can be generated using CRISPR-Cas technology to create an isogenic pair from a normal parental cell line. Other approaches for genetically modifying iPS cells can also be used, including but not limited to the introduction of viral vectors, liposome-mediated transfections, microinjection, etc. Genetic modifications can include both changes that increase expression of one or more factors, or, conversely, that inactivate or otherwise inhibit expression of one or more factors.

Following the differentiation of the cardiomyocytes, they can be tested for cell purity using a number of phenotypic markers. Generally, a marker that is expressed by a mature or adult cardiomyocyte is used to determine cell purity of stem cell-derived cardiomyocytes. Non-limiting examples of cardiac-specific biomarkers include troponin T2 (Tnnt2), titin (Ttn), myosin, heavy polypeptide 6 (Myh6), Mhy7, ryanodine receptor 2 (Ryr2), α-actinin, myocardin, and ion channels (e.g., Cacna1d, Cacna1h, Kcnh2, etc).

Culture and Maturation of Cardiomyocytes Using the Devices and Systems Described Herein Cardiomyocytes or stem cell-derived cardiomyocytes can be seeded into a well of a device or system as described herein in order to form cardiac tissue and to mature the phenotype of the cells. Typically, the well will comprise at least one extracellular matrix protein to permit or enhance adhesion of the cardiomyocytes in the well of the device. Non-limiting examples of extracellular matrices include collagen, fibronectin, fibrinogen, poly-lysine, vitronectin, laminin, elastin, tenascin, and Matrigel®. Other extracellular matrix formulations and proteins are known in the art. The extracellular matrix can be place in the device or system as described herein. Methods for coating pillar heads in a device are described elsewhere herein.

In order to induce maturation of cardiomyocytes (e.g., primary or stem cell-derived cardiomyocytes), a desired number of cells are seeded into each of the wells in a device or system as described herein. The seeding of the cells can vary depending on the size and dimensions of each well and the type of cells introduced. One of ordinary skill in the art will appreciate that an appropriate cell density can be varied depending on the desired application and/or particular size and dimensions of the wells. However, for purposes of illustration and not limitation, cell density for cardiomyocytes can range from, for example, 1,000 cells per mL to 100,000,000 cells per mL, and lead to seeding of 1 cell per device, 2 cells per device, 2-5 cells per device, 5-10 cells per device, 10-100 cells per device, 10-50 cells per device, 50-100 cells per device, 100-200 cells per device, 200-400 cells per device, 400-1000 cells per device, 1000-10,000 cells per device, 10,000-100,000 cells per device, or the like.

While the devices and systems described herein are designed for growth and maturation of cardiomyocytes, it is specifically contemplated herein that the devices, systems and methods described herein can be used in the culture of non-cardiac cells (e.g., skeletal muscle cells, smooth muscle cells, myofibroblasts etc.). The use of non-cardiac cells with the devices disclosed herein can allow for characterization of the contractility of these tissues and used to identify novel targets, molecules, proteins, and drugs to modulate muscle contractility. Moreover, in certain embodiments, the cells can include diseased cells, normal cells, or a mixture thereof Such cells can additionally or alternatively include, but limited to, cells of mesodermal, ectodermal, or endodermal lineage, embryonic or adult stem cells, fibroblasts, endothelial cells, smooth muscle cells of any origin, skeletal muscle cells, cardiac myocytes, myofibroblasts, epithelial cells, neuronal cells, glial cells, astrocytes, hepatocytes, kidney epithelial cells, intestinal cells, lymphocytes, leukocytes, cells of human origin, cells of non-human origin, mouse cells, rat cells, rabbit cells, pig cells, bovine cells, primate cells, non-mammalian cells, fish cells, insect cells, mold cells, dictostelium cells, worm cells, drosophila cells, cancer cells, cell lines, non-eukaryotic cells, bacteria, and/or viruses.

The cardiomyocytes can be cultivated over time by addition of the appropriate media to each well of the device. Over cultivation time, the cells will typically spread inside the matrix, form cell-cell contracts, and spontaneously compact the matrix over several days. The pillars will anchor the contracting matrix, constraining the contraction of the collagen/fibrin matrix to form a linear band of cardiac tissues that spans across the top of the pillars. The devices and systems described herein are particularly advantageous in the generation of cardiac tissues that are thin enough to promote optimal oxygen and nutrient diffusion, while also being thick enough to be stable throughout a given assay.

Such cardiac tissues improve the longevity of the cells in culture, for example, by at least 1 day, at least 2 days, at least 3 days, at least 4 days, at least 5 days, at least 6 days, at least 1 week, at least ten days, at least 2 weeks, at least 3 weeks, at least 4 weeks or longer than the cardiac tissues grown in similar devices, for example, those lacking coated caps/heads that permit the cells/tissues to "stick" to the pillars.

Over time, the cells elongate and align along the axis between the pillars. As cultivation continues, the cells begin spontaneously beating as a single unit. As cultivation further continues, the cells start to beat coherently, bending the flexible pillars toward each other at each contraction.

The time from seeding to tissue assembly can range from hours to days. Such a time period can depend on, among other things, the type of cells introduced, the geometry of the wells and/or pillars, and the composition of the prepolymer matrix. For example, different cell types can remodel and contract extracellular matrix at different rates. For example, tissues comprised of cardiomyocytes can take 2-3 days to fully contract around the posts of the well and another 1-2 days to establish excitation-contraction coupling, and exhibit spontaneous or synchronous beating. A lower density prepolymer matrix can lead to faster tissue contraction and remodeling, while a higher density prepolymer matrix can take longer to contract. Culturing the cardiac tissues in media with certain growth factors can also affect tissue assembly.

The time from seeding to tissue maturation can range from hours to weeks. Such a time period can likewise depend on, among other things, the type of cells introduced, the geometry of the well and/or pillars, and the composition of the prepolymer matrix. For example, in order to mature, stable anchoring of the tissues on the pillars of the well can be adjusted.

As such, the geometry of the head (rounded rectangles, oval shaped, circular shaped) can affect tissue stability and maturation. The width of the pillar and head can also have an effect. Wider pillars can form "dog-bone" shaped tissues that are wide around the pillars and narrow in the middle. By contrast, narrow pillars can tend to anchor tissues with a more uniform cross-section. These differing cross sectional profiles can have different micro-structures as a result of different cell alignment, cell distribution and matrix remodeling. See e.g., the working Examples for a detailed discussion of the effect of head geometry on cardiac tissue formation.

Moreover, the techniques disclosed herein can provide a cardiac tissue assay suitable for high throughput monitoring of, e.g., drug-induced changes in spontaneous frequency of contractility in cardiac tissues. The small (e.g., micrometer) scale of the cardiac tissues can provide for rapid penetration of soluble effectors into the constructs. For example, introduction of isoproterenol and/or digoxin can produce reproducible, dose-dependent effects on cardiac tissue contractility and beating frequency.

In certain embodiments, replacement of serum (e.g 10% fetal bovine or horse serum) with physiological growth factors such as insulin-like growth factor (IGF-1) and/or the steroid agonist clenburerol can further improve the diastolic relaxation and contractile reserve of human cardiac tissues. Any factor known in the art that further improves cardiomyocyte maturation can be used. Productive seeding routines, pillar stiffness and electrical conditioning routines can be employed in connection therewith. The effects of growth factors implicated in physiological growth can be systematically assessed both individually and in combination. For each of the growth factors assessed, dose-response relationship can be determined.

In connection with the techniques disclosed herein, the structural and functional characteristics of cardiac tissues can be similar to in vivo heart muscle, and can provide for high throughput, low volume screening applications. Moreover, techniques disclosed herein can quantitatively demonstrate the impact of physical parameters on the maturation, structure and function of cardiac tissue provide opportunities to elucidate mechanisms of load-dependent myocardial remodeling in stable, three-dimensional, working muscle preparations. Furthermore, the techniques disclosed herein can provide for reproducible contractile phenotyping, which can be difficult in two-dimensional culture models.

In some embodiments, electrical stimulation is used in the maturation of the cardiomyocytes as described herein. In some embodiments, the electrical stimulation frequency is 0.1 Hz or more, 0.5 Hz or more, 1 Hz or more, 1.8 Hz or more, 2 Hz or more, 2.7 Hz or more, 3 Hz or more, 3.5 Hz or more, 4 Hz or more, 4.8 Hz or more, 5 Hz or more, 5.2 Hz or more, 6 Hz or more, 7 Hz or more, 8 Hz or more, 9 Hz or more, or 10 Hz. In some embodiments, the electrical stimulation is a high frequency ramp. The electrical stimulation itself or the electrical stimulation regimen (a series of electrical stimulations over any given time period) can be carried out in any given amount of time (e.g., milliseconds, seconds, minutes, hours, days, weeks, months, etc). In some embodiments, the electrical stimulation is conducted 4 days after the stem cell-derived cardiomyocytes are cultured in the device or system described herein. In some embodiments, the electrical stimulation is conducted for 6 hours per day for three days.

The electrical stimulator in the system or device described herein can be internal to the device or external (e.g., wires that are inserted in the culture medium). The external electrical stimulator can be a field stimulator (e.g., an IonOptix C-Pace EP Culture Pacer) or an automated/manual patch clamp electrode. The internal electrical stimulator can be, for example, a microelectrode or microelectrode array built into the system or device described herein.

The waveform of the electrical stimulation can be adjusted to any shape, duration, or polarity. The electrical stimulation can be in the form of a pulse train or a single stimulation. In some embodiments, the voltage of the electrical stimulation is 0.01 volts (V) or more, 0.05V, or more, 0.10V or more, 0.50V or more, 1.0V or more, 1.5V or more, 2.0V or more, 2.5V or more, 3.0V or more, 3.5V or more, 4.0V or more, 4.5V or more, 5.0V or more, 5.5V or more, 6.0V or more, 6.5V or more, 7.0V or more, 7.5V or more, 8.0V or more, 8.5V or more, 9.0V or more, 9.5V or more, 10.0V or more. One of skill in the art can readily determine an appropriate voltage for a given cardiac tissue based on the size of the cardiac tissue. For example, the cardiac tissue described herein can be stimulated at a voltage of 2.5 V/cm, which is a voltage that permits maturation of cardiomyocytes without diminishing cell viability.

It is contemplated that the electrical stimulation can also be optical stimulation. For example, methods of optogenetic pacing of cardiomyocytes and tissues are known in the art. See for example, U.S. Pat. Nos. 9,057,734B2; 9,238,150B2; US20130274838A1; US20190025291A1; which are incorporated herein by reference in their entirety.

Functional Characterization of Cardiomyocytes

Cardiomyocytes, including stem-cell derived cardiomyocytes, matured under the conditions described herein permit evaluation of the response of mature cardiomyocytes to various treatments or stimuli. In various embodiments, quantifiable parameters of stem cell-derived cardiomyocytes can include contractile force, contractility, altered contraction, frequency of contraction, contraction duration, contraction stamina, cardiomyocyte size, sarcomere organization, length, circumference, structure, multinucleate status, metabolic respiratory capacity, oxygen consumption, electrophysiological and biophysical parameters. In some embodiments, quantifiable parameters include survival and/or division or regeneration of the e.g., stem cell-derived cardiomyocytes.

While most parameters will provide a quantitative readout, in some instances a semi-quantitative or qualitative result will be acceptable. Readouts can include a single determined value, or can include mean, median value or the variance, etc. Characteristically a range of parameter readout values will be obtained for each parameter from a multiplicity of the same assays. Variability is expected and a range of values for each of the set of test parameters will be obtained using standard statistical methods to provide useful values.

Measurements of various parameters useful for evaluating cardiomyocyte status or function are described in the following.

Immunoassays: Standard methods in immunology known in the art and not specifically described are generally followed as in Stites et al. (Eds.), *Basic and Clinical Immunology*, 8th Ed., Appleton & Lange, Norwalk, Conn. (1994);

and Mishell and Shigi (Eds.), Selected *Methods in Cellular Immunology,* W. H. Freeman and Co., New York (1980).

In general, immunoassays are employed to assess expression of e.g., cardiomyocyte-specific cell surface or intracellular markers, depending upon how the cell is prepared for assay. Immunocytochemical assays are well known to those skilled in the art. Both polyclonal and monoclonal antibodies can be used in such assays. Where appropriate, other immunoassays, such as enzyme-linked immunosorbent assays (ELISAs), radioimmunoassays and flow cytometry can be used to detect cell type specific markers.

Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771; and 5,281,521 as well as Sambrook et al., *Molecular Cloning: A Laboratory Manual,* Cold Springs Harbor, N.Y., 1989, among others.

Non-limiting examples of cardiac-specific markers one can assay for using immuno-based methods include cardiac troponin T, cardiac troponin-C, tropomyosin, caveolin-3, GATA-4, myosin heavy chain, myosin light chain-2a, myosin light chain-2v, ryanodine receptor, atrial natriuretic factor, among others.

Sarcomere Organization:

Confirmation of cardiomyocyte differentiation and maturation can be assessed by assaying sarcomere morphology and structural characterization of actin and myosin. The structure of cardiac sarcomeres is highly ordered, thus one with ordinary skill in the art can recognize these proteins (actin, myosin, alpha-actinin, titin) and their arrangement in tissues or collections of cultured cells can be used as markers to identify mature muscle cells and tissues. Developing cardiac cells undergo "sarcomerogenesis," which creates new sarcomere units within the cell. The degree of sarcomere organization provides a measure of cardiomyocyte maturity.

Immunofluorescence assays and electron microscopy for $\alpha$-actinin, $\beta$-myosin, actin, cTnT, tropomyosin, and collagen, among others can be used to identify and measure sarcomere structures. Immunofluorescent images can be quantified for sarcomere alignment, pattern strength, and sarcomere length. This can be accomplished by staining the protein within the sarcomeres (e.g., $\alpha$-actinin) and qualitatively or quantitavely determining if the sarcomeres are aligned. For a quantitative measurement of sarcomere alignment, several methods can be employed such as using a scanning gradient and Fourier transform script to determine the position of the proteins within the sarcomeres. This is done by using each image taken by a microscope and camera for individual analysis. Using a directional derivative, the image gradient for each segment can be calculated to determine the local alignment of sarcomeres. The pattern strength can be determined by calculating the maximum peaks of one-dimensional Fourier transforms in the direction of the gradient. The lengths of sarcomeres can be calculated by measuring the intensity profiles of the sarcomeres along this same gradient direction.

Cellular morphology can be used to identify structurally mature stem cell-derived cardiomyocytes. Non-limiting examples of morphological and structural parameters include, but are not limited to, sarcomere length, Z-band width, binucleation percentages, nuclear eccentricity, cell area, and cell aspect ratio.

Alternatively, qualitative analysis of sarcomeric structure can also be used. For one with ordinary skill in the art, the standard for an adult cardiomyocyte phenotype is that the alpha ($\alpha$)-actin is about 90 degrees to the actin filaments. A fetal cardiomyocyte does not typically express $\alpha$-actinin, or the $\alpha$-actinin structure is disordered from the sarcomere structure. The cardiac tissues described herein develop a robust aligned sarcomere formation and collagen deposition which indicate that the cardiac tissues in the system or device described herein, are more mature than those that are not grown in a 3D environment or grown in a monolayer.

Measures of sarcomere organization as described above can also be used to assess toxic effects of a drug or agent using mature cardiomyocytes from a subject(s) not known to have a cardiac condition or dysfunction. In such cases, the sarcomere organization/disorganization can be observed prior to contacting the cells or tissues with the agent and the effect on sarcomere organization can be followed over time to determine the effect of the drug/agent on sarcomere organization and overall cardiac tissue health and function. Alternatively, effect of an agent on sarcomere organization can be observed in a given sample as compared to a reference sample comprising substantially similar cells that are not contacted with the agent. The presence of, or an increase in, sarcomere disorganization in the presence of an agent can be indicative of cardiotoxicity of the agent.

In some embodiments, mature cardiomyocytes derived from a subject having a cardiac disease or disorder comprising sarcomere disorganization (e.g., cardiomyopathy) or mature cardiomyocytes genetically modified to mimic a physiological disorder (e.g., R403Q mutation) can be used to assess the efficacy of treatment of the cardiac disease or dysfunction using a given agent. Such disease models can be monitored for an increase in the organization of sarcomeres, which can indicate that the drug or agent tested can be used in the treatment of the disease or disorder.

Electrophysiology:

Mature cardiomyocytes have functional ion channels that permit the synchronization of cardiac muscle contraction. The electrical function of cardiomyocytes can be measured by a variety of methods. Non-limiting examples of such methods include whole cell patch clamp (manual or automated), multielectrode arrays, field potential stimulation, calcium imaging and optical mapping, among others. Cardiomyocytes can be electrically stimulated during whole cell current clamp or field potential recordings to produce an electrical and/or contractile response. Furthermore, cardiomyocytes can be genetically modified, for example, to express a channel rhodopsin that allows for optical stimulation of the cells. It is also contemplated herein that the devices and systems described herein can be used to stimulate and/or detect electrical impulses and cardiac electrical coupling of mature cardiomyocytes.

Measurement of field potentials and biopotentials of cardiomyocytes can be used to determine the differentiation stage and cell maturity. Without limitations, the following parameters can be used to determine electrophysiological function of e.g., cardiomyocytes: change in FPD, quantification of FPD, beat frequency, beats per minute, upstroke velocity, resting membrane potential, amplitude of action potential, maximum diastolic potential, time constant of relaxation, action potential duration (APD) of 90% repolarization, interspike interval, change in beat interval, current density, activation and inactivation kinetics, among others.

During a disease state, the electrophysiological function of cardiomyocytes can be compromised, and this can be recapitulated by disease models using cardiomyocytes matured as described herein. For example, stem cell-derived cardiomyocytes used to model a cardiac arrhythmia such as long QT syndrome, can exhibit a prolonged FPD and APD when compared with normal stem cell-derived cardiomyocytes.

Metabolic Assays:

Adult cardiomyocytes have been shown to have enhanced oxidative cellular metabolism compared with fetal cardiomyocytes marked by increased mitochondrial function and spare respiratory capacity. Metabolic assays can be used to determine the differentiation stage and cell maturity of the stem cell-derived cardiomyocytes as described herein. Non-limiting examples of metabolic assays include cellular bioenergetics assays (e.g., Seahorse Bioscience XF Extracellular Flux Analyzer), and oxygen consumption tests.

Specifically, cellular metabolism can be quantified by oxygen consumption rate (OCR), OCR trace during a fatty acid stress test, maximum change in OCR, maximum change in OCR after FCCP addition, and maximum respiratory capacity among other parameters.

Furthermore, a metabolic challenge or lactate enrichment assay can provide a measure of stem cell-derived cardiomyocyte maturity or a measure of the effects of various treatments of such cells. Mammalian cells generally use glucose as their main energy source. However, cardiomyocytes are capable of energy production from different sources such as lactate or fatty acids. In some embodiments, lactate-supplemented and glucose-depleted culture medium, or the ability of cells to use lactate or fatty acids as an energy source is useful to identify mature cardiomyocytes and variations in their function.

As one of skill in the art will recognize, metabolic assays can be used as a functional endpoint in a screening assay or toxicity assay to determine the effects of a given agent on cardiac function using the mature cardiomyocytes, devices and systems described herein. For example, hypertrophic cardiomyopathy can be associated with a more fetal metabolic phenotype, thus an agent that shifts the metabolic phenotype of the mature cardiomyocytes to a more fetal metabolic phenotype can be indicative of cardiotoxicity of the given agent.

Methods to Measure Cardiac Contractility:

In one embodiment of any of the aspects, the device described herein is used to measure cardiac contractile function. Contractility can be measured by optical tracking methods such as video analysis. Functional outputs such as contraction magnitude, velocity, and angle are output as a vector field for each video frame and can be averaged spatially or temporally. For video tracking methods, contraction (or systole) of the cardiomyocytes is considered to be the point in time and space where the cell or cardiac tissue is at the shortest length. Relaxation (diastole) is considered to be the point in time or space where the cell or cardiac tissue is at the largest length. These parameters are determined by measuring displacement of the pillars that the cardiac tissue is adhered to. A reference frame within the video can be used to track the motion of the cardiomyocyte or cardiac tissue over time. The displacement of the pillars can be tracked using, for example, the SpotTracker plug-in on ImageJ software. The displacement values can be run through a custom MATLAB script to compute twitch force. The spring constant of the pillars can be theoretically calculated (see Table 1). In the final platform design fabricated in 1:20 PDMS, the spring constant of the pillar was calculated to be k=2.677.

In addition to optical tracking, impedimetric measurements can also be performed. For example, the cardiomyocytes described herein can have contractility or beat rate measurements determined by xCelligence™ real time cell analysis (Acea Biosciences, Inc., San Diego, Calif.).

A useful parameter to determine cardiomyocyte function is beat rate. The frequency of the contraction, beat rate, change in beat interval (ABI), or beat period, can be used to determine stem cell differentiation stage, stem cell-derived cardiomyocyte maturity, and the effects of a given treatment on such rate. Beat rate can be measured by optical tracking. The beat rate is typically elevated in fetal cardiomyocytes and is reduced as cardiomyocytes develop. During disease states the change in beat rate can be variable and lack a constant frequency due to electrophysiological or structural instability. Without limitations, contractile force, contractile parameters can also include contraction velocity, relaxation velocity, contraction angle distribution, or contraction anisotropic ratio.

Another useful parmeter to determine cardiomyocyte function is contractile force. Optical tracking can be used to deteremine the displacement of cardiac tissue as the tissue beats in culture. Force tracing of paced cardiac tissue over time can be calculated with custom software or a combination of ImageJ and Matlab scripts. Force output of the cardiac tissues can be increased using pharmaceuticals known in the art (e.g., isoproterenol) to measure the relative changes in contractile function with each dose.

The devices and systems described herein can be used herein to assess efficacy or toxicity of a given agent by measuring cardiac contractility as a functional endpoint.

Drug Screening Platforms using Cardiomyocytes

The matured cardiomyocytes prepared as described herein provide a platform for the study or evaluation of the likely effects of known or experimental drugs on cardiomyocytes or cardiac tissue in vivo. This can be used to evaluate drugs to be used for treating non-cardiac indications for possible cardiac side-effects or cardiotoxicity. Alternatively, by screening with, for example, a library or collection of potential drugs or agents, cardiomyocytes prepared and matured as described herein can also be used to identify new drugs with beneficial effects on cardiomyocyte or cardiac function. Cardiomyocytes derived from a non-diseases subject can provide useful information in both situations, and cardiomyocytes derived from subjects with a cardiac or other disease, or derived from cells engineered to mimic a cardiac disease or disorder can be very useful in identifying new drugs or agents to treat such diseases. In either instance, the evaluation of functional or structural parameters as described herein or as known in the art can be informative with regard to the effects of a given agent. In general, such assays comprise contacting cardiomyocytes prepared and matured as described herein with an agent and measuring one or more parameters of the cardiomyocytes described herein as an indicator of the agent's effect(s). Where effects are observed, dose responses can also be evaluated by varying the concentration of the agent and/or the duration of contacting. One benefit of the matured cardiomyocytes as described herein is that they maintain their mature phenotype for an extended period in culture (weeks or more, under optimal conditions) relative to less mature cultured cardiomyocytes. This can also permit the collection of data on, for example, long term, low level exposure to an agent that would not be possible for cardiomyocytes in another platform.

Accordingly, cardiomyocytes prepared and matured using the devices and systems described herein can be used to identify an agent or evaluate an agent for its effect on parameters such as expression of markers, cell viability, sarcomere arrangement, contractility, electrophysiological responses, beat rate, or other parameters described herein or known in the art.

In some embodiments, such mature cardiomyocytes can be used in assays to screen agents, selected from small molecules, nucleic acids or analogues thereof, aptamers; proteins or polypeptides or analogues or fragments thereof, among other agents for effects, detrimental or beneficial, on the cells. To the extent that cardiomyocytes prepared and matured as described herein can recapitulate or mimic the effects of drugs on cardiac tissue, it is also contemplated that cardiomyocytes prepared and matured as described herein can be used to screen for an agent that counters the cardiac side effect of another drug, useful for a non-cardiac indication.

In some embodiments, the agent is an agent of interest including known and unknown compounds that encompass numerous chemical classes, primarily organic molecules, which can include organometallic molecules, inorganic molecules, genetic sequences, etc. An important aspect of the use of stem cell-derived cardiomyocytes as described herein is to evaluate candidate drugs, including toxicity testing; and the like. Candidate agents also include organic molecules comprising functional groups necessary for structural interactions, particularly hydrogen bonding, and typically include amine, carbonyl, hydroxyl or carboxyl groups, frequently more than one of such functional chemical groups. The candidate agents often comprise cyclic carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof Also included as agents are pharmacologically active drugs, genetically active molecules, etc. Compounds of interest include, for example, chemotherapeutic agents, hormones or hormone antagonists, growth factors or recombinant growth factors and fragments and variants thereof. Exemplary of pharmaceutical agents suitable for this invention are those described in, "The Pharmacological Basis of Therapeutics," *Goodman and Gilman,* McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," *Academic Press,* New York, 1992).

Compounds, including candidate agents, can be obtained from a variety of sources including libraries of synthetic or natural compounds. Various means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and can be used to produce combinatorial libraries. Known pharmacological agents can be subjected to directed or random chemical modifications, such as acylation, alkylation, esterification, amidification, etc. to produce structural analogs.

Candidate agents include all of the classes of molecules described above, and can further comprise samples of unknown content. Of interest are complex mixtures of naturally occurring compounds derived from natural sources such as plants. While many samples will comprise compounds in solution, solid samples that can be dissolved in a suitable solvent can also be assayed. Samples of interest include environmental samples, e.g., ground water, sea water, etc.; biological samples, e.g., lysates prepared from crops, tissue samples, etc.; manufacturing samples, e.g., time course during preparation of pharmaceuticals; as well as libraries of compounds prepared for analysis; and the like.

In some embodiments, the effect of the agent is determined by quantifiable parameters of cardiomyocytes can include contractile force, contractility, altered contraction, frequency of contraction, contraction duration, contraction stamina, cardiomyocyte size, sarcomere organization, length, structure, metabolic respiratory capacity, oxygen consumption, and electrophysiological and biophysical parameters. In some embodiments, quantifiable parameters include differentiation, survival and regeneration of the cardiomyocytes.

A plurality of assays comprising cardiomyocytes can be run in parallel with different agent concentrations to obtain a differential response to the various concentrations. As known in the art, determining the effective concentration of an agent typically uses a range of concentrations resulting from 1:10, or other log scale, dilutions. The concentrations can be further refined with a second series of dilutions, if necessary. Typically, one of these concentrations serves as a negative control, i.e. at zero concentration or below the level of detection of the agent or at or below the concentration of agent that does not give a detectable change in the phenotype.

Optionally, the stem cell-derived cardiomyocytes used in the screen can be manipulated to express desired gene products.

As used herein, the term "test compound" or "candidate agent" refers to an agent or collection of agents (e.g., compounds) that are to be screened for their ability to have an effect on the cell. Test compounds can include a wide variety of different compounds, including chemical compounds, mixtures of chemical compounds, e.g., polysaccharides, small organic or inorganic molecules, biological macromolecules, e.g., peptides, proteins, peptide analogs, and analogs and derivatives thereof, peptidomimetics, nucleic acids, nucleic acid analogs and derivatives, an extract made from biological materials such as bacteria, plants, fungi, or animal cells or tissues, naturally occurring or synthetic compositions.

Depending upon the particular embodiment being practiced, the test compounds can be provided free in solution, or can be attached to a carrier, or a solid support, e.g., beads. A number of suitable solid supports can be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds can be screened individually, or in groups. Group screening is particularly useful where hit rates for effective test compounds are expected to be low such that one would not expect more than one positive result for a given group.

Without limitation, the compounds can be tested at any concentration that can exert an effect on the cells relative to a control over an appropriate time period. In some embodiments, compounds are tested at concentrations in the range of about 0.01 nM to about 100 mM, about 0.1 nM to about 500 µM, about 0.1 µM to about 20 µM, about 0.1 µM to about 10µM, or about 0.1 µM to about 5 µM.

The compound screening assay can be used in a high through-put screen. High through-put screening is a process in which libraries of compounds are tested for a given activity. High through-put screening seeks to screen large numbers of compounds rapidly and in parallel. For example, using microtiter plates and automated assay equipment, a laboratory can perform as many as 100,000 assays per day in parallel.

The compound screening assays described herein can involve more than one measurement of the cell or reporter function (e.g., measurement of more than one parameter and/or measurement of one or more parameters at multiple points over the course of the assay). Multiple measurements can allow for following the biological activity over incubation time with the test compound. In one embodiment, the reporter function is measured at a plurality of times to allow monitoring of the effects of the test compound at different incubation times.

The screening assay can be followed by a subsequent assay to further identify whether the identified test compound has properties desirable for the intended use. For example, the screening assay can be followed by a second assay selected from the group consisting of measurement of any of: bioavailability, toxicity, or pharmacokinetics, but is not limited to these methods.

Reference Levels and Appropriate Controls

The systems, devices, and methods herein allow for the comparison of cellular and tissue properties and phenotypes with a reference level or an appropriate control.

As used herein, a "reference level" refers to a normal, otherwise unaffected or untreated cell population or tissue (e.g. cardiomyocytes obtained from a healthy subject, or cardiomyocytes obtained from a subject at a prior time point, or a cell or cell population that has not been contacted with an agent). One of skill in the art would be able to choose the appropriate reference level for the desired experiment or test.

As used herein, an "appropriate control" refers to an untreated, otherwise substantially identical cell or population (e.g., a cell or cell population that was not contacted by an agent, or not contacted in the same manner, e.g., for a different duration, as compared to a non-control cell). The appropriate control can be determined by one of skill in the art.

Generally, an appropriate control or reference level refers to cells or cardiomyocytes that were not contacted by an agent or were not genetically modified (e.g. healthy cardiomyocytes). For example, the cells or cardiomyocytes can be isolated from mammalian subjects or can be differentiated cardiomyocytes.

One example of using a reference level or appropriate control includes testing for cardiotoxicity of an agent. The appropriate control or reference level would be a cell, cardiomyocyte, or population thereof that has not been contacted with a test compound. The effect of the test compound on at least one phenotypic characteristic of the cell or population thereof can be determined by methods known in the art. For example, the phenotypic characteristics associated with cardiotoxicity include impaired contractile function, decreased beat rate, impaired electrical function, impaired metabolic function, a decrease in cell viability, or a decrease in expression of a cardiac marker. Methods of measuring these phenotypic characteristics are known in the art. In some embodiments, the cardiotoxicity of an agent is indicated by the agent's effect on one or more of: cell viability, cell size, sarcomere length, organization of sarcomeres within a tissue, a biopotential or electrical property of a population of cardiomyocytes, mitochondrial function, gene expression, beat rate, beat strength, and contractility.

Alternatively, the reference level or appropriate control can be but is not limited to, stem cell-derived cardiomyocytes that were purchased commercially or are stem cell-derived cardiomyocytes derived from a healthy subject for comparison with stem cell-derived cardiomyocytes differentiated or matured using the systems and devices described herein. With regard to disease modelling, the reference level or appropriate control is the healthy tissue or cell population for comparison with the muscular disease or disorder.

Furthermore, the appropriate control can be a benchmark for developing a novel differentiation protocol for stem cell-derived cardiomyocytes. In that case, the reference level or appropriate controls can be but is not limited to a mature cardiomyocyte population (e.g., adult cardiomyocytes, non-fetal cardiomyocytes) or cardiomyocytes generated by a standard protocol known in the art.

The reference levels and appropriate controls can also serve as a method to measure the performance of the systems and devices described herein. For example, the appropriate control can be cells grown in a monolayer or grown as a laminer tissue for comparison with the 3D cardiac tissues grown in the system and devices described herein.

Another example of an appropriate control or reference level can be a cardiac tissue that is not co-cultured with another cell type (e.g., stromal cells). Such a control cen be used to determine the effect of different cell types on cardiac function or gene expression when comparing to a test cardiac tissue grown in the presence of at least one additional cell.

Yet another example of an appropriate control or reference level is related to the dimensions or modifications made to the systems and devices described herein. As an example, a standard version of the device can be used as an appropriate control for comparison with another device that has different spacing between pillars or an alternative sticky coating on the heads on top of the pillars. Thus, the modifications to the device and system described herein can be made to permit the generation of improved 3D cardiac tissues.

In various embodiments of the present invention, a reference value can be used based on at least one metric or phenotypic characteristic of a cell, cell population, cardiomyocyte, or cardiac tissue. As used herein, a "reference value" refers to a parameter, number, value, or range of values that is determined or expected for a given phenotypic characteristic. A reference value can be based on an average value for a given phenotypic characteristic determined from prior experiments using the same cell model (e.g., a reference value can be obtained for a given phenotypic characteristic for each tested system, device, or cell population as described herein). For example, where the phenotypic characteristic comprises contractile force, the reference value can be a number, value or range of values determined by measuring contractile force in a reasonable number of experiments (e.g., an n =3 or above) in a desired cardiac tissue prepared as described herein.

The reference value can be a target, threshold or cut-off value for a given phenotypic characteristic or a known value for that phenotypic characteristic based on previous results or outcomes. For example, contractile force observed in a tissue can be quantified and then compared to an interger or range thereof, where above a given threshold the tissues are considered functional or mature cardiac tissues. The reference value can provide a metric for the quality of the systems, devices, or methods described herein. In one embodiment, the phenotypic characteristic is selected from the group consisting of gene or protein expression, electrophysiological function, structural properties, and contractile function.

One of skill in the art can appreciate that there are many types of reference levels, reference values, and appropriate controls. The type of reference level, reference value, or appropriate control is not limited to those described above and serves as a method for comparing the performance, phenotypic characteristics, or differentiation of the cardiomyocytes and cardiac tissues described herein. One of ordinary skill in the art can readily determine an appropriate control, reference level, or reference value for a given study.

Kits

Another aspect of the technology described herein relates to kits for maturing cardiomyocytes in vitro, kits for screening a candidate agent, and/or kits for assessing cardiotoxicity of a given agent. Described herein are kit components that can be included in one or more of the kits described herein. Typically, a kit as described herein will comprise, at a minimum, a device as described herein and instructions for use therefor. The device can comprise heads/caps that are pre-coated as described herein. Alternatively, the kit can comprise a device with uncoated heads/caps and further comprise an agent for coating the device heads and instructions on how to coat the device heads. Whether a device is provided with the heads coated or uncoated can have an impact on the shelf stability of the device, thus for longer stability it is contemplated that the device in the kit is uncoated for maximum shelf life.

In some embodiments, the components described herein can be provided singularly or in any combination as a kit. The kit includes the components described herein, e.g., a device or system as described herein, composition(s) for coating heads of the pillars of the device, a compound or cocktail of compounds or reagents for differentiating a human stem cell to cardiomyocyte etc. Such kits can optionally include one or more agents that permit the detection of a cardiac progenitor cell marker or a cardiac cell marker or set thereof. In addition, the kit optionally comprises informational material.

In some embodiments, the compound in the kit can be provided in a watertight or gas tight container which in some embodiments is substantially free of other components of the kit. For example, a signaling pathway or differentiation pathway modulating compound can be supplied in more than one container, e.g., it can be supplied in a container having sufficient reagent for a predetermined number of differentiation reactions, e.g., 1, 2, 3 or greater. One or more compounds (including those used to coat the heads of the pillars in the device) as described herein can be provided in any form, e.g., liquid, dried or lyophilized form. It is preferred that the compound(s) described herein are substantially pure and/or sterile. When the one or more signaling pathway modulating compounds described herein is provided in a liquid solution, the liquid solution preferably is an aqueous solution, with a sterile aqueous solution being preferred. When a compound described herein is provided as a dried form, reconstitution generally is by the addition of a suitable solvent. The solvent, e.g., sterile water or buffer, can optionally be provided in the kit.

The informational material can be descriptive, instructional, marketing or other material that relates to the methods described herein and/or the use of a compound(s) described herein for the methods described herein. The informational material of the kits is not limited in its form. In one embodiment, the informational material can include information regarding the proper use of the device or system described herein, production of the compound, molecular weight of the compound, concentration, date of expiration, batch or production site information, and so forth.

In another embodiment, the informational material can include instructions for differentiating a human stem cell to a human cardiomyocyte. Alternatively, the informational material can include instructions for screening a candidate agent for treating a cardiac disease or disorder.

In addition to a compound(s) described herein, the composition of the kit can include other ingredients, such as a solvent or buffer, a stabilizer, a preservative, and/or an additional agent, e.g., for differentiating stem cells (e.g., in vitro) or for treating a condition or disorder described herein. Alternatively, the other ingredients can be included in the kit, but in different compositions or containers than a cell or signaling pathway or differentiation pathway modulating compound described herein. In such embodiments, the kit can include instructions for admixing a compound(s) described herein and the other ingredients, or for using a compound(s) described herein together with the other ingredients, e.g., instructions on combining the two agents prior to use or administration.

The kit can include a component for the detection of a marker for human cardiac progenitor cells, ES cells iPS cells, cardiomyocytes, stromal stem cells, epicardial cells, hematopoietic cells, mesenchymal stem cells, vascular endothelial cells, etc. In addition, the kit can include one or more antibodies that bind a cell marker, or primers for an RT-PCR or PCR reaction, e.g., a semi-quantitative or quantitative RT-PCR or PCR reaction. Such components can be used to assess the activation of cardiac cell-specific markers or the loss of ES cell, iPSC, or adult stem cell markers. If the detection reagent is an antibody, it can be supplied in dry preparation, e.g., lyophilized, or in a solution. The antibody or other detection reagent can be linked to a label, e.g., a radiological, fluorescent (e.g., GFP) or colorimetric label for use in detection. If the detection reagent is a primer, it can be supplied in dry preparation, e.g., lyophilized, or in a solution.

The kit will typically be provided with its various elements included in one package, e.g., a fiber-based, e.g., a cardboard, or polymeric, e.g., a Styrofoam box. The enclosure can be configured so as to maintain a temperature differential between the interior and the exterior, e.g., it can provide insulating properties to keep the reagents at a preselected temperature for a preselected time.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Some embodiments of the various aspect described herein can be described as in the following paragraphs:

1. A system for generating 3-dimensional (3D) cardiac tissues, the system comprising:
   a solid support base
   a well in the support base, the well including a lower chamber and an upper chamber;
   at least two pillars in the lower chamber operable to produce cardiac tissues across the pillars; and
   a head on top of each pillar, each of the heads protruding into the upper chamber wherein the heads are chemically treated in a sticky coating that is different from that of the pillar.
2. The system of claim 1, further comprising muscle cells, cardiomyocytes, or stem cells in the well.
3. The system of paragraph 1, wherein the pillars are flexible and permit contraction of the cells.
4. The system of any one of paragraphs 1-3, wherein the pillars are 0.01 to 2.0 millimeters (mm) in height.
5. The system of any one of paragraphs 1-4, wherein a spring constant of the pillars is 0.05-15
6. The system of any one of paragraphs 1-5, wherein the head on top of each pillar is spherically shaped.
7. The system of any one of paragraphs 1-6, wherein the head on top of each pillar includes a portion overhanging the pillar.
8. The system of any one of paragraphs 1-7, wherein the head on top of each pillar is chemically treated to promote cell adhesion.
9. The system of paragraphs 1 or 8, wherein the chemical treatment or sticky coating is one of plasma, polylysine, and/or glutaraldehyde.
10. The system of any one of paragraphs 1-9, wherein the upper chamber is larger than the lower chamber, and wherein the upper chamber includes a tapered wall in contact with the lower chamber.
11. The system of any one of paragraphs 1-10, wherein the upper chamber is cylindrically shaped and wherein the lower chamber is rectangular shaped.
12. The system of any one of paragraphs 1-11, wherein the solid support base is rectangular shaped.
13. The system of any one of paragraphs 1-12, further comprising:
    at least one additional well having a lower chamber and an upper chamber in the solid support base comprising:
    at least two pillars in the lower chamber of the another well operable to produce cardiac tissues between the pillars; and
    a head on top of each pillar, each of the heads protruding into the upper chamber of the another well.
14. The system of any one of paragraphs 1-13, further comprising an extracellular matrix in the well.
15. The system of any one of paragrapha 1-14, wherein the extracellular matrix is selected from the group consisting of: collagen, fibronectin, fibrinogen, polylysine, vitronectin, laminin, elastin, tenascin, and Matrigel®.
16. The system of any one of paragraphs 1-15, wherein the solid support base is fabricated from polydimethylsiloxane (PDMS), polyurethane (PU), or poly(ethylene glycol) (PEG).
17. The system of any one of paragraphs 1-16, wherein the PDMS elastomer to PDMS base ratio is 1:5, 1:10, or 1:20.
18. The system any one of paragraphs 1-17, further comprising a stimulator having an electrode that generates an electrical stimulus to the well and/or pillars.
19. The system any one of paragraphs 1-18, further comprising a measurement device operable for measuring contractile function of the tissue generated in the well.
20. The system of any one of paragraphs 1-19, further comprising a device for measuring the electrical function of the tissue.
21. The system of any one of paragraphs 1-20, further comprising cells adhered to the pillars to form the tissue spanning across the pillars.
22. The system of any one of the paragraphs 1-21, further comprising a petri dish, wherein the solid support base is adhered to the petri dish.
23. A device for generating 3-dimensional (3D) cardiac tissues, the device comprising:
    a solid support base having a top surface;
    a plurality of wells accessible through the top surface, each of the wells including a top well and a lower base well;
    at least two pillars in each of the lower base wells operable to produce cardiac tissues across the pillars; and
    a head on top of each pillar, each of the heads protruding into the corresponding top wells.
24. A method of maturing cardiomyocytes in culture, the method comprising, culturing cardiomyocytes in the device or system of any one of paragraphs 1-23 and exposing the cardiomyocytes to electrical stimulation, thereby maturing the cardiomyocytes in culture.
25. The method of paragraph 24, wherein the cardiomyocytes are stem cell-derived cardiomyocytes.
26. The method of paragraph 25, wherein the stem cell-derived cardiomyocytes are differentiated from an induced pluripotent stem cell (iPS cell) or an embryonic stem cell.
27. The method of any one of paragraphs 25-26, wherein the stem cell-derived cardiomyocytes are derived from a subject with a muscular disease or disorder.
28. The method of paragraph 27, wherein the muscular disease or disorder is genetic cardiomyopathy, hypertrophic cardiomyopathy, dilated cardiomyopathy, cardiac arrhythmia, arrhythmogenic right ventricular dysplasia (ARVD), Duchenne muscular dystrophy, and diabetic cardiomyopathy.
29. The method of any one of paragraphs 24-28, further comprising, co-culturing the cardiomyocytes with stromal stem cells.
30. The method of any one of paragraphs 24-29, wherein the cardiomyocytes are human cardiomyocytes.
31. The method of any one of paragraphs 24-30, wherein the cardiomyocytes are genetically modified.
32. The method of any one of paragraphs 24-31, further comprising detecting at least one phenotypic characteristic of the cardiomyocytes.
33. The method of any one of paragraphs 24-32, wherein the electrical stimulation frequency is 0.1 Hz or more, 0.5 Hz or more, 1 Hz or more, 1.8 Hz or more, 2 Hz or more, 2.7 Hz or more, 3 Hz or more, 3.5 Hz or more, 4 Hz or more, 4.8 Hz or more, 5 Hz or more, 5.2 Hz or more, 6 Hz or more, 7 Hz or more, 8 Hz or more, 9 Hz or more, or 10 Hz.

34. The method of any one of paragraphs 24-33, wherein the electrical stimulation is conducted 4 days after the stem cell-derived cardiomyocytes are cultured in the device or system of any one of paragraphs 1-23.

35. The method of any one of paragraphs 24-34, wherein the electrical stimulation is conducted for 6 hours per day for three days.

36. A method of evaluating cardiotoxicity of an agent, the method comprising:
culturing cardiomyocytes in the device or system of any one of paragraphs 1-23;
contacting cardiomyocytes with the agent; and
detecting modulation of at least one phenotypic characteristic associated with cardiotoxicity in the cardiomyocytes;
wherein the modulation of at least one phenotypic characteristic associated with cardiotoxicity compared to a reference level indicates that the agent is cardiotoxic.

37. The method of paragraph 36, wherein the agent is selected from the group consisting of a small molecule, an antibody, a peptide, a genome editing system, and a nucleic acid.

38. The method of any one of paragraphs 36-37, wherein the phenotypic characteristic is associated with impaired contractile function, decreased beat rate, impaired electrical function, impaired metabolic function, a decrease in cell viability, or a decrease in expression of a cardiac marker.

39. The method of any one of paragraphs 36-38, wherein cardiotoxicity of an agent is indicated by the agent's effect on one or more of: cell viability, cell size, sarcomere length, organization of sarcomeres within a tissue, a biopotential or electrical property of a population of cardiomyocytes, mitochondrial function, gene expression, beat rate, beat strength, and contractility.

40. A disease model comprising a cardiomyocyte prepared by the method of any one of paragraphs 24-35, wherein the cardiomyocyte is derived from a subject with a muscular disease or disorder, or wherein the cardiomyocyte genetically modified such that the cardiomyocyte expresses a disease phenotype.

41. The disease model of paragraph 40, wherein the muscular disease or disorder is genetic cardiomyopathy, hypertrophic cardiomyopathy, dilated cardiomyopathy, cardiac arrhythmia, arrhythmogenic right ventricular dysplasia (ARVD), Duchenne muscular dystrophy, and diabetic cardiomyopathy.

42. The disease model of any one of paragraphs 40-41, wherein the cardiomyocytes are human cardiomyocytes.

43. The disease model of any one of paragraphs 40-42, wherein the cardiomyocytes are stem cell-derived cardiomyocytes.

44. The disease model of any one of paragraphs 40-43, wherein the cardiomyocytes are genetically modified.

45. The disease model of paragraph 44, wherein the genetic modification is a mutation in the gene or RNA encoding the polypeptide, beta-myosin heavy chain (β-MHC).

46. The disease model of paragraph 45, wherein the genetic modification is an arginine substituted for a glutamine at position 403 (R403Q).

47. A kit comprising the device or system of any one of paragraphs 1-23, and packaging materials therefor.

48. The kit of paragraph 47, further comprising cell culture medium and instructions to permit preparation of mature cardiomyocytes and/or stem cell-derived cardiomyocytes.

49. The kit of any one of paragraphs 47-48, wherein the cardiomyocytes are human.

50. The kit of any one of paragraphs 47-49, wherein the cardiomyocytes are derived from a subject with a muscular disease or disorder.

51. A method for generating cardiac tissues, comprising:
providing a device including at least one well including a plurality of pillars coupled to the bottom surface of each of at least one well, each pillar including a head at a terminal end thereof, wherein each of at least one well is surrounded by a plurality of ridges, wherein the heads are chemically treated in a sticky coating that is different from that of the pillar;
immersing the device in a suspension of cardiomyocytes;
delivering the suspension of cardiomyocytes into the at least one well;
polymerizing the suspension to form a matrix;
culturing the cardiomyocytes over time, to spontaneously compact the matrix, wherein the pillars anchor the contracting matrix, constraining the contraction of the matrix to form a band of cardiac tissue that spans across the pillars, thereby allowing the cardiomyocytes to mature; and
measuring a contractile function of the band of cardiac tissue,
wherein measuring comprises: imaging the device, over time, to acquire image data determining a force exerted on the pillars based on at least the image data and a spring constant corresponding to each pillar; and identifying a contractile function of the band of cardiac tissue based on at least the determined force,
wherein the contractile function includes one or more of beat frequency, contraction duration, change in beat frequency over time, change in contraction duration over time, or variance in any of these phenotypic characteristics.

52. The method of paragraph 51, further comprising, chemically treating the head at the terminal end of the pillar to promote cell adhesion.

53. The method of any one of paragraphs 51-52, wherein the chemical treatment or sticky coating is one of plasma, poly-lysine, and/or glutaraldehyde.

54. The method of any one of paragraphs 51-53, further comprising muscle cells, cardiomyocytes, or stem cells in the well.

55. The method of any one of paragraphs 51-54, wherein the cardiomyocytes are stem cell-derived cardiomyocytes.

56. The method of paragraph 55, wherein the stem cell-derived cardiomyocytes are differentiated from an induced pluripotent stem cell (iPS cell) or an embryonic stem cell.

57. The method of paragraph 55, wherein the stem cell-derived cardiomyocytes are derived from a subject with a muscular disease or disorder.

58. The method of any one of paragraphs 51-57, wherein the cardiomyocytes are human cardiomyocytes.

59. The method of any one of paragraphs 51-58, wherein the cardiomyocytes are genetically modified.

60. The method of any one of paragraphs 51-59, further comprising, stimulating and/or measuring the electrical function of the cardiac tissue.

61. The method of paragraph 60, wherein the electrical stimulation frequency is 0.1 Hz or more, 0.5 Hz or more, 1 Hz or more, 1.8 Hz or more, 2 Hz or more, 2.7

Hz or more, 3 Hz or more, 3.5 Hz or more, 4 Hz or more, 4.8 Hz or more, 5 Hz or more, 5.2 Hz or more, 6 Hz or more, 7 Hz or more, 8 Hz or more, 9 Hz or more, or 10 Hz.
62. The method of any one of paragraphs 51-61, wherein the cardiac tissues are viable for up to 7 days or more, 14 days or more, 21 days or more, 28 days or more, or 35 days.
63. The method of any one of paragraphs 51-62, further comprising, prior to providing a device, making the device using a 3D-printed mold and a curable polymer.
64. The method of paragraph 63, wherein the curable polymer is PDMS, polyurethane (PU), or poly(ethylene glycol) (PEG).
65. The method of paragraph 64, wherein the PDMS elastomer to PDMS base ratio is 1:5, 1:10, or 1:20.
66. The method of any one of paragraphs 51-65, wherein the pillars are 0.01 to 2.0 millimeters (mm) in height.
67. The method of any one of paragraphs 51-66, wherein the pillars are 0.6 mm apart or more, 0.7 mm apart or more, 0.8 mm apart or more, 0.9 mm apart or more, 1.0 mm apart or more, 1.1 mm apart or more, 1.2 mm apart or more, 1.3 mm apart or more, 1.4 mm apart or more, 1.5 mm apart or more, 2.0 mm apart or more, 2.5 mm apart or more, or 3.0 mm.
68. The method of any one of paragraphs 51-67, wherein a spring constant of the pillars is 0.05-15 $\mu N/\mu m$.
69. The method of any one of paragraphs 51-68, wherein the head includes a portion overhanging the pillar.
70. The method of any one of paragraphs 51-69, wherein the suspension of cardiomyocytes comprises stem cell-derived cardiomyocytes are a different stages of maturity.
71. The method of any one of paragraphs 51-70, wherein the suspension of cardiomycotyes further comprises co-culture with stromal cells.
72. The method of any one of paragraphs 55 or 70, wherein the stem cell-derived cardiomyocytes have a purity of 50% or more, 60% or more, 70% or more, 80% or more, 90% or more, or are 100% pure.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Studies to gain mechanistic understanding of heart dysfunction based on animal and traditional cell culture models have significant limitations. Animal models are low throughput and fail to recapitulate many aspects of human cardiac biology, and 2D culture models utilizing human induced pluripotent stem cell derived cardiomyocytes (iPSC-CMs) are higher throughput but fail to incorporate one or more in vivo parameters, such as 3D architecture, electrical pacing and mechanical constraint. High throughput 3D tissue platforms could better recapitulate the in vivo microenvironment of cardiac tissue. Previous studies demonstrated an approach to build 3D cardiac tissues based on photolithography-based fabrication of a MEMS device, but design limitations prevented further iterations. In this study, a 3D printing approach was used to engineer iPSC-CM-derived cardiac tissues with different form factors. Tissues generated in this platform increased in lifespan compared to the first-generation platform by more than 100%. When modeling mutations associated with genetic cardiomyopathy, functional and structural differences were observed between tissues composed of wild-type and mutant iPSC-CMs. These findings indicate that this micro-device platform can be used for both mechanistic and drug discovery studies.

Heart Disease and Genetic Cardiomyopathies

Cardiovascular disease is the leading cause of death in the US[1]. Cardiovascular disease can be developed, such as coronary heart disease, hypertension and arrhythmia, or genetic, such as genetic cardiomyopathy. Genetic cardiomyopathies are a group of genetic heart muscle diseases that affect proteins in cardiomyocytes, the force generating muscle cells of the heart.

There are several different types of cardiomyopathies. Dilated cardiomyopathy is characterized by heart wall thinning and systolic dysfunction caused by mutations that affect various cellular components and pathways related to tissue function and structural organization[2]. Hypertrophic cardiomyopathy (HCM) is characterized by thickening of the heart wall tissue, fibrosis and myocyte disorganization[2]. It is most commonly caused by mutations in the β-myosin proteins in sarcomeres, the contractile units in cardiomyocytes[3]. The R403Q mutation, one of the most widely studied mutations linked to HCM, is a point missense mutation in the β-myosin heavy chain (MHC) that converts an arginine residue to glutamine[4,5]. It is mechanistically unclear how this mutation causes HCM's clinical phenotype, which includes fibrosis and tissue disorganization, in patients, partly due to a lack of human models. Animal models have provided valuable insights into the mechanisms of this disease however there are fundamental differences between animal and human cardiomyocytes. For example, adult human cardiomyocytes predominately express β-MHC as opposed to mouse cardiomyocytes, which predominately express α-MHC[6]. This difference in myosin isoform expression can hamper accurate study of HCM pathogenesis.

A Need for Increasing Cardiomyocyte Maturity

Recent advances in human induced pluripotent stem cell (iPSC) technology have provided a good source of cardiomyocytes, leading to the development of various 2D and 3D in vitro models. However, newly generated iPSC-CMs maintain an immature phenotype in which they are smaller in size, lack of t-tubules, have underdeveloped calcium handling properties, and a lower β-myosin content[7,8]. A higher β-myosin content may be neccessary to model HCM since most of the disease-causing mutations are found in β-MHC. Time in culture of iPSC-CMs has been shown to enhance β-myosin content and maturation, but they still do not fully express the adult phenotype. In one study, iPSC-CMs were cultured in 2D for 120 days to achieve an increase in size, sarcomere organization, and contractile performance'. Another study developed a method alternating between 2D and 3D culture over the course of one year to enhance gene expression and ion channel function[10]. While these platforms have shown an increase in iPSC-CM maturity, they still lack features that exist in 3D cardiac tissue, such as myofibrillar architecture, t-tubules. Thus, 2D platforms are unable to faithfully recapitulate the 3D microenvironment found in native heart tissue.

3D Platforms for Generating Cardiac Tissues 3D culture platforms can provide better conditions for generating functionally mature iPSC-CM cardiac tissues. Several platforms have been developed to generate 3D cardiac tissues that model human heart tissue. Desroches et al. developed a high-throughput platform to generate 822 3D tissues per device composed of about 1200 cells per tissue, but their system lacks mechanical loading, resulting in poorly developed sarcomeres[11]. Zimmerman et al. developed a technique to generate cardiac tissue in the shape of a ring around two posts, simulating the mechanical loading present in vivo[12]. While the system is a successful platform recapitulating the 3D microenvironment for engineering cardiac tissues, each tissue construct requires over 1.5 million cardiomyocytes and an extensive preparation process, making it a low-throughput system. Previously, a µ-tug microwell system was developed that can generate 100 3D cardiac tissues, composed of 500 cells each, per device[13]. This high-throughput platform utilizes a low number of cells and provides mechanical loading as well as boundary conditions on the tissues. The system also allows the assessment of real time assessment of isotonic muscle contraction. The tissues are also thin, overcoming the diffusion limit to produce viable tissues. However, tissues generated in this platform experience a short lifespan and the experimental preparation process limits the flexibility of the extracellular matrix (ECM) composition, so it is not an ideal platform for long-term tissue maturation, which can be neccessary for certain disease modeling applications[14.]

Significance of Electrical Stimulation for Cardiac Tissue Maturation

In addition to culture in 3D platforms, prolonged electrical stimulation can also increase the maturation of iPSC-CMs. Electrical stimulation can increase cell alignment and structural organization, enhance $Ca^{2+}$ handling, and improve the electrophysiological properties of cardiomyocytes[15,16]. A frequency ramp-up regimen of iPSC-CM tissues over the course of 7 days has been shown to exhibit increased electrophysiological properties, such as lower excitation threshold and increased conduction velocity, as well as improve sarcomeric organization, producing constructs that present a more adult-like phenotype[16]. Thus, it can be advantageous to develop a platform that is compatible with electrical stimulation equipment for prolonged stimulation of iPSC-CM tissues to improve their functional maturity and phenotype.

This study aims to develop a new high throughput platform to generate 3D cardiac tissues with increased tissue lifespan for modeling HCM. This platform can generate a high yield of tissues with a lifespan of two weeks. In addition, the study aims to develop an electrical stimulation regimen and determine whether it increases the functional maturity of tissues generated in the proposed platform. The platform can be used to generate tissues to model a HCM mutation. Tissues generated through this engineered platform can be used to model functional and morphological differences between tissues composed of wild-type (WT) cardiomyocytes and cardiomyocytes harboring the R403Q mutation ($403^{+/-}$).

Example 1

Engineered Platform to Generate 3D Cardiac Tissues for Modeling Genetic Cardiomyopathies Prior high-throughput µ-tissue platforms developed in the laboratory provide a strong candidate system for short-term tissue experimentation but is not an option for long-term tissue maturation, which can be neccessary for certain disease modeling applications and maturation protocols. Development of a new platform and procedure was necessary to generate a high yield of cardiac tissues with a lifespan of two weeks. A prototype mold was designed in SolidWorks with several design conditions, which included two different microwell geometries, three cap or head geometries and three post heights (FIG. 1). One microwell design featured a rectangular base well in which the pillars are housed, with a larger cylindrical top well for cell culture medium. The other microwell design featured a rectangular base well that ended at the bottom of the caps of the posts, with a larger volume of space around the caps, and a larger cylindrical top well for cell culture medium. This design was created to determine if having more space for media exchange around the tissue was beneficial.

The three chosen cap geometries consisted of a drafted rectangular cap and a spherical cap each with a 50 µm overhang, and a spherical cap whose diameter was equal to the width of the pillar and thus had no overhang. Rectangular caps were adapted from the µ-tug platform. Tissues in the µ-tug platform displayed tears on the inner interface of the pillars, and a thinning of the tissue at the inner corners of the caps. Thus, spherical caps were tested to minimize the formation and size of those inner holes in the tissue. The spherical caps were postulated to promote a more even distribution of stress than the rectangular caps, thus decreasing concentrations of stress at specific points of the tissue which could compromise the tissue's structural integrity.

Three different post heights were tested to change the spring constant of the pillars[13] (Table 1). The posts simulate static mechanical loading on the tissue, so posts that are too stiff for the tissue to displace adequately predispose the system to induce increased afterload[17].

The spacing in the platform was designed to be compatible with a microscope for real time force measurements as well as with the IonOptix C-Pace EP Culture Pacer, a commercially available product used for electrical stimulation of cell cultures. The mold generates three repeats of the platform, with lines between each device to indicate where to cut and a "T" marking to indicate the orientation of the different design conditions. Each final device features a 2×6 array of the different design conditions.

TABLE 1

Spring constant of the post at different total heights and material stiffnesses.

|  | 1:10 PDMS Ratio | | | 1:20 PDMS Ratio | | |
| --- | --- | --- | --- | --- | --- | --- |
| Total Post Height (mm) | 1.1 | 1.2 | 1.5 | 1.1 | 1.2 | 1.5 |
| Spring Constant (uN/um) | 8.86 | 6.74 | 3.35 | 3.21 | 2.68 | 1.99 |

Initial Process for Generating Engineered Cardiac Tissues

Figure 1A:
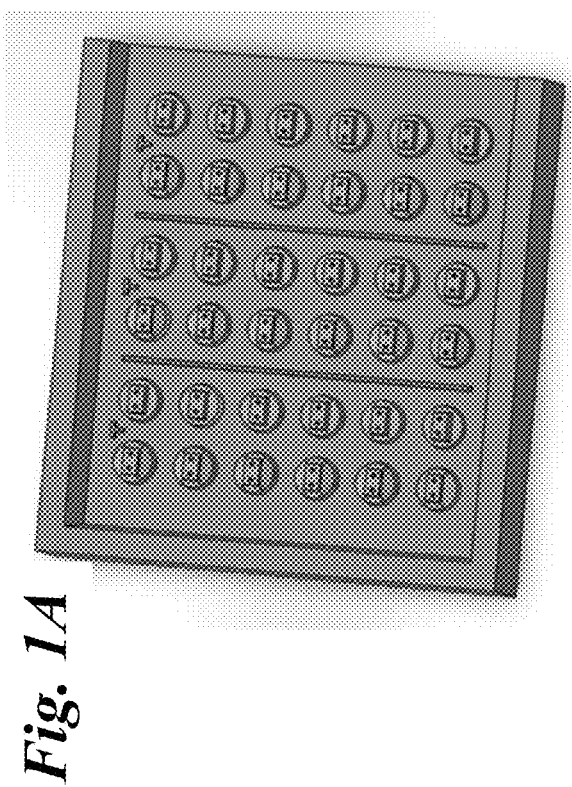
Figure 1B:
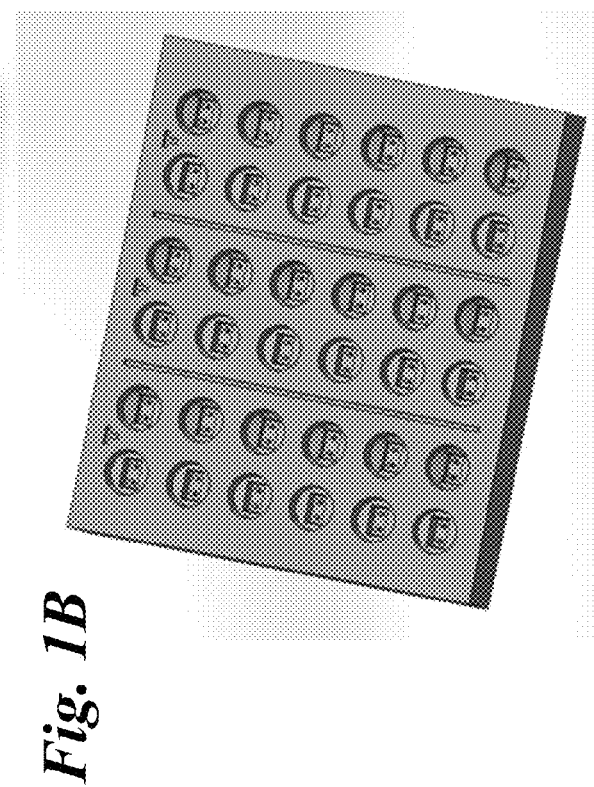

The prototype mold was 3D printed using stereolithography by Protolabs (FIG. 1A). Polydimethylsiloxane (PDMS) was used to cast the final positive mold for generating cardiac tissues (FIG. 1B). PDMS was made at a 1:10 ratio and poured onto the negative 3D printed mold and cured at 60° C. for 24 hours. The PDMS mold was then removed from the negative mold and cut into three strips along the indicated lines, creating the final device. Each device was attached to a 60 mm petri dish using PDMS and cured at 60° C. for 24 hours. The devices were UV sterilized for 15 minutes prior to seeding.

iPSCs were differentiated using a standardized protocol[18]. Briefly, iPSCs were cultured in Rosewell Park Memorial Institute (RPMI) medium supplemented with B-27 minus insulin (RPMI-B27-) for 8 days. At the start of differentiation, iPSCs were treated with CHIR99021, a glycogen synthase kinase 3 (GSK3) inhibitor, for 24 hours. 48 hours after GSK3 inhibition, the cells were treated with IWP4, a Wnt inhibitor, for 24 hours in RPMI-B27-. On the 9$^{th}$ day of differentiation, cell medium was changed to RPMI supplemented with B-27 plus insulin (RPMI-B27+). Once the iPSC-CMs started to spontaneously contract, they were subjected to metabolic selection for 2 days by replacing glucose in the cell medium with 4mM lactate. iPSC-CMs were then replated and maintained in culture in RPMI-B27+ until experimentation.

Tissues composed of iPSC-CMs and stromal cells were cultured in H1 Media, composed of high glucose Dulbecco's Modified Eagle Medium (DMEM) supplemented with 10% fetal bovine serum (FBS, Sigma), 1% Gibco GlutaMAX, 1% Gibco MEM Non-Essential Amino Acids and 1% Penicillin Streptomycin.

To generate tissues, a thrombin solution composed of H1 media and 0.6 U thrombin per mg fibrinogen was added to each well and centrifuged at 3000 RPM for 1.5 minutes to uniformly distribute it across the bottom of the base well. Then, a reconstitution mixture of cells and ECM composed of 84% iPSC-CMs and 16% neonatal human cardiac fibroblasts (NHCF-V), H1 Media, 2.5 mg/ml fibrinogen and 12.5% v/v Matrigel were added to each well and the device was shaken up/down and left/right to distribute the mixture in the wells. The devices were placed in a 37° C., 5% $CO_2$ incubator for 30 minutes for fibrinogen polymerization and then H1 media with 10 µM Y27632 was added to each well. The final volume of media in each well is about 50 µl, making it prone to evaporation. Thus, 1× phosphate buffer solution (PBS) was added into the petri dish to mitigate media evaporation.

Chemical Treatment of the Caps

To further increase tissue lifespan and yield, a cap chemical treatment (CCT) method was developed to increase cell adhesion to the PDMS caps. A CCT platform was developed composed of rectangular wells which could be aligned with the PDMS mold so that only the caps of each pillar would be in the CCT platform's rectangular well space, allowing for only the caps of the pillars to be chemically treated (FIG. 2). The devices were plasma treated for 30 seconds. The CCT platform's wells were filled with 0.01% poly-lysine and the caps were treated for 2 hours and then washed with PBS. The caps were then treated with 0.1% glutaraldehyde for 15 minutes. Then, the devices were washed thoroughly in PBS and incubated in PBS in the fridge overnight.

Optical Analysis

To quantify tissue forces, bright field images were taken at 4× on a Nikon Eclipse Ti microscope. The microscope is housed in a chamber with environmental control set to 37° C. and 5% $CO_2$. The displacement of the pillars can be tracked using the SpotTracker plug-in on ImageJ. The displacement values were then run through a custom MATLAB script to compute twitch force[14]. The spring constant of the pillars was theoretically calculated[13] (Table 1). In the final platform design fabricated in 1:20 PDMS, the spring constant of the pillar was calculated to be k=2.677.

Immunofluorescence

Tissues were fixed in 4% paraformaldehyde for 30 minutes. Tissues were permeabilized with 0.1% Triton X in PBS for 1 hour. Primary antibodies were added and incubated overnight at 4° C. Then, tissues were washed three times with PBS and the secondary antibodies were added and incubated for two hours at room temperature. Tissues were further incubated with the secondary antibodies at 4° C. overnight. Tissues were then washed three times with PBS and imaged.

Testing of Design Conditions and Optimization of the Tissue Generation Process

The goal of this study, in part, was to generate a high yield of tissues with a lifespan of two weeks in the new platform. Using the initial tissue generation protocol, tissue lifespan was less than one week and produced a very low yield (<10%) across all design conditions. Parameters such as ECM composition, seeding density, cell medium composition, and orientation of the device at different stages of the process were optimized to increase tissue lifespan and yield.

Seeding densities ranging between 25,000-75,000 cells/well were tested. The cells were seeded in a fibrin-based hydrogel, which has been reported to be a favorable material for cardiac tissue engineering applications due to its degradability and mechanical properties[1]. Without wishing to be bound by theory, it was hypothesized that the rate of fibrin degradation exceeded the rate of cell ECM production, leading to a low tissue lifespan and yield. Combinations of fibrinogen, thrombin and Matrigel™ concentrations were tested to determine the optimal mixture. In addition, aprotinin, a fibrinolysis inhibitor, was added to the culture medium to slow down the fibrin degradation rates. With these changes, tissue lifespan increased to over one week.

While the formation of tissues in the devices was successful, the tissues were forming around the base of the pillars as opposed to around the caps, which is necessary for proper data measurements and analysis. So, the orientation of the device during the seeding process was varied. Inversion of the device only during polymerization and upright orientation of the device during polymerization followed by inversion of the device post-polymerization for several days were tested. Inversion of the device during only polymerization produced mixed results where some tissues formed in various locations relative to the caps. So, the initial seeding volume was adjusted. Originally, the total volume of the seeding mixtures exceeded the volume capacity of the base well. So, the seeding volume was reduced so that the mixture would fill the base well to the middle of the cap. With the changes in seeding volume and device orientation, the tissues compacted around the caps and showed an increased lifespan to 1.5 weeks in the wells featuring rectangular and spherical caps with the overhang but not in the wells featuring spherical caps with no overhang.

The formation of holes on the inner interface of the cap to the tissue were observed. To improve the compaction of the tissues around the caps, the stromal cells were switched from NHCF-V to human mesenchymal stem cells (hMSCs). The cell mixture was adjusted to 90% iPSC-CMs and 10% hMSCs. With this change, the tissue lifespan increased to two weeks.

The spherical caps with no overhang produced the lowest yield of tissues with a lifespan of two weeks. It was concluded that the cap overhang is necessary for the tissues to stay on the posts and thus the non-overhanging design was removed from further consideration. With the optimization of the tissue generation process, tissues in this microwell design featuring spherical caps on the posts produced the highest yield of tissues with a lifespan of two weeks. In the well design featuring a larger slanted space around the caps, the tissues tended to adhere to the slanted wall. The 3D printed mold is fabricated in layers and so the slanted wall is not a smooth surface, which could lead the cells to preferentially adhere to that rougher surface. PDMS ratio was adjusted to 1:20 to decrease pillar stiffness.

Final Platform Design

The final platform features spherical caps on posts within individual microwells composed of a rectangular base well and a larger top cylindrical well (FIG. 3). The individual microwell design allows for each well to be seeded individually so multiple conditions can be tested in one device, increasing the flexibility of the platform for experimental conditions. The individual microwells also provide increased flexibility in ECM composition during cell seeding, allowing for the generation of cardiac tissues in a fibrin-based hydrogel. The negative mold generates six final PDMS tissue platforms, each featuring a 2×3 array of microwells marked with a "||" to denote the top (FIGS. 3A-B). Each is then adhered to a 35 mm petri dish to form the final device for cardiac tissue generation (FIG. 4B). The spacing within the platform is compatible with a microscope for optical imaging for force measurements as well as the IonOptix C-Pace EP Culture Pacer, providing the flexibility to electrically stimulate the tissues and develop a regimen to promote tissue functional maturity.

Final Tissue Generation Process

The PDMS platform mold is subjected to CCT one day prior to experimentation. A thrombin solution is added to each base well and the device is centrifuged at 3000 RPM for 1.5 minutes. A reconstitution mixture of 50,000 cells/well (90% iPSC-CMs and 10% hMSCs) in 4 mg/ml fibrinogen, 0.4 U thrombin per mg fibrinogen, and 10% Matrigel is added to each base well, and the total volume fills the base well to halfway up the cap. Devices are shaken up/down and left/right to distribute the reconstitution mixture. Devices are inverted during polymerization and then kept upright for the duration of the experiment. Tissues are cultured in H1 media with 0.033 mg/ml aprotinin and 10 uM Y27632 for the first two days and then Y27632 is removed from the media for the rest of the experiment.

Figure 4A:
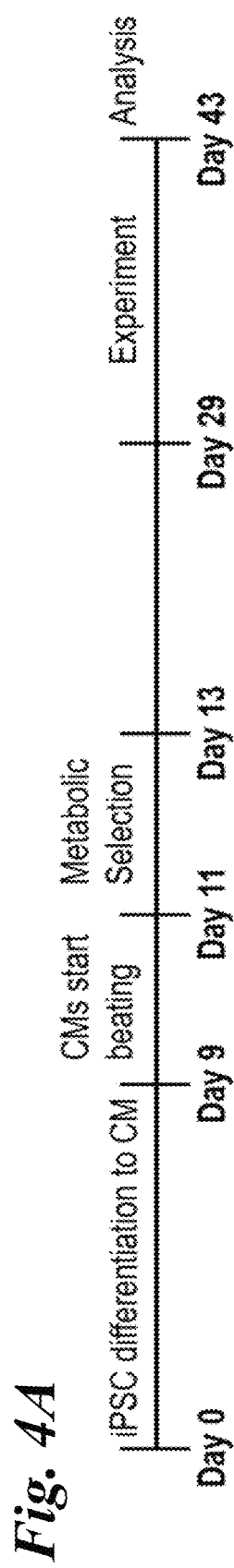
FIGS. 4A-4B show an experimental timeline and seeding process.
Figure 4B:
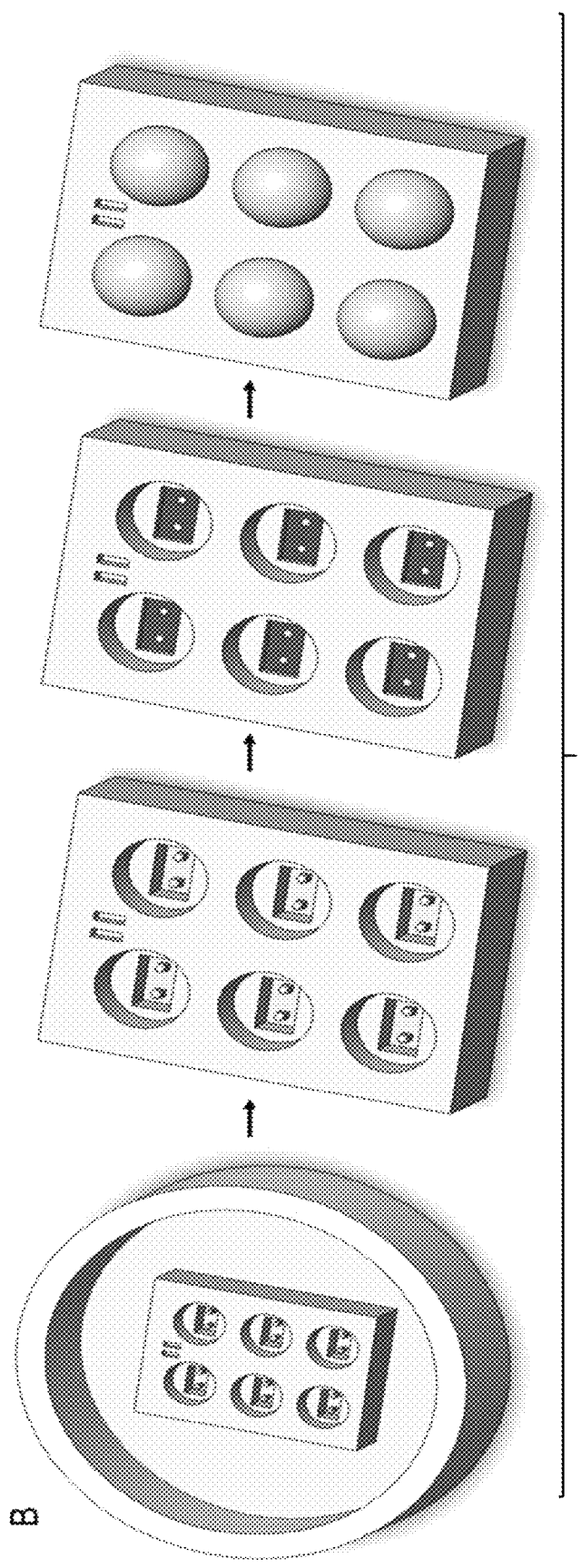

Provided herein is an optimized tissue generation process for the new platform described herein (FIG. 4). The thrombin solution and reconstitution mixture volume fills the base well to halfway up the caps, and the device is inverted during polymerization and then kept upright for the duration of the experiment (FIG. 4B). Over time of cultivation, the cells compact the hydrogel construct around the caps, and the resulting tissue spontaneously contracts as a unit by day 5. The addition of aprotinin from the beginning of the process increased the tissue lifespan by slowing down the fibrin hydrogel degradation (not shown). Also provided herein is a method to differentially treat the caps of the pillars to promote cell-substrate adhesion. The combination of the tissue generation process and CCT produces a tissue yield of about 88% at 2 weeks. Without the CCT, the tissue yield was less than 50%.

Function and Structure of Tissues in the New Platform

Figure 5A:
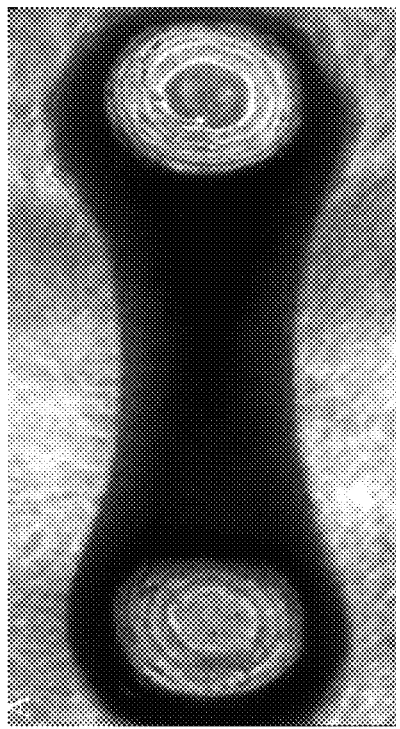
FIGS. 5A-5C show cardiac tissue function.
Figure 5C:
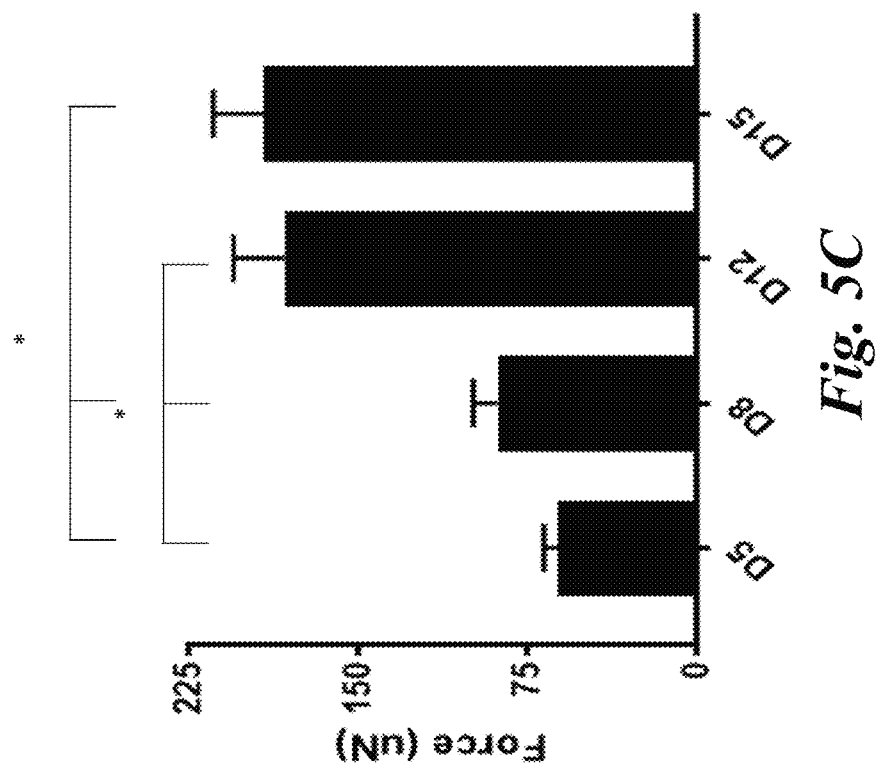
Figure 5B:
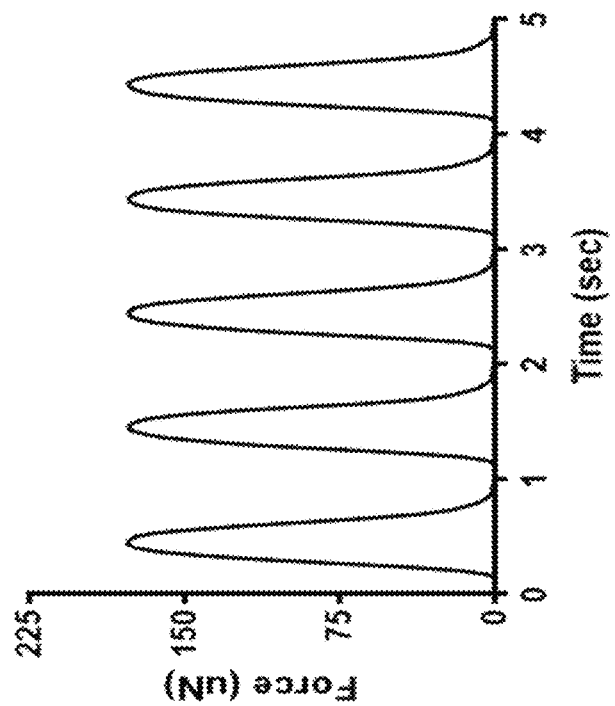

Tissues were generated in the platform using the finalized tissue generation protocol (FIG. 5A). Optical videos were taken of the tissues while electrically stimulated at 1 Hz for data analysis. The analysis reveals that the tissues can follow the applied electrical stimulation, producing a consistent force output (FIG. 5B). Tissues start to spontaneously contract by Day 5 and twitch force increases over time (FIG. 5C). Immunofluorescence staining and imaging reveals robust aligned cardiomyocyte sarcomere formation and collagen deposition (FIG. 6).

This new platform is a high-throughput system that produces a high yield of iPSC-CM tissues with a lifespan of two weeks. Some tissue failures are attributed to human error, such as pipetting error during the addition of the reconstitution mixture to the wells, resulting in the formation of bubbles and an incorrect seeding density. For these studies, the experimental timeline is two weeks; however, further studies can be conducted to determine the maximum tissue lifespan in this new platform.

While tissues present aligned sarcomere formation and collagen deposition, the alignment can be further optimized, if desired. iPSC-CM tissues were generated with GFP-labeled fibrinogen. Fluorescent imaging shows that fibrin is still present in the tissues after two weeks of culture. Additional studies on optimal aprotinin concentration over the duration of culture can further increase structural alignment due to increased tissue compaction and remodeling.

Example 2

Electrical Stimulation of Engineered Tissues

While prolonged culture in a 3D platform can improve cardiomyocyte maturity, electrical stimulation can be utilized to further mature cardiomyocytes. iPSC-CM tissues subjected to a frequency ramp-up regimen over the course of 7 days have been shown to exhibit increased electrophysiological properties, such as lower excitation threshold and increased conduction velocity, as well as improved sarcomeric organization, producing constructs that present a more adult-like phenotype[16]. The new platform described in Example 1 was designed to be compatible with the IonOptix C-Pace EP Culture Pacer to allow for prolonged electrical stimulation of the tissues. Building off previous studies, an electrical stimulation regimen can be developed to increase the functional maturity and phenotype of the iPSC-CM tissues. Stimulated and non-stimulated tissues will be compared to determine the optimal electrical stimulation regimen to improve the functional maturity of the iPSC-CM tissues.

Tissues composed of iPSC-CMs and hMSCs were generated in the PDMS molds. Tissues were maintained in H1 media with 10 uM Y27632 and 0.033 mg/ml aprotinin for the first two days and then Y27632 was removed from the media for the rest of the experiment. After 5 days of pre-culture, tissues were subjected to a high frequency ramp up stimulation regimen using the IonOptix C-Pace EP Culture Pacer (FIG. 7). The tissues were subjected to a field stimulation of 1 ms pulses of 2.5 V/cm over the course of 7 days with an incremental increase of the frequency from 1 Hz to 6 Hz. Then, the tissues were subjected to an exercise regimen of different frequencies and voltages for 6 hours a day for 3 days. The tissues were kept in culture for 15 days.

Figure 9B:
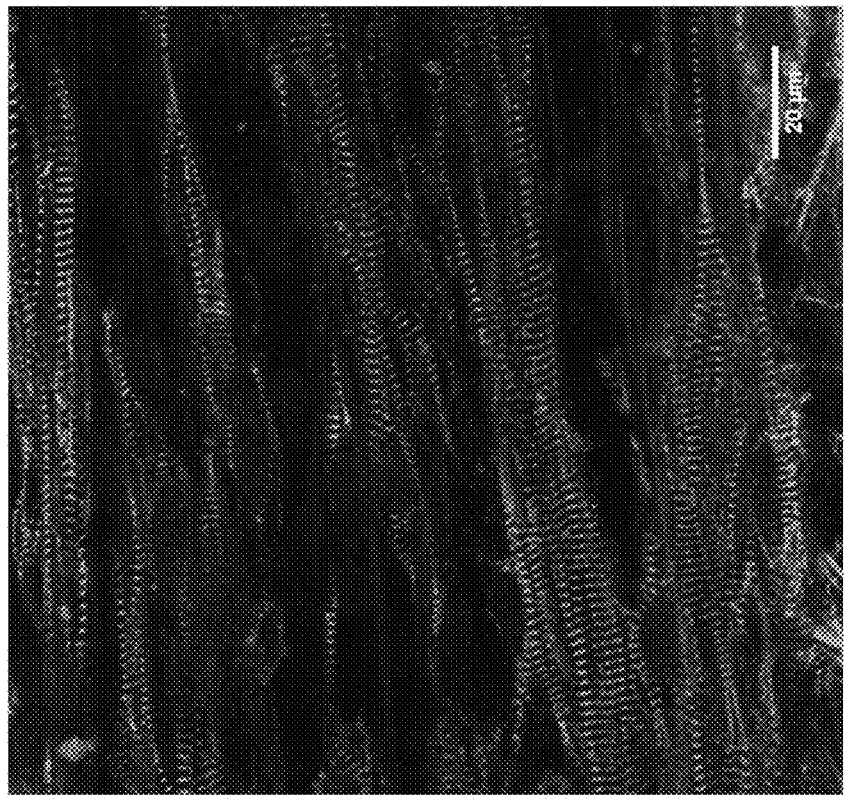
FIGS. 9A-9B show immunofluorescent images of tissue architecture after electrical stimulation.
Figure 9A:
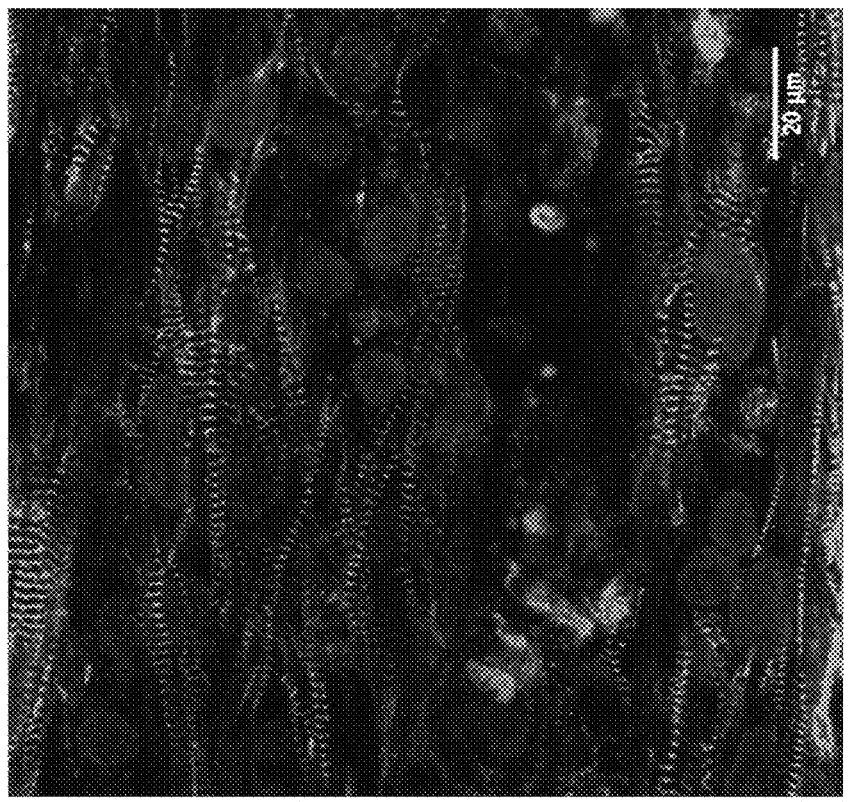

Tissues were pre-cultured for 5 days and then subjected to an electrical stimulation regimen (ES+) until day 15. Control tissues were maintained in standard culture without electrical stimulation (ES−). ES+ tissues were subjected to a ramp-up regimen in which the frequency of stimulation was increased from 1 Hz to 6 Hz over 7 days (FIG. 7). After the ramp up regimen, contractile force of ES+ tissues were slightly higher than ES− tissues but not statistically significant (FIG. 8A). Then, ES+ tissues were subjected to the exercise regimen for 3 days. At day 15, ES+ tissues exhibited the same trend of higher contractile force than ES− tissues but the difference was not statistically significant (FIG. 8A). Isoproterenol, a β-adrenergic agonist, was added to both ES+ and ES− tissues. β-adrenergic stimulation affects cardiac tissue and is related to the calcium handling properties of the cardiomyocytes[20]. ES+ tissue contractile force increased by 20.7% while ES− tissue contractile force increased by 6.8% (FIG. 8B). While both conditions were responsive to β-adrenergic stimulation, the response was not statistically significant. Immunofluorescence imaging shows robust sarcomere alignment in ES+ tissues compared to ES− tissues (FIG. 9).

The electrical stimulation regimen described herein can improve the functional maturity of the iPSC-CM tissues. The response to isoproterenol stimulation indicates that $Ca^{2+}$ handling of the ES+ tissues was improved. Without wishing to be bound by theory, the tissues' response to electrical stimulation may not have been statistically significant due to a small sample size. Additional studies can be conducted to increase the sample size and further explore the effects of this regimen. A prolonged study was conducted in which tissues were stimulated for an additional week, leading to tissue culture in the platform for 21 days with 17 days of electrical stimulation. At day 21, ES+ tissues presented with a decrease in contractile force. Additional studies can be conducted to further optimize the electrical stimulation regimen to improve the functional output after two and three weeks of culture. This drop in contractile force could also be due to reduced plasticity of the iPSC-CMs[21]. Tissues could be generated from early-stage iPSC-CMs in which they have high cell plasticity and then subjected to the stimulation regimen.

Example 3

Modeling Hypertrophic Cardiomyopathy in Engineered Tissues

In an effort to generate a clinically relevant cell model of hypertrophy, the R403Q point missense mutation, one of the most widely studied mutations linked to HCM, was selected for additional study with the compositions and methods described herein. It is still unclear how the mutation affects the function of cardiac cells and tissue and leads to the resulting clinical phenotype. Many studies have been conducted in animal-based models, and human-based models have largely focused on the effects of the mutation at the cellular and subcellular level[22]. In this work, the R403Q mutation is modeled in a human-based 3D tissue platform to study the effects of the mutation at the tissue level. Tissues composed of iPSC-CMs harboring the mutation will be generated and compared to WT iPSC-CM tissues to determine functional and morphological differences between the two.

Isogenic WT iPSCs and iPSCs harboring the R403Q mutation ($403^{+/-}$) were obtained as a gift from Drs. Christine and Jonathan Seidman. Both cell lines were differentiated using the protocol described previously. Flow cytometry was run on differentiated populations to determine purity between cell lines. Population purity was high in both WT iPSC-CMs and $403^{+/-}$ iPSC-CMs, with a purity of 80% and 85% respectively.

WT and $403^{+/-}$ tissues were generated in the platform as described previously. Tissues were not subjected to electrical stimulation. Optical videos were taken at Day 14 for force measurements and analysis.

Figure 10A:
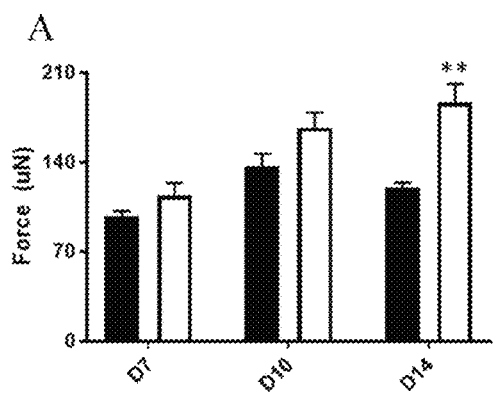
FIG. 10A-10C shows the effect of ascorbic acid on contractile force over time of wild-type (WT) and mutant ($403^{+/-}$) tissues.
Figure 10B:
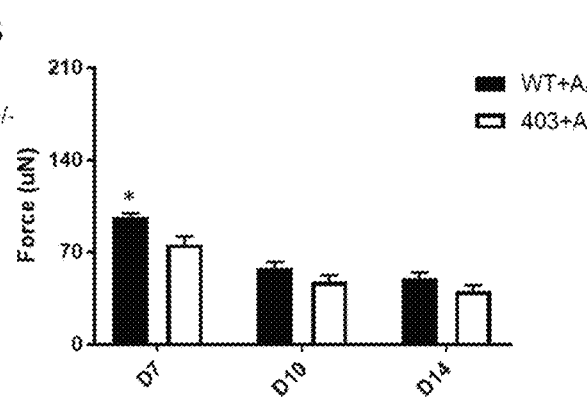
Figure 10C:
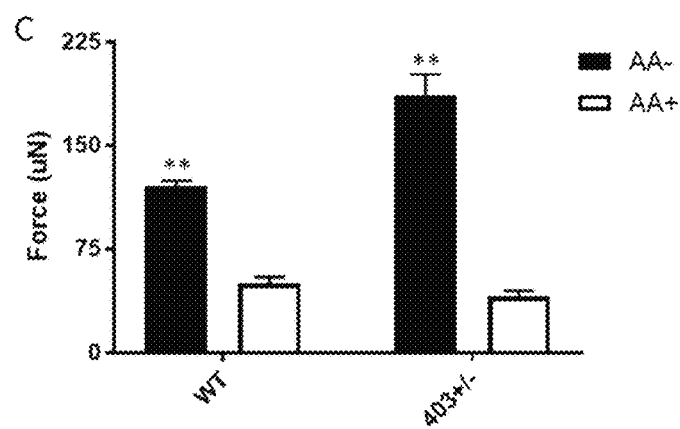
Figure 11A:
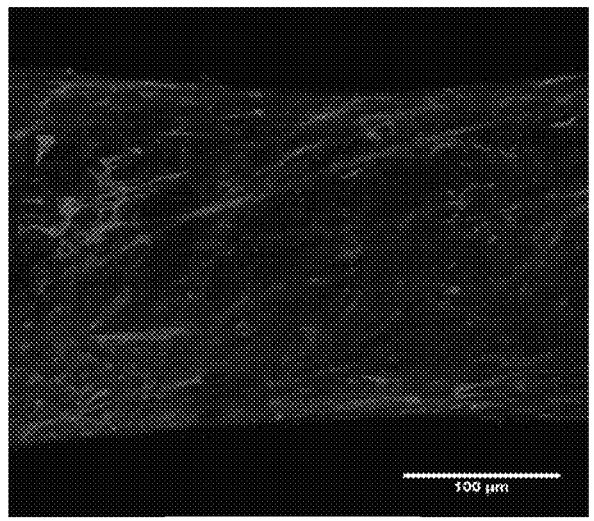
FIGS. 11A-11C show immunofluorescence staining of collagen in WT and $403^{+/-}$ tissues.
Figure 11B:
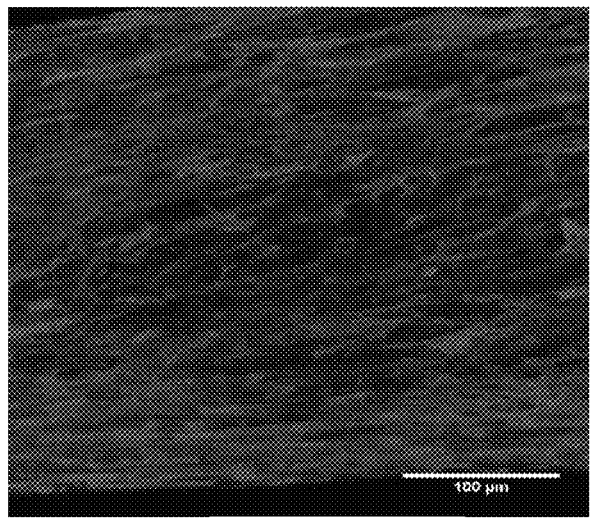
Figure 11C:
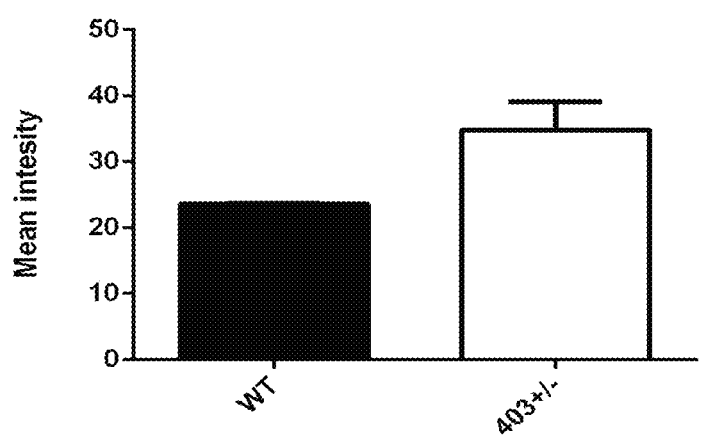

The contractile performance of WT and $403^{+/-}$ tissues were assessed under several conditions. Under standard culture conditions, there was an increase in contractile force over time (FIG. 10A). At each time point, $403^{+/-}$ tissues exhibited higher contractile force than WT tissues, and the difference in contractile force at Day 14 was statistically significant. Ascorbic acid (AA, 0.15 mg/ml) was added to promote collagen deposition in the tissues. With the addition of ascorbic acid (AA+), contractile force of both WT and $403^{+/-}$ tissues decreased over time (FIG. 10B). At each time point, WT tissues exhibited higher contractile force than $403^{+/-}$ tissues, and the difference at Day 7 was statistically significant. At day 14, there is a 58.4% difference in force between WT tissues with and without ascorbic acid (AA−). In the $403^{+/-}$ tissues, there is a 78.4% difference in force between AA+ and AA− tissues (FIG. 10C). Immunofluorescence staining and imaging showed that under the presence of ascorbic acid there was an increase in collagen deposition in $403^{+/-}$ tissues (FIG. 11B) compared to WT tissues (FIG. 11A).

These studies indicate that $403^{+/-}$ tissues produce higher contractile force than WT tissues. Further studies can be conducted to determine its cause, such as quantifying sarcomere content and sarcomere shortening Increased collagen deposition can increase the stiffness of the tissue, leading to a decrease in contractile force output. Thickening of the heart tissue is a clinical characteristic of HCM and the $403^{+/-}$ mutation[6]. Further studies can be conducted to determine why there is more collagen deposition in $403^{+/-}$ tissues than WT tissues in the presence of ascorbic acid.

Taken together, the data provided herein in the Examples section provides a new platform that increased tissue lifespan compared to the first-generation platform by more than 100%. An electrical stimulation regimen was developed that improved both tissue force output and calcium handling properties. When modeling the 403Q mutation associated with hypertrophic cardiomyopathy, under standard culture the mutated tissues produced higher contractile force than the WT tissues. Under the presence of ascorbic acid, the mutated tissues produced lower contractile force than the WT tissues. Immunofluorescent imaging showed an increase in collagen deposition in the mutated tissues treated with ascorbic acid compared to WT tissues. These findings indicate that this micro-device platform can be used for both mechanistic and drug discovery studies.

REFERENCES

1. Lloyd-Jones, D. et al. Executive summary: Heart disease and stroke statistics-2010 update: A report from the American heart association. Circulation 121, (2010).

2. Towbin, J. A. Inherited cardiomyopathies. Circ J 78, 2347-2356 (2014).

3. Marsiglia, J. D. C. & Pereira, A. C. Hypertrophic Cardiomyopathy: How do Mutations Lead to Disease? Arq. Bras. Cardiol. 295-304 (2014). doi:10.5935/abc.20140022

4. Geisterfer-Lowrance, A. A. T. et al. A molecular basis for familial hypertrophic cardiomyopathy: A β cardiac myosin heavy chain gene missense mutation. Cell 62, 999-1006 (1990).

5. Konno, T., Chang, S., Seidman, J. G. & Seidman, C. E. Genetics of hypertrophic cardiomyopathy. Curr. Opin. Cardiol. 25, 205-209 (2010).

6. Geisterfer-Lowrance, Anja A. T., Christe, Michael, Conner, David A., Ingwall, Joanne S., Schoen, Frederick J., Seidman, Christine E., Seidman, J. G. A Mouse Model of Familial Hypertrophic Cardiomyopathy. Science (80-.). 272, 731-734 (1996).

7. Karakikes, I., Ameen, M., Termglinchan, V. & Wu, J. C. Human Induced Pluripotent Stem Cell-Derived Cardiomyocytes: Insights into Molecular, Cellular and Functional Phenotypes. 117, 80-88 (2016).

8. Robertson, C., Tran, D. D. & George, S. C. Concise review: Maturation phases of human pluripotent stem cell-derived cardiomyocytes. Stem Cells 31, 829-837 (2013).

9. Lundy, S. D., Zhu, W.-Z., Regnier, M. & Laflamme, M. A. Structural and Functional Maturation of Cardiomyocytes Derived from Human Pluripotent Stem Cells. Stem Cells Dev. 22, 1991-2002 (2013).

10. Otsuji, T. G. et al. Progressive maturation in contracting cardiomyocytes derived from human embryonic stem cells: Qualitative effects on electrophysiological responses to drugs. Stem Cell Res. 4, 201-213 (2010).

11. Desroches, B. R. et al. Functional scaffold-free 3-D cardiac microtissues: a novel model for the investigation of heart cells. AJP Hear. Circ. Physiol. 302, H2031-H2042 (2012).

12. Zimmermann, W. H. et al. Tissue engineering of a differentiated cardiac muscle construct. Circ. Res. 90, 223-230 (2002).

13. Legant, W. R. et al. Microfabricated tissue gauges to measure and manipulate forces from 3D microtissues. Proc. Natl. Acad. Sci. 106, 10097-10102 (2009).

14. Hinson, J. T. et al. Titin mutations in iPS cells define sarcomere insufficiency as a cause of dilated cardiomyopathy. Science (80-.). 349, 982-986 (2015).

15. Radisic, M. et al. Functional assembly of engineered myocardium by electrical stimulation of cardiac myocytes cultured on scaffolds. Proc. Natl. Acad. Sci. 101, 18129-18134 (2004).

16. Nunes, S. S. et al. Biowire: A platform for maturation of human pluripotent stem cell-derived cardiomyocytes. Nat. Methods 10, 781-787 (2013).

17. Hirt, M. N. et al. Increased afterload induces pathological cardiac hypertrophy: A new in vitro model. Basic Res. Cardiol. 107, (2012).

18. Lian, X. et al. Directed cardiomyocyte differentiation from human pluripotent stem cells by modulating Wnt / b -catenin signaling under fully defined conditions. (2012). doi:10.1038/nprot.2012.150

19. Hansen, A. et al. Development of a drug screening platform based on engineered heart tissue. Circ. Res. 107, 35-44 (2010).

20. Germanguz, I. et al. Molecular characterization and functional properties of cardiomyocytes derived from human inducible pluripotent stem cells. J. Cell. Mol. Med. 15, 38-51 (2011).

21. Ronaldson, K. et al. Advanced maturation of human cardiac tissue grown from pluripotent stem cells. Nature (2018). doi:10.1038/s41586-018-0016-3

22. Nag, S. et al. Contractility parameters of human -cardiac myosin with the hypertrophic cardiomyopathy mutation R403Q show loss of motor function. Sci. Adv. 1, e1500511-e1500511 (2015).

All of the references cited herein are specifically incorporated by reference in their entirety.

The invention claimed is:

1. A system for generating 3-dimensional (3D) cardiac tissues, the system comprising:
 a. a solid support base;
 b. a well in the support base, the well including a lower chamber and an upper chamber;
 c. at least two pillars in the lower chamber operable to produce cardiac tissues across the pillars; and
 d. a spherically shaped head on top of each of the at least two pillars,
   wherein each of the spherically shaped heads includes a portion overhanging each of the at least two pillars,
   wherein each of the spherically shaped heads protrude into the upper chamber,
   and wherein each of the spherically shaped heads are coated with plasma, poly-lysine, and/or glutaraldehyde.

2. The system of claim 1, further comprising muscle cells, cardiomyocytes, or stem cells in the well.

3. The system of claim 1, wherein the pillars are flexible and permit contraction of the cells.

4. The system of claim 1, wherein the pillars are 0.01 to 2.0 millimeters (mm) in height.

5. The system of claim 1, wherein a spring constant of the pillars is at least 0.05 micronewtons/micrometer ($\mu$N/$\mu$m).

6. The system of claim 1, wherein the upper chamber is larger than the lower chamber, and wherein the upper chamber includes a tapered wall in contact with the lower chamber.

7. The system of claim 1, further comprising:
 at least one additional well having a lower chamber and an upper chamber in the solid support base comprising:
 a. at least two pillars in the lower chamber of the at least one additional well operable to produce cardiac tissues between the pillars; and
 b. a spherically shaped head on top of each of the at least two pillars,
   wherein each of the spherically shaped heads include a portion overhanging each of the at least two pillars,
   wherein each of the spherically shaped heads protrude into the upper chamber of the at least one additional well.

8. The system of claim 1, further comprising an extracellular matrix in the well.

9. The system of claim 1, wherein the solid support base is fabricated from polydimethylsiloxane (PDMS), polyurethane (PU), and/or poly(ethylene glycol) (PEG).

10. The system of claim 1, further comprising a stimulator having an electrode that generates an electrical stimulus to the well and/or pillars.

11. The system of claim 1, further comprising a measurement device operable for measuring contractile function of the tissue generated in the well.

12. The system of claim 1, further comprising a device for measuring the electrical function of the tissue.

13. The system of claim 1, further comprising cells adhered to the pillars to form the tissue spanning across the pillars.

14. A device for generating 3-dimensional (3D) cardiac tissues, the device comprising:
 a. a solid support base having a top surface;
 b. a plurality of wells accessible through the top surface, each of the wells including a top well and a lower base well;
 c. at least two pillars in each of the lower base wells operable to produce cardiac tissues across the pillars; and
 d. a spherically shaped head on top of each of the at least two pillars,
   wherein each of the spherically shaped heads include a portion overhanging each of the at least two pillars,
   wherein each of the spherically shaped heads protrude into the corresponding top well,
   and wherein each of the spherically shaped heads are coated with plasma, poly-lysine, and/or glutaraldehyde.

* * * * *